(12) United States Patent
Dower et al.

US007413536B1

(10) Patent No.: US 7,413,536 B1
(45) Date of Patent: Aug. 19, 2008

(54) SUBSTRATES AND SCREENING METHODS FOR TRANSPORT PROTEINS

(75) Inventors: William J. Dower, Menlo Park, CA (US); Mark A. Gallop, Santa Clara, CA (US); Ronald W. Barrett, Saratoga, CA (US); Kenneth C. Cundy, Redwood City, CA (US); Tania Chernov-Rogan, Los Altos, CA (US)

(73) Assignee: XenoPort, Inc., Santa Clara, CA (US)

( * ) Notice: Subject to any disclaimer, the term of this patent is extended or adjusted under 35 U.S.C. 154(b) by 0 days.

(21) Appl. No.: 09/661,927

(22) Filed: Sep. 14, 2000

Related U.S. Application Data

(60) Provisional application No. 60/154,071, filed on Sep. 14, 1999.

(51) Int. Cl.
*C40B 30/04* (2006.01)
(52) U.S. Cl. ................................ 506/9; 506/11; 506/12
(58) Field of Classification Search ..................... 435/6, 435/7.1, DIG. 2
See application file for complete search history.

(56) References Cited

U.S. PATENT DOCUMENTS

| | | | |
|---|---|---|---|
| 5,236,902 A | 8/1993 | Paterson et al. | |
| 5,462,933 A | 10/1995 | Kramer et al. | |
| 5,514,548 A | 5/1996 | Krebber et al. | |
| 5,589,358 A * | 12/1996 | Dawson ..................... | 435/69.1 |
| 5,607,691 A | 3/1997 | Hale et al. | |
| 5,668,126 A | 9/1997 | Kramer et al. | |
| 5,719,043 A | 2/1998 | Frommer | |
| 5,750,362 A | 5/1998 | Frommer et al. | |
| 5,759,788 A | 6/1998 | Fremeau, Jr. et al. | |
| 5,780,264 A | 7/1998 | Wessling-Resnick et al. | |
| 5,824,485 A * | 10/1998 | Thompson et al. ............. | 435/6 |
| 5,837,500 A | 11/1998 | Ladner et al. | |
| 5,849,525 A | 12/1998 | Hediger | |
| 5,866,123 A | 2/1999 | MacLeod | |
| 5,869,265 A | 2/1999 | Dawson | |
| 5,902,609 A | 5/1999 | Lee | |
| 5,932,424 A | 8/1999 | Amara et al. | |
| 6,057,098 A | 5/2000 | Buechler et al. | |

FOREIGN PATENT DOCUMENTS

| | | |
|---|---|---|
| WO | WO 97/10507 | 3/1997 |
| WO | WO 97/17613 | 5/1997 |
| WO | WO 97/17614 | 5/1997 |
| WO | WO 98/02451 | 1/1998 |
| WO | WO 98/38490 A1 | 9/1998 |
| WO | WO 98/51325 | 11/1998 |
| WO | WO 98/51825 | 11/1998 |
| WO | WO 99/03823 | 1/1999 |

OTHER PUBLICATIONS

Abe, H.; Satoh, M.; Miyauchi, S.; Shuto, S.; Matsuda, A.; Kamo, N. Conjugation of Dipeptide to Fluorescent Dyes Enhances its Affinity for a Dipeptide Transporter (PEPT1.*
Swaan, P. W.; Hillgren, K. M.; Szoka, F. C.; Oie, S. "Enhanced Transepithelial Transport of Peptides by Conjugation to Cholic Acid" Bioconjugate Chem. 1997, 8, 520-525.*
Boyer, J. L.; Ananthanarayanan, O. -C.; Hofmann, A. F.; Schteingart, C. D.; Hagenbuch, B.; Stieger, B.; and Meier, P. J. American Journal of Physiology 1994, 266(3), G382-G387.*
Schaeffer, J. M.; Hsueh, A. J. W. "a-Bungarotoxin-Luciferin As a Bioluminescent Probe for Characterization of Acetylcholine Receptors in the Central Nervous System" J. Biol. Chem. 1984, 259(4), 2055-2058.*
Schramm U.; Dietrich, A.; Schneider, S.; Buscher, H. P.; Gerok, W.; Kurz, G. "Fluorescent derivatives of bile salts. II. Suitability of NBD-amino derivatives of bile salts for the study of biological transport" J. Lipid Res. 1991, 32, 1769-1779.*
Swanson, S. J.; Bethke, P.; Jones, R. L. "Barley Aleurone Cells Contain Two Types of Vacuoles: Characterization of Lytic Organelles by Use of Fluorescent Probes" The Plant Cell May 1998, 10, 685-698.*
Ozkan P.; Mutharasan, R. "A rapid method for measuring intracellular pH using BCECF-AM" Biochim. Biophys. Acta. 2002, 1572, 143-148.*
Homolya et al. "Fluorescent Cellular Indicators are Extruded by the Multidrug Resistance Protein" J. Biol. Chem. 1993, 368(29), 21493-21496.*
Blevis et al. "A Fluorescence-Based High Throughput Screen for the Transporter Associated with Antigen Processing" J. Biomol. Screen. 1999, 4(2), 87-91.*
Abe, et al., "Conjugation of Dipeptide to Fluorescent Dyes Enhances Its Affinity for a Dipeptide Transporter (PEPT1) in Human Intestinal Caco-2 Cells," *Bioconjugate Chem.* 10:24-31 (1999).
Börner, et al., "Transport of Amino Acid Aryl Amides by the Intestinal H+/peptide Cotransport System, PEPT1," *Eur. J. Biochem.* 255:698-702 (1998).
Delie, Florence, "Evaluation of Nano- and Microparticle Uptake by the Gastrointestinal Tract," *Advanced Drug Delivery Reviews*, 34:221-233 (1998).
Dieck, et al., "The Peptide Transporter PepT2 is Expressed in Rat Brain and Mediates the Accumulation of the Fluorescent Dipeptide Derivative β-Ala-Lys-$N_e$-AMCA in Astrocytes," *GLIA* 25:10-20 (1999).

(Continued)

*Primary Examiner*—Jon D Epperson
(74) *Attorney, Agent, or Firm*—Townsend and Townsend and Crew LLP

(57) ABSTRACT

A variety of methods for assaying libraries of test compounds as ligands and/or substrates of transport proteins, including both carrier-type and receptor-type transport proteins, are provided. Both in vitro and in vivo screening methods are disclosed. Also provided are methods for screening DNA libraries to identify members that encode transport proteins. Pharmaceutical compositions including compounds identified via the screening methods are also provided.

8 Claims, 30 Drawing Sheets

OTHER PUBLICATIONS

Florence, Alexander T., "The Oral Absorption of Micro- and Nanoparticulates: Neither Exceptional Nor Unusual," *Pharmaceutical Research*, 14(3):259-266 (1997).

Han, et al., "5'-Amino Acid Esters of Antiviral Nucleosides, Acyclovir, and AZT are Absorbed by the Intestinal PEPT1 Peptide Transporter," *Pharmaceutical Research*, 15(8):1154-1159 (1998).

Hussain, et al., "Enhanced Oral Uptake of Tomato Lectin-Conjugated Nanoparticles in the Rat," *Pharmaceutical Research*, 14(5):613-618 (1997).

Kramer, et al., "Intestinal Absorption of Peptides by Coupling to Bile Acids," *The Journal of Biological Chemistry* 269(14):10621-10627 (1994).

McLean, et al., "Binding and Uptake of Biodegradable Poly-DL-lactide Micro- and Nanoparticles in Intestinal Epithelia," *European Journal of Pharmaceutical Sciences*, 6:153-163 (1998).

Mills, et al., "Biliary Excretion of Chenodeoxycholyllysylrhodamine in Wistar Rats: A Possible Role of a Bile Acid as a Carrier for Drugs," *Biochimica et Biophysica Acta* 1126:35-40 (1992).

Otto, et al., "Dipeptide Uptake by Adenohypophysial Folliculostellate Cells," *Am. J. Physiol.* 271 (*Cell Physiol.* 40): C210-C217 (1996).

Swaan, Peter W., "Recent Advances in Intestinal Macromolecular Drug Delivery via Receptor-mediated Transport Pathways," *Pharmaceutical Research*, 15(6):826-834 (1998).

Tsuji, et al., "Carrier-mediated Intestinal Transport of Drugs," *Pharmaceutical Research*, 13(7):963-977 (1996).

Crawford, James M. et al., "Physical and biological properties of fluorescent dansylated bile salt derivates: the role of steroid ring hydroxylation," Biochimicia et Biophysica Acta 1085, pp. 223-234, 1991.

Holzinger, Fernando et al., "Fluroescent bile acid derivatives: Relationship between chemical structure and hepatic and intestinal transport in the rat," Hepatology, vol. 26, No. 5, pp. 1263-1271, Nov. 1997.

Maglova, Lilia M. et al.,"Transport characteristics of three flourescent conjugated bile acid analogs in isolated rat hepatocytes and couplets," Hepatology, vol. 22, No. 2, pp. 637-647, 1995.

Mills, Charles O., "Synthesis, physical and biological properties of lithocholyl-lysyl-fluorescein: a fluorescent monohydroxy bile salt analogue with cholestatic properties," Biochimica et Biophysica Acta 1336, pp. 485-496, 1997.

Schneider, S. et al., "Fluorescent derivatives of bile salts. I. Synthesis and properties of NBD-amino derivatives of bile salts," Journal of Lipid Research, vol. 32, pp. 1755-1767, 1991.

Schramm, U. et al., "Fluorescent derivatives of bile salts. II. Suitability of NBD-amino derivatives of bile salts for the study of biological transport," Journal of Lipid Research, vol. 32, pp. 1769-1779, 1991.

Alberts et al, "Comparison of passive and active transport," Access Excellence, Garland Publishing, 1998.

Bravo, Pilar et al., "Efficient In Vitro Vectorial Transport of a Fluorescent Conjugated Bile Acid Analogue by Polarized Hepatic Hybrid WIF-B and WIF-B9 Cells," Hepatology, vol. 27, pp. 576-583, 1998.

Buscher, H.P. et al. "Visualization of bile salt transport with fluorescent derivatives," Chapter 32 of *Enterohepatic Circulation of Bile Acids and Sterol Metabolism*, 1984, pp. 243-247, MTP Press Limited.

Wilton, J. et al., "Fluorescent Choleretic and Cholestatic Bile Salts Take Different Paths across the Hepalocyte: Transcytosis of Glycolithocholate Leads to and Extensive Redistribution of Annexin II" J. Cell Biology, Oct. 1994, pp. 401-410, vol. 127, No. 2.

Swaan, Peter et al. "Use of the intestinal and hepatic bile acid transporters for drug delivery" Advanced Drug Delivery Reviews, 1996, pp. 59-82, vol. 20; Elsevier Science B.V.

Steffansen, Bente et al. "Intestinal solute carriers: an overview of trends and strategies for improving oral drug absorption" European Journal of Pharmaceutical Sciences, 2004, pp. 3-16, vol. 21.

Yang Chen et al. "Prodrug based optimal drug delivery via membrane transporter/receptor" Exp. Opin. Biol. Ther., 2001, pp. 159-175, vol. 1, No. 2.

Hagenbuch, B., et al. "The superfamily of organic anion transporting polypeptides" Biochimica et Biophysica Acta, 2003, pp. 1-18, vol. 1609.

Kim, R. B. "Organic anion-transporting polypeptide (OATP) transporter family and drug disposition" European Journal of Clinical Investigation, 2003, pp. 1-5, vol. 33, Suppl. 2.

Van Montfoort, J.E., et al. "Drug Uptake Systems in Liver and Kidney" *Current Drug Metabolism*, 2003, pp. 185-211, vol. 4.

Uchino, Hiroshi, et al. "Transport of Amino Acid-Related Compounds Mediated by L-Type Amino Acid Transporter 1 (LAT1): Insights Into the Mechanisms of Substrate Recognition" Molecular Pharmacology, 2002, pp. 729-737, vol. 61, No. 4.

Tamai, Ikumi et al. "Participation of a Proton-Cotransporter, MCT 1, in the Intestinal Transport of Monocarboxylic Acids" Biochemical and Biophysical Research Communications, Sep. 14, 1995, pp. 482-489, vol. 214, No. 2.

Blevitt, Jonathan M. et al. "A Fluorescence-Based High Throughput Screen for the Transporter Associated with Antigen Processing" Journal of Biomolecular Screening, 1999, pp. 87-91, vol. 4, No. 2.

Kagedahl, Matts et al. "Use of the Intestinal Bile Acid Transporter for the uptake of Cholic Acid Conjugates with HIV-1 Protease Inhibitory Activity" Pharmaceutical Research, 1997, pp. 176-180, vol. 14, No. 2.

PCT International Search Report for PCT/US00/25439.
Written Opinion for PCT/US00/25439.
International Preliminary Examination Report for PCT/US00/25439.

* cited by examiner (i) R1 = OH; R2 = α-OH
(ii) R1 = OH; R2 = H
(iii) R1 = H; R2 = α-OH
(iv) R1 = H; R2 = β-OH
(v) R1 = H; R2 = H

SUBSTRATES AND SCREENING METHODS FOR TRANSPORT PROTEINS

CROSS-REFERENCES TO RELATED APPLICATIONS

This application claims the benefit of U.S. Provisional Application No. 60/154,071, filed Sep. 14, 1999, which is incorporated herein by reference in its entirety.

FIELD OF INVENTION

This invention relates to the fields of combinatorial chemistry and pharmaceutical agent delivery.

BACKGROUND OF THE INVENTION

Recent advances in biotechnology and chemistry have made available an increasing number of potential therapeutic agents. However, many agents fail at the preclinical or early clinical stage due to poor pharmacokinetics. Other potential targets for pharmaceutical agents are largely ignored due to anticipated problems of pharmaceutical agent delivery. Oral delivery of compounds is advantageous for reducing treatment costs and increasing patient acceptance. However, formulating compounds for efficient oral bioavailability has proven particularly difficult because of problems associated with uptake and susceptibility to metabolic enzymes in the intestinal tract. Likewise, delivery of compounds across the blood brain barrier or targeting compounds to specific tissues has proven problematic.

There are two major specific transport systems of xenobiotics into and through cells: carrier-mediated systems and receptor-mediated systems. Some xenobiotics can also be taken up by passive diffusion between or through cells. Carrier-mediated systems are effected by transport proteins that are anchored to the cell membrane, typically by a plurality of membrane-spanning loops and function by transporting their substrates via an energy-dependent flip-flop mechanism. Carrier-mediated transport systems are involved in the active transport of many important nutrients such as vitamins, sugars, and amino acids, as well as xenobiotic compounds. The carrier systems are involved in transport of such molecules from the lumen of the intestine into the systemic circulation or across the blood brain barrier. Carrier-mediated transporters are also present in organs such as liver and kidney, where the proteins are involved in the excretion or reabsorption of circulating compounds.

Receptor-mediated transport systems differ from the carrier-mediated systems in that rather than ferrying the substrate/ligand across the membrane, substrate binding triggers an invagination and encapsulation process that results in the formation of various transport vesicles to carry the substrate (and sometimes other molecules) into and through the cell. This process of membrane deformations that result in the internalization of certain substrates and their subsequent targeting to certain locations in the cytoplasm is referred to as endocytosis. Endocytosis encompasses several specific variations, including, for example, receptor mediated endocytosis (RME).

RME involves several defined steps beginning with the binding of a substrate to a cell-surface receptor and subsequent invagination of the membrane to form an internal vesicle variously called an early endosome, a receptosome or CURL (compartment of uncoupling receptor and ligand). In some endocytic events, after a substrate binds to its specific receptor, the substrate-receptor complex accumulates in coated pits that contain high concentrations of clathrin subunits that appear to aid in the membrane invagination process. Following internalization, the clathrin coat is lost and the pH in the endosome is lowered, thus resulting in the dissociation of the receptor-substrate complex. The endosome moves randomly or along microtubules to the trans-Golgi reticulum where the endosome is converted into one of a variety of different sorting vesicles (e.g., tubulovesicular complexes and late endosomes or multivesicular bodies). The fate of the receptor and substrate depends upon the type of sorting vesicle formed. Some ligands and receptors are recycled to the cell surface where the substrate is released and the receptor reinternalized into the membrane. In other instances, the substrate is directed to and destroyed in a lysosome, and the receptor is recycled. One type of RME is transcytosis, which refers to the process wherein an endocytotic vesicle is transported to the opposite membrane surface of a polarized cell.

RME is capable of transporting a variety of compounds, including immunoglobulins, lectins, vitamins and metal ions. Although some conflicting data has been obtained, it has been reported that certain small particles such as nanoparticles can be transported by endocytotic routes, particularly through both enterocytes and M-cells located in the intestine. Nanoparticles can be made of a variety of materials, and are typically between 1-999 nm in diameter.

A number of attempts have been made to assay or identify substrates of various transport proteins or to modify pharmaceutical agents to be improved substrates of transport proteins. (See, e.g., Kramer et al, *J. Biol. Chem.* (1994), 269: 10621; Mills et al, *Biochim. Biophys. Acta* (1992), 1126: 35; Börner et al, *Eur. J. Biochem.* (1998) 255: 698; Dieck et al, *Glia*, (1999) 25: 10; Otto et al, *Am. J. Physiol.* (1996) 271: C210; Abe et al, *Biooconjugate Chem.* (1999) 10: 24); Hussain et al, *Pharm. Res.* 1997, 14, 613 and McClean et al, *Eur. J. Pharm. Sci.* 1998, 6, 153). Some assays have involved measuring the uptake or transcellular flux of labeled compounds. Some assays have involved measuring uptake of unlabelled compound by HPLC. There have been a few successes. For example, Valtrex, a derivative of Zovirax, has 54% oral availability compared with Zovirax's 10-20% oral bioavailability. However, existing assays are tedious, low throughput, and the delivery of many pharmaceutical agents and potential pharmaceutical agents remains to be improved.

SUMMARY OF THE INVENTION

Disclosed herein are a variety of methods for screening individual or test complexes for activity as ligands for various transport proteins. Certain methods can be performed to distinguish compounds that are substrates and internalized within a cell from compounds that simply bind to a cell surface. Because the methods are amenable to high throughput screening formats and can be used to screen large libraries of complexes, one can accumulate data on structural and electronic features of those compounds that are substrates, thus allowing structure-activity relationships to be discerned. Such information in turn can be utilized in the design of pharmaceutical agents having improved cellular uptake.

By screening complexes that include a reporter, compounds that are substrates for various transport proteins can be readily detected. Use of a reporter has the additional advantage in that it can serve as a surrogate for a pharmaceutical agent. Thus, certain methods involve initially screening a library of complexes to identify a substrate and then replacing the reporter with a-pharmaceutical agent and rescreening to determine whether the substrate-drug conjugate is able to be taken up by the cell. Thus, the methods can be used to develop complexes for use in drug delivery.

The methods can be performed in a variety of formats, including multiplexed formats, as well as being performed in vitro and in vivo. Some assays are conducted with complexes that include a particle such as a nanoparticle to which a compound is attached or internalized. Complexes found to be active can be formulated as pharmaceutical compositions.

Thus, more specifically, certain methods are designed to screen for a carrier-type transport protein and/or a ligand thereto. Such methods initially involve providing a library comprising different complexes, each complex comprising a compound and a reporter, the compound varying between different complexes. A population of cells is also provided, one or more of which expresses one or more carrier-type transport proteins. The population of cells is contacted with a plurality of complexes from the library. Subsequently, a signal from the reporter of a complex that is bound to a cell or internalized within a cell is detected. The signal provides an indication that a complex whose reporter generated the signal comprises a compound that is a ligand for a carrier-type transport protein.

Such screening methods can optionally utilize various techniques to selectively detect signal from inside the cell rather than signal arising from complexes located at the cell surface or in solution. One simple means for achieving this end is to wash or soak the cells in a wash solution to remove unincorporated complexes. Other methods are performed with fluorescent complexes and the cells being assayed are contacted with a quenching solution that quenches signal from unincorporated complexes.

Other methods employ various conditional reporters. A signal from reporters of this type is not generated (or at least not substantially generated) until the reporter is internalized within the cell (e.g., less than 5 to 30% of the total signal detected is from non-internalized complexes). Thus, signal arising from complexes that are bound to the cell surface or that are in solution is minimal.

Certain methods using such reporters utilize a reporter that includes a fluorophore and a quencher moiety. Outside the cell, the quencher is disposed relative to the fluorophore such that it quenches fluorescence from the fluorophore. However, if the reporter is internalized within the cell, the intracellular conditions are such that the quencher can no longer effectively quench fluorescence emitted from the fluorophore. In certain systems, an intracellular enzyme cleaves the complex to release the quencher from the complex so that it no longer is in sufficiently close proximity to quench the fluorophore.

Reporters in other systems include a detection moiety disposed to interact with an intracellular agent located within the cells. If a complex is transported into the cell, the detection moiety interacts with the intracellular agent to generate a detectable signal. Certain methods using this type of reporter utilize a nucleic acid-binding dye that binds to nucleic acids within the cells to generate a signal. Other conditional reporters include a substrate for an enzyme. If a compound complexed with the reporter is a substrate for the carrier-type protein, the complex is transported into a cell where an intracellular enzyme (either endogenous or exogenous) metabolizes the enzyme substrate to form a detectable product.

A variety of conditional reporters include bioactive moiety that can cause some type of change within the cell. For instance, the reporter can include an agent that causes a morphological change upon internalization within a cell, which morphological change can be detected. Other reporters once internalized within a cell act to promote the aggregation of subunits of a multimeric enzyme expressed within the cells.

Still other reporters promote transcription from a promoter within a cell resulting in expression of an expression product that generates a detectable signal. The reporter can also confer a selective advantage within cells. In methods utilizing such reporters, after the cells being assayed have been contacted with complexes, the cells are propagated under conditions that enrich for cell(s) on which the selective advantage has been conferred.

As indicated above, the methods can be performed in multiplex formats in which different cells expressing different transport proteins and/or different complexes having different compounds are assayed within a single reaction vessel. To facilitate analysis, various methods can be utilized to differentiate between different cells and different complexes. For instance, if different cells expressing different transporters are simultaneously assayed, the cells can be selected to have different morphological characteristics or can be differentially stained. Different complexes can be distinguished by using complexes that have different labels.

In another aspect, the methods can be performed in an iterative fashion to identify compounds having enhanced activity. Thus, a compound identified as being a substrate in an initial screen can serve as the basis for generating another library, the members of which are variants that are related to the compound identified in the initial screen.

Once a compound that functions as a substrate is identified, the reporter can be replaced with a drug and the resulting complex then rescreened for activity to identify compounds that can effectively transport pharmaceutical agents.

Alternatively, or in addition, the methods can also be utilized to screen for new transport proteins using cells that have been transformed with a DNA library. Cells demonstrating the ability to bind to or be internalized within a complex can be isolated, the DNA therein removed, and the DNA characterized to identify a DNA molecule that encodes for a transport protein that exhibits activity with the compound of the complex that bound to, or was internalized by, the isolated cell.

The invention also provides a variety of screening methods to identify substrates for receptor-type transport proteins. Certain of these methods are related to methods for screening carrier-type transport proteins. For instance, certain methods involve providing a library comprising different complexes, each complex comprising a compound and a reporter, the compound varying between different complexes. A population of cells, one or more of which expresses one or more receptor-type transport proteins, is also provided. This population of cells is then contacted with a plurality of complexes from the library. A signal from the reporter of a complex that is bound to a cell, internalized within a cell or has been transported through a cell is then detected. Such a signal provides an indication that a complex whose reporter generated the signal comprises a compound that is a ligand for a receptor-type transport protein. These methods can also be adapted to be performed using the various conditional reporters described for the assays of carrier-type transporter and can also be conducted in multiplex format.

Certain screens are conducted using complexes that include a support, with the compound and reporter attached or enclosed therein. Various supports can be utilized including, for example, nanoparticles. In certain methods, the ability of a compound to pass through a cell via transcytotic mechanisms can be detected by forming a monolayer of cells and then detecting the position of reporter relative to the cells in the monolayer. In some methods, detection is done at intervals to track internalization of a complex into a cell.

A variety of in vivo screening methods are also provided. Certain of these methods involve introducing into a body compartment of an animal a population of complexes, each complex comprising a support, a test compound, and a reporter, the test compound varying between complexes. Typically the reporter is the same, although different complexes bearing different compounds can in some instances also bear different reporters. Subsequently, complexes are recovered by means of their reporter from a tissue or fluid of the animal after transport of at least some of the complexes through cells lining the body compartment. The body compartment through which transport is monitored often is the lumen of the gastrointestinal tract.

Certain of the in vivo methods involve repeating the method with the recovered complexes such that recovered complexes from one cycle form the population of complexes to be introduced into the body compartment of the animal in the next cycle. In such iterative methods, the animal used in each cycle can be the same or different.

Recovered complexes showing activity can be used to screen for potential transport proteins. For instance, certain methods involve contacting recovered complexes with a population of polarized cells transformed with a DNA library at least some members of which encode potential transport proteins, the cells being arranged as a monolayer on a membrane and the complexes contacting the apical side of the cells. Complexes transported through the polarized cells to the membrane are detected by virtue of the reporter of the complexes. Polarized cells in proximity to the transported complexes are recovered and then clonally expanded.

Compounds identified via the various screening mechanisms can be utilized to prepare pharmaceutical compositions. Certain of these compositions include a nanoparticle, a drug within or linked to the nanoparticle and a ligand linked to or within the nanoparticle, the ligand being effective to promote cellular uptake and/or transport of the particle by receptor-type transport proteins. The nanoparticles of some compositions also include a second ligand attached to, or internalized within, the nanoparticle. The second ligand can be utilized for various purposes. In some instances, the ligand binds to a first cellular receptor, and the second ligand binds to a transport protein, which binding results in internalization of the nanoparticle. In other instances, the ligand binds to a receptor-type transport protein, which binding results in internalization of the nanoparticle, and the second ligand binds to a second transport protein within a cell that effects basolateral trafficking of the internalized nanoparticle to the basolateral exterior of the cell. The nanoparticle can also be linked or contain other agents, such as a buffering agent, an antacid and/or a cell lysing agent, for example.

BRIEF DESCRIPTION OF THE DRAWINGS

FIG. 22 shows the major steps in the synthesis of cholyl-L-Lys-(ϵ-NBD)-OH that is a substrate for the rat intestinal bile acid transporter. FIG. 23 shows the synthesis of a related compound in which the NBD reporter is replaced with the drug Naproxen and which retains activity with the rat intestinal bile acid transporter. FIG. 24 depicts the preparation of the propharmaceutical agent Cholyl-L-Dopa.

FIG. 26A shows the efflux of tritiated Gly-Sar when CHO cells expressing PEPT1 are contacted with varying concentrations of untritiated Gly-Sar. FIG. 26B shows the results from related experiments in which the efflux of tritiated taurocholate is detected from CHO cells expressing LBAT when contacted with the untritiated cholate analogs Gly-CDC-acid (glycochenodeoxycholic acid) and Gly-CDC-ethyl ester.

FIG. 27A shows inhibition plots for CHO cells expressing IBAT when contacted with one of two known substrates (cholic acid or taurocholate) in the presence of tritiated taurocholate. FIG. 27B presents the inhibition plot for cells expressing PEPT1 when contacted with either of the known substrates Gly-Sar or Enalapril and the tritiated inhibitor Gly-Sar.

DETAILED DESCRIPTION

I. Definitions

Figure 1:
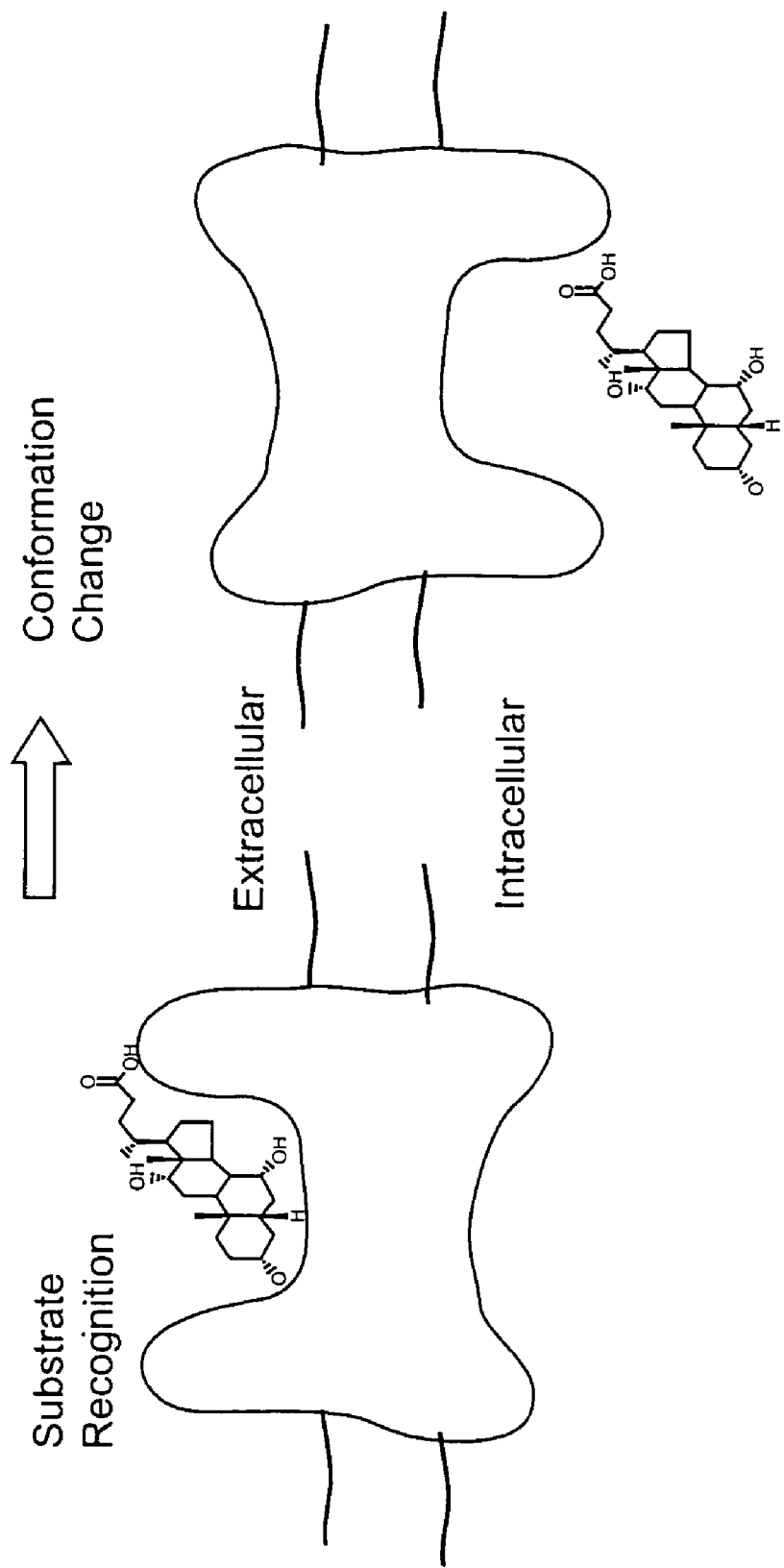
FIG. 1 illustrates transport of a substrate into a cell by a carrier-type transporter.
Figure 2B:
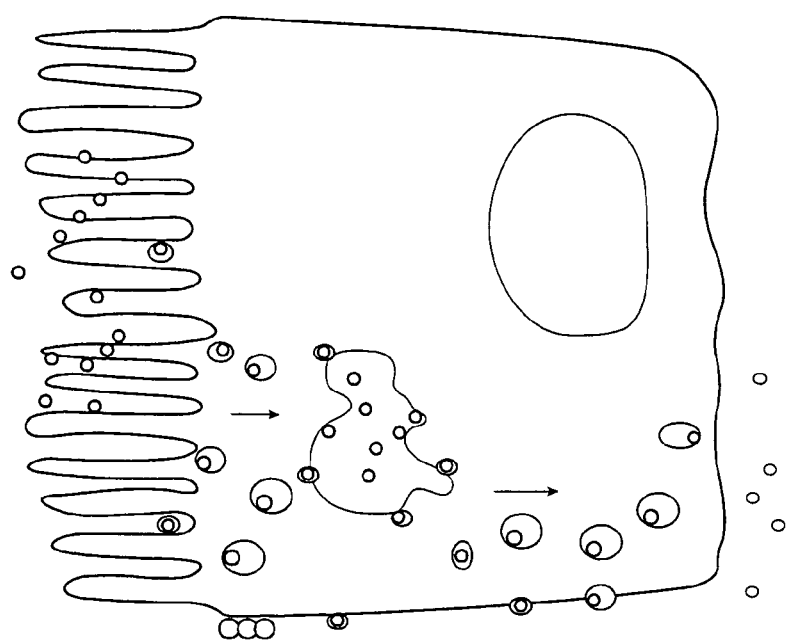
FIGS. 2A and 2B illustrate transport of a substrate into a cell by a receptor-type transporter in which substrates bind to cell-surface receptors and are subsequently encapsulated into vesicles and transported into and/or through the cell from the intestinal lumen to the blood system.
Figure 2A:
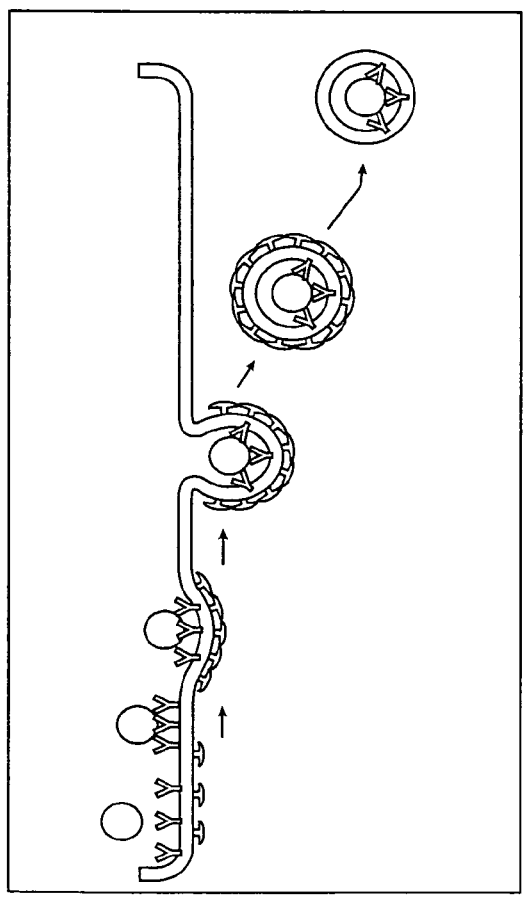

A "transport protein" is a protein that has a direct or indirect role in transporting a molecule into and/or through a cell. The term includes, for example, membrane-bound proteins that recognize a substrate and effects its entry into a cell by a carrier-mediated transporter (see FIG. 1) or by receptor-mediated transport (see FIGS. 2A and 2B). Transport proteins are sometimes referred to as "transporter proteins" or simply "transporters." The term also includes intracellularly expressed proteins that participate in trafficking of substrates through or out of a cell. The term also includes proteins or glycoproteins exposed on the surface of a cell that do not directly transport a substrate but bind to the substrate holding it in proximity to a receptor or transporter protein that effects entry of the substrate into or through the cell. Transport proteins involved in carrier-mediated transport are referred to as carrier-type transport proteins or simply carrier-type transporters. Those transport proteins involved in receptor-mediated transport are referred to as receptor-type transport proteins or simply receptor-type transporters.

Some examples of transporter proteins effecting carrier-mediated transport of nutrients, vitamins and xenobiotics include, but are not limited to: glutamate/neutral amino acid transporter; facilitated glucose transporter; d2/NBAT and 4F2 transporter; sodium/glucose transporter; GABA transporter; amino acid permease transporter; sodium/bile acid transporter; proton/oligopeptide transporter; monoamine transporter; folate transporter; organic anion/prostaglandin transporter; organic cation/organic anion transporter; sodium/ascorbic acid transporter; fatty acid transporter; sodium/nucleoside transporter and facilitated nucleoside transporter. Other examples of carrier proteins include: the ileal bile acid transporter (ASBT or IBAT); the liver bile acid transporters (NTCP); dipeptide transporters; oligopeptide transporters; simple sugar transporters (e.g., SGLT1); phosphate transporters; monocarboxylic acid transporters; ATP-binding cassette (ABC) family (e.g., P-glycoprotein); organic anion transporters (OATP); organic cation transporters; amino acid transporters; nucleoside transporters; vitamin transporters; and electrogenic transporters that carry charged substrates. Examples of receptor-mediated transport proteins include: viral receptors, immunoglobulin receptors, bacterial toxin receptors, plant lectin receptors, bacterial adhesion receptors, vitamin transporters and cytokine growth factor receptors.

Abbreviated references to transporters sometimes begin with a small letter to indicate the source of the transporter. Thus, for example, hPEPT1 and hMDR1 refer to the human PEPT1 and MDR1 transporters, respectively. Likewise rpept1 and rmdr1 refer to the pept1 and mdr1 transporters in rat. Specific examples of transport proteins include hPEPT1, rpept1, hPEPT2, rpept2, hIBAT, hLBAT, rLBAT, hMDR1, rmdr1a, rmdr1b, hMRP3, hMRP1, rat oatp1, rat oatp2, rat oatp3, hOATP-A, hOATP-C, rat oatp-c, hBSEP, rBSEP, rat mrp3, hMRP2, rat mrp2, rat oat2, rat oat3, hOCT1, rat oct1 and rat mEH.

A "substrate" of a transport protein is a compound whose uptake into or passage through a cell is facilitated by the transport protein. Some existing drugs that are substrates for the PEPT1 transporter include: antibacterial drugs (e.g., Cefadroxil, Ceftibuten, and Cyclacillin), antihypertensive drugs (e.g., Enalapril, Lisinopril and Captopril), vasodilators (e.g., pGlu-L-Dopa-Pro), anticancer drugs (e.g., Bestatin) and antiviral drugs (e.g., Valacyclovir). Some natural substrates of the bile acid transporter include cholic acid and taurocholic acid. Some drugs that are substrates for OATPs include Microcystin LR, Deltorphin and BQ-123.

The term "ligand" of a transport protein includes substrates and other compounds that bind to the transport protein without being taken up or transported through a cell. Some ligands by binding to the transport protein inhibit or antagonize uptake of the compound or passage of the compound through a cell by the transport protein. Some ligands by binding to the transport protein promote or agonize uptake or passage of the compound by the transport protein or another transport protein. For example, binding of a ligand to one transport protein can promote uptake of a substrate by a second transport protein in proximity with the first transport protein.

A "small molecule" means a synthetic molecule having a molecular weight of less than 1000 daltons, more typically 500 daltons or less. Such molecules include, for example, sterols, amino acids, lipids and nucleic acids.

An "expression cassette" is a nucleic acid construct, generated recombinantly or synthetically, that has control elements that are capable of effecting expression of a structural gene that is operably linked to the control elements in hosts compatible with such sequences. Expression cassettes include at least promoters and optionally, transcription termination signals. Typically, the recombinant expression cassette includes at least a nucleic acid to be transcribed (e.g., a nucleic acid encoding a transport protein) and a promoter. Transcription termination signals, enhancers, and other nucleic acid sequences that influence gene expression, can also be included in an expression cassette.

An "encoded library" is a library of compounds in which each compound is linked to a tag recording at least one step in synthesis of the compound. Conversely, a non-encoded library is a library of compounds lacking tags.

An "exogenous" species is refers to a species that is not normally present in a cell, but can be introduced into a cell by one or more genetic, biochemical or other methods. Normal presence in the cell is determined with respect to the particular developmental stage and environmental conditions of the cell. Thus, for example, a molecule that is present only during embryonic development of muscle is an exogenous molecule with respect to an adult muscle cell. An exogenous species can be, among other things, a small molecule, such as is generated by a combinatorial chemistry process, or a macromolecule such as a protein, nucleic acid, carbohydrate, lipid, glycoprotein, lipoprotein, polysaccharide, or any modified derivative of the above molecules, or any complex comprising one or more of the above molecules.

By contrast, an "endogenous" species is one that is normally present in a particular cell at a particular developmental stage under particular environmental conditions.

The term "statistically significant difference" refers to a statistical confidence level, P, that is <0.25, preferably <0.05, and most preferably <0.01.

The terms "pharmaceutical agent," and "drug" are used interchangeably to refer to an agent suitable for delivery via a transport protein which induces a desired effect in the individual to which delivery is effected. The terms include agents that are therapeutically effective, as well as agents that are prophylactically effective.

II. General

The invention is based, in part, on the provision of a variety of assays that permit rapid detection of compounds that are substrates for, or which otherwise bind to, transport proteins. Such assays typically generate an optical signal that provides an indication of the activity, if any, of a test compound as a ligand for a transport protein. The assays can be performed in vitro or in vivo. Some assays can distinguish compounds that are substrates of a transporter protein from compounds that bind to a transporter protein without being substrates. In certain methods, this is accomplished by using reporters that preferentially generate a signal once internalized within a cell. The methods are amenable to multiplexing, enabling high-throughput screens to be performed. For example, different populations of cells expressing different transport proteins can be screened simultaneously within a single reaction vessel; similarly, different complexes having different compounds can be simultaneously screened against a single type of transport protein. Alternatively, cells expressing different transport proteins and different complexes can be screened at the same time within a single reaction vessel.

While methods can be performed with individual compounds, the assays also permit libraries of test compounds to be screened for potential activity as ligands. The libraries can be random libraries or can include variants of known substrates. The assays also permit screening of DNA libraries to identify members that encode transport proteins. Optionally, DNA libraries and compound libraries can be screened in the same assay. By screening libraries of complexes composed of substrates and/or reporters that vary with respect to substrates and reporters of complexes known to be transported, structure-activity relationships can be established. Information obtained by screening such libraries provides information, for example, on steric and/or electronic features that correlate with transport activity. Such information can be used in turn to rationally design complexes that are transported by a transport protein of interest.

Substrates of transport proteins identified by the methods can be linked to pharmaceutical agents thereby facilitating uptake of the pharmaceutical agents by a patient. In such methods, the reporter essentially acts as a surrogate for the pharmaceutical agent during initial screening. Once a substrate is identified, the reporter can be replaced with a pharmaceutical agent of interest. For example, a substrate for an intestinal epithelial cell transporter can be linked to a pharmaceutical agent via a linker that is either enzymatically and/or chemically cleavable or is non-cleavable. In the case of a cleavable linkage, the pharmaceutical agent derivative can be regarded as a propharmaceutical agent. A wide variety of cleavable linkages can be used in propharmaceutical agents depending on the nature of the functionality groups available for derivatization in the pharmaceutical agent molecule (vide infra).

Substrates for a receptor-type transporters can be linked to a particle containing a pharmaceutical agent to form a pharmaceutical composition. The particles can be taken orally by the patient, with the substrate facilitating passage of the particles through the layer of intestinal epithelial cells lining the gut. In some instances, the pharmaceutical compound is released from the particle and the intact particle subsequently excreted. In other instances, the particle is digested by intracellular enzymes resulting in release of the pharmaceutical agent. Some particles also include a ligand that directs trafficking of the particle to particular cellular organelles after the particle has been internalized within a cell.

Other ligands of transport proteins that are not themselves substrates are also useful. Some such ligands promote uptake of a substrate linked to the ligand. Such can be effected, for example, when a ligand binds to a cellular outer surface molecule in proximity with a carrier or receptor for the substrate thereby bringing the substrate into contact with the carrier or receptor. Some inhibitors of transport proteins are also useful as pharmaceutical agents. For example, inhibitors of nutrient transporters can be used in managing obesity, diabetes and hypercholesterolemia, for example.

New transporter proteins identified by the methods can themselves be screened for suitable substrates and other ligands, and these substrates and ligands used as described above. Structural information on new transporter proteins is also useful in designing pharmaceutical agents that bind or are transported by these proteins.

In Vitro Systems for Screening for Transport Proteins and Substrates

I. General Screening Methods

The methods involve contacting one or more cells expressing one or more transporter proteins with one or more complexes, each complex comprising at least a compound and a reporter. Typically, the reporter is capable of generating an optical signal. After incubating for a period sufficient to permit transport of the complex into the cell or to permit binding to the cell, the location of signal from the reporter is detected. Detection of the signal at a location within a cell, or at a location that indicates that a complex has passed through a cell, indicates that the complex comprises a compound that is a substrate for a transporter protein expressed by the cell. Detection of signal on the surface of a cell exposed to complexes (and not within a cell or at a surface distal to complexes) indicates that the complex contains a compound that binds to a cellular surface molecule. Such compounds include compounds that agonize or antagonize transport of substrates, as well as compounds that bind to cell surface components unrelated to transport.

Following detection of signal, one can isolate and characterize either or both the complex(es) responsible for generation of signal and the cell(s) that transported or bound such complexes. Complexes can be isolated from within or proximate to cells generating signal. The identity of a compound borne by such a complex can be decoded from an optional tag that is a component of such a complex or by deconvolution by a variety of chemical analyses, such as HPLC, mass spectrometry, infra red spectroscopy and nuclear magnetic resonance spectroscopy. Cells that have transported compounds can also be isolated from the location of signal within or proximate to a cell. Having isolated a cell, one can isolate from the cell a DNA fragment encoding the protein transporter responsible for transporting a complex that generated the signal within or proximate to the cell.

Although the methods can be performed in a single cell format, they are typically performed using a population of cells. Cells are contacted with libraries of complexes, or can be contacted with a single type of complex. In some methods, multiple copies of each complex type are present. Some methods also include conducting parallel screening experiments with a control cell or multiple control cells. The control cells do not express the transport protein(s) expressed by the test cells. Using such cells, it is possible to distinguish between bona fide uptake by the transport protein and other uptake processes (e.g., passive diffusion or cell lysis).

The cells can express natural endogenous transport proteins or can be transformed with DNA segment(s) encoding exogenous transport proteins. In the latter case, the cells can be transformed with a library of DNA fragments, such that different cells receive different fragments and express different candidate transport proteins. Alternatively, all cells can be transformed with the same DNA segment such that the cells express the same known transport protein or candidate transport protein. Exogenous DNA introduced into cells can exist integrated into the cell chromosomes or can exist in an episomal vector. The latter is preferred for ease of isolation.

The format of the assay depends, in part, on the cell type and the nature of the reporter. Certain assays are performed with both cells and complexes suspended in solution. Some assays are performed with cells linked to a solid phase, such as a plate or membrane. Other assays are performed on a monolayer of cells. As described in more detail below, the latter format is particularly suitable for polarized cells in that it allows complexes to be contacted with the apical surface of such cells, and detected on passage through the basal surface. Many assays can be performed in multi-well plates including 96 well plates, and similarly sized plates that include 384, 864, 1536 or 3456 wells. Assays conducted with these latter plates are useful in that smaller volumes are utilized and higher throughput is obtained. In many assays, the detection step can be performed homogeneously, i.e., without prior separation of cells from unincorporated and unbound complexes.

Still other assays are not conducted with whole cells but instead performed with membrane preparations or vesicles prepared from cells expressing the target transporters. Such membrane preparations and vesicles can be prepared according to established methods such as described by H. Bonisch, "Transport and Drug Binding Kinetics in Membrane Vesicle Preparation," *Methods in Enzymology* 296:259 (1998). Membrane preparations and vesicles prepared in this way can be used to assay uptake using the same general methods utilized with whole cells. However, assays conducted with vesicles instead of whole cells can be useful in assaying transporters such as from the ABC family that are efflux pumps. Assaying such transporters with vesicles is possible because a significant percentage of the vesicles in the preparation are "inside out," thereby allowing efflux pump transporters to cause uptake into the vesicle for detection. This is not possible using intact cells. Assays utilizing vesicles are described further in Example 17 supra.

The nature of the complex used in the screening methods depends, in part, on the type of transport protein being utilized in the assay. In general, assays of carrier-type transport proteins are conducted with complexes that comprise a substrate and a reporter. As described in greater detail infra, assays with receptor-type transport proteins can be conducted using complexes in which the substrate and reporter are optionally attached to a support (e.g., a bead or nanoparticle). Receptor-type transport proteins can accommodate complexes that include supports because the vesicles formed to effectuate transport are sufficiently large to contain such particles. Thus, while screening methods using cells that express receptor-type transport proteins can be conducted with complexes that contain particles, the methods can also be conducted with complexes that lack supports and that simply include a compound and a reporter.

II. Compound Identification and Assessment of Structure-Activity Relationships

The methods can be used in a variety of ways. In some methods, the goal is to identify compounds that are ligands for any transport protein expressed by a particular cell type, typically a natural cell. In such methods, a library of complexes bearing test compounds is contacted with a population of the cell type. Complexes binding to, internalizing within, or passing through cells are then identified, and compounds borne by such complexes are characterized. Optionally, complexes can be subject to a further iteration of the screening process with or without prior characterization. In other methods, the goal is to identify compounds that are ligands for a particular known transport protein. Such methods can proceed as just described using a cell type expressing the known transporter, typically with a substantially isogenic control cell type lacking the transporter. Alternatively, such methods can be performed using a population of cells transformed with DNA segments expressing the known transport protein.

Coupling the screening methods disclosed herein with the synthesis and use of selected combinatorial libraries, provides an efficient mechanism for defining structure-activity relationships (SAR) for transport proteins. It has unexpectedly been shown using the methods described herein that transporter structure-activity relationships can be effectively mapped out by screening combinatorial libraries of potential substrates that are conjugated to reporter groups. The ability to rapidly understand the requisite physiochemical characteristics (e.g., steric and electronic) that a molecule needs to possess to serve as a substrate for a transport protein significantly facilitates the design of pharmaceutical agents having improved cellular uptake (e.g., improved intestinal permeability).

Determination of the electronic and steric features that are correlated with complex internalization can be achieved in a variety of ways. In general, once a compound of a complex has been identified as a substrate for a transport protein, the compound and/or reporter of the complex are varied to obtain at least one variant complex, and more typically a library of variant complexes. Hence, certain variant complexes of libraries of variant complexes include compounds that are variants of one or more known substrates. A variant substrate is one in which certain features of the known substrate are maintained while other features are varied. The type of features that can be varied include, but are not limited to, electronic features (e.g., polarity and charge), steric features (e.g., size or position of substituents), chemical features (different functional groups) or stereochemical features. Thus, for example, the size of one or more substituents of the substrate can be varied, and/or a functional group altered, omitted or replaced.

Alternatively, a variant complex can include a compound from a complex known to be transported but a reporter that differs in some way from the reporter of the transported complex. Features of the reporter similar to those just described for the compound can be varied. In some instances, variant complexes simply involve placement of the same reporter at different sites on the substrate backbone. Of course, a library of variant complexes in which both compound and reporter are varied can be prepared. The libraries of variant complexes prepared from complexes showing activity with a transport protein are referred to as focused libraries.

Once a variant complex or population thereof has been generated, the complex(es) can be rescreened against the transport protein of interest. This process can be repeated in iterative fashion for as many times as desired, but preferably until the information necessary to infer structure-activity relationships is obtained. By characterizing the various compounds that are identified as substrates of a transport protein, certain features of the compounds emerge as key elements that correlate with activity. As indicated supra, such information can be used to provide valuable insight in the design of substrate-drug conjugates that can be readily taken up by transport proteins. Example 4 illustrates in further detail how sub-libraries can be generated from an active compound to obtain SAR information.

III. Screening DNA Libraries to Identify Transport Proteins

In other methods the goal is to clone hitherto unknown transport protein(s) of a known substrate. In such methods, a complex bearing the known substrate is contacted with a populations of cells transformed with a library of DNA segments encoding different candidate transport proteins. Cells binding to, internalizing or passing through complexes are isolated and cloned DNA segments are isolated therefrom and characterized, (e.g., by sequencing). With or without characterization, the DNA segments can be transformed into fresh cells for a secondary screen with the same compound.

In other methods, the goal is to clone new transport proteins regardless of the specific substrate. Such methods are performed by contacting a library of complexes bearing different compounds with a population of cells transformed with a library of DNA segments encoding different potential transport proteins. Cells binding to, internalizing or passing through a complex are isolated and DNA segments from these cells characterized. These DNA segments can then be retransformed into fresh cells. These cells, either as individual clones or as a mixed population, can then be rescreened against the original library of complexes to identify compounds that are ligands to each cloned transport protein.

IV. Alternative and Secondary Screening Methods

For complexes bearing compounds identified as binding to a cell but not being internalized or passing through the cell, a secondary screen is needed to determine whether the compound either agonizes or antagonizes transport of a substrate for a transport protein. An agonist screen can be performed using complexes that further comprise the compound being tested for agonism as well as a known or candidate substrate compound and a reporter. Complexes internalizing or passing through cells are isolated. Then a further screen is performed, optionally in a competition format, to compare the rate or extent of uptake or passage through a cell of a complex bearing a substrate and reporter, versus a complex bearing the substrate and a potential agonist and a reporter. A greater rate or extent of uptake or passage by the cell of the latter complex indicates that the potential agonist does indeed have agonist activity.

An inhibitor screen can be performed by incubating a complex comprising a known substrate for a transporter protein and a reporter with a population of cells bearing the transport protein in the presence and absence of the potential inhibitor and determining whether there is any decrease in rate or extent of uptake or passage when the inhibitor is present.

V. Multiplexed Methods

The screening methods disclosed herein can be conducted in a multiplex format in which multiple different cells expressing different transporter proteins and/or multiple different complexes, each having a different compound, are screened within a single reaction vessel (e.g., a single well of a multi-well plate). The different cells within a reaction vessel can be distinguished in a variety of ways. A simple multiplexed situation is one in which control cells (e.g., cells failing to express the transporter of interest) are assayed together with test cells that express the transport protein of interest. The test cells and control cells can potentially be distinguished if complexes are internalized within one group of cells but not the others as evidenced by signal coming from one group but not another group of cells. It can be inferred in this situation, that those cells from which no signal is detected are control cells. This can be confirmed using one of the methods that follow.

If the different cells are selected to have characteristic morphologies, then the different cells can simply be distinguished on the basis of different morphological characteristics. Alternatively, or in addition, different cells in a multiplex assay can be distinguished by differentially staining the cells. If the cells express different cell surface antigens that can be differentially stained, then all of the various cells can be stained together by adding the various dyes to a single reaction vessel. More typically, the cells are differentially stained in separate reaction vessels and then combined for the multiplex assay. Another option is to use cells that express different cell-surface markers to provide a basis for discriminating between cells. Such markers can be endogenous or exogenous. For example, different cells can be engineered to express different epitopes that can be selectively stained with labeled antibodies, with antibodies for different epitopes bearing different labels.

Different complexes within a reaction vessel can be distinguished by differentially labeling the various complexes. For example, different complexes can be labeled with different fluorophores that have different emission maxima. Alternatively, the complexes can bear different radioisotopes. A variety of other labels can be similarly utilized including, but not limited to, mass labels, luminescent labels, chromophores, spin labels, and substrates for different enzymes. A mass label refers to a compound or moiety capable of generating a distinctive mass fragment that can be detected using various size-based separation techniques (e.g., mass spectroscopy).

Although the foregoing methods facilitate a rapid and unambiguous means to sort out which cell or complex has activity, it is not necessary to use cells and/or complexes that are distinguishable from one another to conduct multiplex assays. For example, multiplexed assays can be conducted in which cells expressing different transporters are not distinguishable; a signal in a reaction vessel (e.g., well of a multi-well plate) indicates that the complex(es) in that reaction vessel are substrates for one or more of the transport proteins expressed by the cells. A second stage assay can then be conducted in which the different cells in the active reaction vessels are separately assayed to determine the specificity of the compounds. Likewise, multiplexed assays can be performed with multiple different complexes that are not differentially labeled. In this instance, a reaction vessel exhibiting activity is an indication that at least one of the complexes added to that particular reaction vessel has activity. The specific complex(es) responsible for the observed activity can be identified in a second screen in which the complexes are individually assayed.

Such approaches are not unduly burdensome as the vast majority of reaction vessels in a screen typically will not show activity. It is usually only necessary to deconvolute which cell and/or complex is active in a relatively small number of reaction vessels. These approaches also avoid the expense and complexity of using differentially labeled complexes and different cell types.

VI. Transcytosis Methods

Some methods are particularly adapted to screen for proteins that direct the transcellular movement (transcytosis) of complexes from the apical side of a cell to the baso-lateral side of a polarized cell. Polarized cells are present in many tissues. In all epithelial layers, the layers of cells separating the body from the outside world, the cells are polarized. Epithelial cell layers are characterized by the presence of tight junctions that form a very effective seal between all the cells of the layer. It is this seal that divides the cells into an apical (outside) and a basal (inside) surface. The areas between the cells on the inside side are lateral; hence, the entire inside surface of the epithelial cell is known as the "baso-lateral"

surface. The cytoskeletal structure, which is connected to the sites of the tight junctions, serves as an internal indicator of the orientation of the cell, and provides a signal to guide the proteins and organelles to their appropriate location in the polarized cell.

Figure 3:
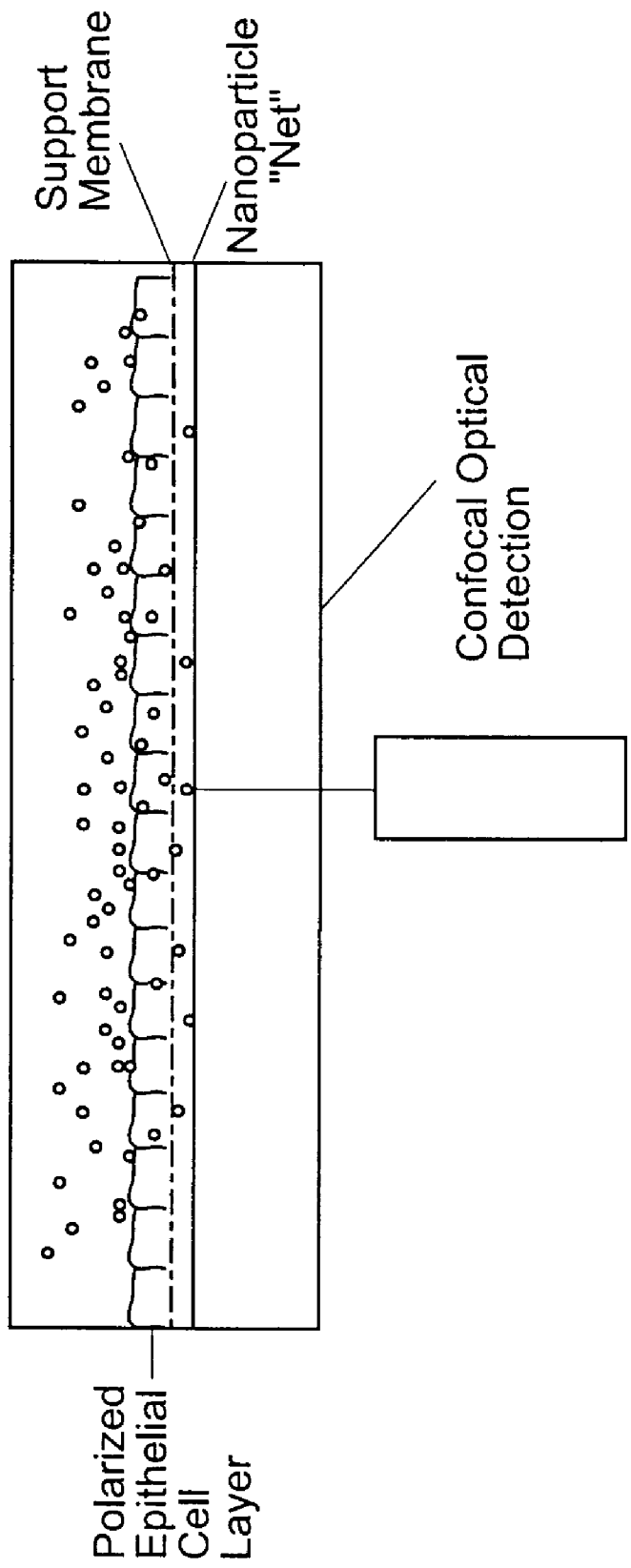
FIG. 3 illustrates a two-membrane system (a "transwell system") for detecting the movement of substrates through a layer of polarized cells by transcytosis.

In some such methods, a population of polarized cells (e.g., CaCo-2, HCT-8, T84, HT29 and MDCK) is grown on a first membrane of what is typically a two membrane system (see FIG. 3). The cells can be natural cells or cells transfected with DNA encoding potential transport proteins as described above. The first membrane or upper membrane is a porous membrane that includes pores that are larger than the complexes being screened. A monolayer of polarized cells is positioned on the upper membrane. A second or lower porous membrane is positioned under the first membrane and is structured to retain any complexes capable of traveling through the polarized cells and through the pores in the upper membrane.

In those cases where the movement of the complexes through cells and membranes are monitored by imaging from below, the second membrane is chosen to be optically transparent. The preferred membranes in this case are polyester in composition, and are available from Corning Costar. In those cases where the process is monitored by imaging from above, the following arrangement is preferred. Any of the commercial transwell plate configurations can be used, depending on the particular assay, having from 6 to 24 or more wells, each well having a membrane of 24 to 6.5 mm dia. The membrane chosen for the transwell is a large pore (3 um) transparent (polyester, 10 um thickness) type upon which the layer of epithelial cells are grown at a density of ~$10^6$ cells/$cm^2$ at confluence. Below this cell support membrane is suspended a second membrane constructed of polycarbonate with small pores (100 nm or less, 10 um thickness). The small pore size of the lower membrane is selected to provide a barrier to the further passage of particles larger than 100 nm. The second membrane is usually placed immediately below the primary cell support membrane, and the two membranes can be placed in contact with one another. This arrangement results in the accurate immobilization of particles immediately below the cell(s) through which they have passed.

An alternative method accurately to immobilize the particles is by the use of a thin gel matrix underlying the cell support membrane. A layer of agarose approximately 1 mm thick is poured on an optically transparent plastic plate. Before the agarose solidifies, the transwell device is lowered into the agarose to form an intimate contact between membrane and agarose. Occasionally, it is necessary to feed the wells from below or from both above and below. In this situation, a thin layer of agarose can be poured directly on the bottom surface of the membrane of an inverted transwell insert. A supporting mesh, such as fine nylon grid with openings ~1 mm across is placed across the gel to retain it in place once the transwell is returned to the upright position. When the agarose has gelled, the transwell is placed suspended in the receiving wells as usual. Both of these arrangements allow imaging from below with any of the usual cell support membrane types (e.g., polyester, polycarbonate, or PFTE), or from above if a transparent cell support membrane is used (polyester or PFTE).

A complex or, more typically, a library of complexes is contacted with the cell monolayer. The location of complexes that pass through the cell layer can be detected by any of a variety of optical methods. The second membrane immobilizes the complexes in the vicinity of the cell(s) expressing the cDNA that promotes the transcytosis of a complex, thus enabling the selection of cells expressing a protein capable of directing the transcytosis of at least some compounds. The cDNA located within such cells can then be used to identify the transport protein encoded by the gene.

To determine the test compounds in the library that induce transcytosis, cells identified as promoting transcytosis are picked and clonally expanded. The various members of the test compound library are exposed (sequentially) to each of the expanded clones in a transwell format similar to that just described for the expression library. Each clone transports those complexes that belong to a single family, such complexes are recovered from the bottom compartment of the transwell. Complexes that are not transported are removed from the top compartment of the transwell and placed on the next clone of cells, and the process repeated. At the end of this process, the pool of complexes recovered from below each cell clone layer represents a population enriched for test compounds that are able to direct the transcytosis of an attached particle. This can be a single compound or a group of related (or even non-related) test compounds that bind to the specific transport protein that has been cloned and over-expressed by the corresponding clones. By virtue of this enrichment, the test compound can be more easily and reliably identified by techniques described below.

VII. Libraries of Complexes

A. General

Each complex in such libraries typically contains a compound and a reporter capable of generating a detectable signal, preferably optical. The compound varies between complexes whereas the reporter is typically the same in different complexes, although reporters can vary as described supra. In some libraries, the compound and reporter are linked directly to each other by a chemical bond. Other libraries further comprise a support. The support can be a solid support, such as a bead or other particle. The support can also be a molecular scaffold or linker that holds the compound and reporter together. In such arrangements, both compound and reporter can be linked to the support. Alternatively, the compound can be linked to the support and the reporter to the compound or vice versa. Some complexes further comprises a tag encoding at least one step in synthesis of a compound present in the same complex as the tag. The tag is useful because typically its structure can more readily be determined or "decoded" than can the structure of the test compound itself, thus providing a useful way to identify the test compound attached to the bead. The tag can be attached to the support directly, via a linker, or via the compound or reporter.

The compound present in such complexes can be from random libraries, combinatorial libraries, libraries of variants of a known substrate, natural product libraries. Other suitable types of compound to be included in random libraries include, for example, polypeptides, oligonucleotides, β-lactams and other heterocyclic compounds, bile acids, oligo N-substituted glycines, polycarbamates, oligosaccharides, and lipids.

B. Libraries Constructed on a Support

1. General Structure

The different components or elements of the library can be organized in a variety of different arrangements. For example, the test compound, reporter and tag (if present), can all separately be attached to the support. Alternatively, various elements of the library can be joined together. For example, the reporter can be attached to the test compound or the tag. In such arrangements, either the reporter, test compound or tag can be the component that is directly attached to the support. Thus, the following arrangements are possible: -test compound-reporter; -tag-reporter; -reporter-test compound; and -reporter-tag (the element listed first is the element attached to the support). When different elements are connected, they can be directly connected or connected through a linker. Similarly, in some instances, rather than directly connecting an element to the support, the element is attached to the support via a linker.

2. Supports

The support can be made of a variety of materials, so long as the material is compatible with the chemistries that occur during the synthesis and/or attachment of the test compound, reporter and/or tag. Examples of materials that can be used include glass, latex, cross-linked polystyrene or similar polymers (including polyesters and cross-linked polyacrylamide), and gold or other colloidal metal particles. Such solid supports are derivatized with functional groups typical for solid state synthesis of the intended compounds (e.g., amino, carboxyl, hydroxyl, epoxide and sulfhydryl). Synthesis can also be performed on soluble polymers such as functionalized polyethylene glycols, that can be selectively precipitated from appropriate solvent systems (see, e.g., Gravert and Janda, 1997 *Chem. Rev.* 97:489-509).

The size of the support is chosen such that the support is sufficiently large that the test compound, reporter and/or tag can readily be attached thereto. However, the support should be small enough that it can be taken up by the transport process. In general, the solid support size is in the range of 1 nm to 100 microns in diameter; more typically, the supports range from less than 50 nm to about 10 microns in diameter. In certain applications the supports are only about 10 nm to about 100 nm in diameter. A more massive support of up to 1 mm in size can sometimes be used. MONOBEADS™ (Pharmacia Fine Chemicals AB, Uppsala Sweden) or their equivalent are one example of a commercially available support that can be used, although its size (10 μm) is on the upper end of the size range that is typically used.

The particular shape of the support is not critical, although typically the support is roughly spherical or bead-shaped. Nor is it critical whether the beads have similar sizes, shapes or composition. Beads can be formed as single beads or be linked to one or more other beads. When linked together, it is possible to synthesize different compounds on a set of beads. Such separation can be useful, for example, when the chemistries used to synthesize the test compound and the tag are significantly different.

Depending upon the type of support (for those instances in which the library includes a support), the support can naturally contain a variety of surface groups to facilitate attachment of the other elements of the library, such as hydrophilic, ionic or hydrophobic groups. For example, the support can include one or more chemical functional groups to facilitate attachment (e.g., hydroxyl, amino, carboxyl and sulfhydryl). Alternatively, the support can be derivatized to add such functional groups. For example, certain nanoparticles are formed of polystyrene and are derivatized to contain free amino groups.

Nanoparticles are one type of bead-like support that is useful with certain methods of the invention. Nanoparticles suitable for use in the invention can be prepared from a variety of materials, such as cross-linked polystyrene, polyesters and polyacrylamides or similar polymers. For use in vivo, biodegradable nanoparticles are particularly preferred. Such particles can be prepared from biocompatible monomers as homopolymers or as block copolymer materials. These include polyesters such as polylactic acid, polyglycolic acid, polyhydroxybutyric acid and polycaprolactone, polyanhydrides and polyphosphazenes. Frequently these particles are fabricated to contain an exterior surface comprising a hydrophilic polymer such as poly(alkylene glycol), poly(vinyl alcohol), polysaccharide or polypyrrolidine to resist uptake of the particles in vivo by the reticuloendothelial system. Such particles are described in U.S. Pat. Nos. 5,578,325 and 5,543,158.

The nanoparticles utilized with the methods described herein can be synthesized according to several known methods (See e.g., U.S. Pat. No. 5,578,325) or can be purchased from commercial suppliers such as Polysciences and Molecular Probes. The nanoparticles can be labeled with fluorescent molecules, and such nanoparticles are commercially available from Molecular Probes, for example. For example, nanoparticles can be prepared from block copolymers by emulsion/evaporation techniques using the pre-formed copolymer. The polymer, and optionally, a substrate to be encapsulated for delivery, are dissolved in an organic solvent and emulsified with an aqueous phase by vortexing and sonication (higher energy sources giving smaller particles). The solvent is evaporated and the nanoparticles collected by centrifugation. Typically, the nanoparticles include a functionalized group on the surface to facilitate the attachment of the test compound, reporter and tag.

Various other supports can also be utilized, including molecular scaffolds, liposomes, (see, e.g., Deshmuck, D. S., et al., Life Sci. 28:239-242 (1990); and Aramaki, Y., et al., Pharm. Res. 10:1228-1231 (1993)), protein cochleates (stable protein-phospholipid-calcium precipitates; see, e.g., Chen, et al., J. Contr. Rel 42:263-272 (1996)), and clathrate complexes. Dendrimers can also be used in some applications; these compounds can be synthesized to have precise shapes and sizes and to include a variety of surface groups (e.g., hydrophilic, ionic or hydrophobic) to facilitate attachment of the other elements of the library. (See, e.g., Tomalia, D. A., Angew. Chemie Int. Edn. 29:138-175 (1990); and Sakthivel, T., et al., Pharm. Res. (Suppl) 13:S-281 (1996)) (Each of the foregoing publications incorporated by reference in its entirety for all purposes.)

3. Encoding Tags

The encoding tags encode one or more reaction steps taken in synthesizing the test compound. For those test compounds wherein the synthesis yields a single product in high yield (e.g., peptide and oligonucleotide synthesis), the tag explicitly specifies one, and usually all, of the components of the test compound and its structure. In some situations, for example, when only a small number of monomer units of an oligomer are varied, it is not necessary to identify all the monomers utilized in the synthesis, but only those monomers which vary among the oligomers. For other syntheses that give variable yields and frequently multiple products (such as regio- and stereoisomeric structures), a mixture of compounds is sometimes obtained on each bead. In such instances, the encoding tag can not uniquely specify the chemical structure of the synthesize test compound. Instead, the encoding tag encodes the synthetic protocol (e.g., reagents and reaction conditions) by which a test compound in a library was prepared.

Encoding tags are selected to have a readily identifiable feature that is, for example, microscopically or otherwise distinguishable in shape, size, mass, charge, or emissions. This recognizable feature can arise from the spectral, chemical, electronic, or magnetic properties of the encoding tag, or from some combination of such properties. Through the use of encoding tags to record the synthesis pathway that each member of a chemical library has taken, the structure of any chemical in the library can be determined from the tag.

Nucleic acids and inert hydrocarbons are examples of the type of molecules that have utility as encoding tags in the present invention. Nucleic acids by virtue of the different bases and known chemistries regarding their attachment provide a natural and straightforward means for encoding the different synthetic steps. When decoding a nucleotide tag, several options are available. For example, the encoding tag can be read directly from the bead by sequencing or hybridization. Alternatively, or in addition, a nucleic acid tag can be amplified (e.g., by PCR) to facilitate identification. Hydrocarbons provide another useful option, because their identity can readily be determined by a variety of well-known chromatographic techniques, for example, GC and GC/MS. Other options are described in Ohlmeyer et al (*Proc. Natl. Acad. Sci. USA* 1993, 90, 10922-26 and WO 94/08051, each of which is incorporated herein by reference for all purposes.

The time at which the encoding tag is attached to the support is not critical. For example, an encoding tag can be attached immediately before, during, or after a round of monomer addition to compounds or other reaction, so long as such timing is compatible with the type of tag, modes of attachment, and the chemistries involved in preparing the test compound. The necessary encoding of the synthesis steps can be achieved using a single or multiple tags.

C. Synthesizing Test Compound

1. General

Libraries of compounds are usually synthesized by solid phase chemistry on particle. However, solution-phase library synthesis can also be useful. Strategies for combinatorial synthesis are described by Dolle and Nelson, *J. Combinatorial Chemistry* 1. 235-282 (1999)) (incorporated by reference in its entirety for all purposes). Synthesis is typically performed in a cyclic fashion with a different monomer or other component being added in each round of synthesis. Some methods are performed by successively fractionating an initial pool. For example, a first round of synthesis is performed on all supports. The supports are then divided into two pools and separate synthesis reactions are performed on each pool. The two pools are then further divided, each into a further two pools and so forth. Other methods employ both splitting and repooling. For example, after an initial round of synthesis, a pool of compounds is split into two for separate syntheses in a second round. Thereafter, aliquots from the separate pools are recombined for a third round of synthesis. Split and pool methods result in a pool of mixed compounds. These methods are particularly amenable for tagging as described in more detail below. The size of libraries generated by such methods can vary from 2 different compounds to $10^2$, $10^4$, $10^6$, $10^8$, $10^{10}$, $10^{12}$ or $10^{15}$, or any range therebetween.

Other components of a complex, such as the reporter, can be added before, after or during synthesis of compounds. Typically, reporter is added after compounds have been synthesized. In some methods, complexes are used as is. In other methods, compounds are cleaved from supports before use. In these methods, the reporter is attached directly or through a linker to the complexes, and such attachment can occur before or after synthesis of compounds.

In some instances, the various library elements are connected to one another by linkers. The linkers typically are bifunctional (i.e., the linker contains a functional group at each end that is reactive with groups located on the element to which the linker is to be attached); the functional groups at each end can be the same or different. Examples of suitable linkers include straight or branched-chain carbon linkers, heterocyclic linkers and peptide linkers. Exemplary linkers that can be employed in the present invention are available from Pierce Chemical Company in Rockford, Ill. and are described in EPA 188,256; U.S. Pat. Nos. 4,671,958; 4,659, 839; 4,414,148; 4,699,784; 4,680,338, 4,569,789 and 4,590, 071, Eggenweiler, H. M, *Pharmaceutical agent Discovery Today* 1998, 3, 552.

The choice of linker depends on whether the linker is intended to remain permanently in place or is intended to be cleaved before or during use. For cleavage prior to use, NVOC (6-nitroveratryloxycarbonyl) linkers and other NVOC-related linkers are examples of suitable photochemical linkers (see, e.g., WO 90/15070 and WO 92/10092), as are nucleic acids with one or more restriction sites, or peptides with protease cleavage sites (see, e.g., U.S. Pat. No. 5,382, 513). For cleavage during use, one selects a linker that is spontaneously cleaved under the conditions of the relevant assay (usually a physiological buffer). Such a linker should be stable under the conditions in which the test compound, reporter and/or tag, are attached to the beads, but should allow release of the test compound in the course of the assay.

In Example 15 below the concept of preparing propharmaceutical agent derivatives equipped with a fluorescent reporter moiety to facilitate assay of intestinal absorption (or cellular uptake) is exemplified. In the classical concept of the propharmaceutical agent, the promoiety is cleaved from the active pharmaceutical agent entity by enzymatic and/or chemical means. A wide variety of cleavable linkages are available depending on the nature of the functionality available in the pharmaceutical agent molecule. Examples of cleavable linkages include, for example, esters of simple alcohols or phenols, (acyloxy)alkyl esters, amides, O-hydroxamates, esters of simple or functionalized aliphatic carboxylic acids, esters of amino acids, esters of carbamic acids, esters of derivatized phosphoric acids, (alkyloxycarbonyloxy)alkyl ethers, (acyloxy)alkyl ethers, amides formed from simple or functionalized acyl groups, amides cleaved by intramolecular cyclization, alkyl carbamates, N-Mannich bases and N-(acyloxy)alkyl derivatives.

2. Synthesis of Encoded Libraries

Preparation of encoded libraries is described in a variety of publications including Needels, et al. *Proc. Natl. Acad. Sci. USA* 1993, 90, 10700; Ni, et al *J. Med. Chem.* 1996, 39, 1601, WO 95/12608, WO 93/06121, WO 94/08051, WO 95/35503 and WO 95/30642 (each of which is incorporated by reference in its entirety for all purposes). Methods for synthesizing encoded libraries typically involve a random combinatorial approach and the chemical and/or enzymatic assembly of monomer units. For example, the method typically includes steps of: (a) apportioning a plurality of solid supports among a plurality of reaction vessels; (b) coupling to the supports in each reaction vessel a first monomer and a first tag using different first monomer and tag combinations in each different reaction vessel; (c) pooling the supports; (d) apportioning the supports among a plurality of reaction vessels; (e) coupling to the first monomer a second monomer and coupling to either the solid support or to the first tag a second tag using different second monomer and second tag combinations in each different reaction vessel; and optionally repeating the coupling and apportioning steps with different tags and different monomers one to twenty or more times. The monomer set can be expanded or contracted from step to step; or the monomer set could be changed completely for the next step (e.g., amino acids in one step, nucleosides in another step, carbohydrates in another step). A monomer unit for peptide synthesis, for example, can include single amino acids or larger peptide units, or both.

VIII. Cells

A. General

Since the assays described herein involve screening for substrates of transport systems and/or transport proteins, the cells should either have a naturally-occurring transport protein or be cells that are transfected with a vector containing a transport protein gene that are also capable of expressing the gene. Cells containing naturally-occurring transport proteins can be obtained from a variety of epithelial and endothelial cell types, including, for example: (a) cells from the mucosal surfaces of the nose, mouth, throat, lung, intestine, genitals and urethra; (b) cells lining the eye, the deep ear, and secretory structures such as the mammary, salivary and tear ducts; and (c) outer skin and sweat glands. Suitable cells can also be obtained from certain endothelial cell layers, as well, such as those of the capillary endothelial cells forming the blood/brain barrier for example. For expression of a transfected DNA segments encoding transport proteins, cell lines typically used in genetic engineering can be used, with mammalian cell lines being preferred (e.g., CHO, COS, HeLa, MDCK, VERO, HEK, CaCo-2, HCT-8, T84, HT29, and 3T3).

Transfected DNA segments can encode previously cloned transport proteins, or can be libraries encoding potential transport proteins. Such libraries are typically obtained from the natural endothelial and epithelial tissue types identified above. The libraries are preferably obtained from human cells. DNA libraries are typically prepared as cDNA libraries although genomic or minigene libraries can also be used.

DNA segments are typically expressed as components of expression cassettes. Such cassettes also include one or more control sequences for the expression of the cDNA, such as a promoter, ribosome binding sites, and transcription termination sites for example. The promoter can be inducible (e.g., heat shock protein or MT promoter or a constitutive promoter, typically a strong promoter (e.g., SRα). Regulated promoters can be advantageous because the host cells can be grown to high densities before expression of the transport protein is induced. High level expression of heterologous proteins slows cell growth in some situations.

Commonly used prokaryotic control sequences include promoters for transcription initiation, optionally with an operator, along with ribosome binding site sequences, include such commonly used promoters as the beta-lactamase (penicillinase) and lactose (lac) promoter systems (Change et al. (1977) *Nature* 198: 1056), the tryptophan (trp) promoter system (Goeddel et al. (1980) *Nucleic Acids Res.* 8: 4057), the tac promoter (DeBoer et al. (1983) *Proc. Natl. Acad. Sci. U.S.A.* 80:21-25); and the lambda-derived $P_L$ promoter and N-gene ribosome binding site (Shimatake et al. (1981) *Nature* 292: 128).

For expression of a transport protein in yeast, exemplary promoters include GAL1-10 (Johnson and Davies (1984) *Mol. Cell. Biol.* 4:1440-1448) ADH2 (Russell et al. (1983) *J. Biol. Chem.* 258:2674-2682), PHO5 (*EMBO J.* (1982) 6:675-680), and MFα (Herskowitz and Oshima (1982) in *The Molecular Biology of the Yeast Saccharomyces* (eds. Strathern, Jones, and Broach) Cold Spring Harbor Lab., Cold Spring Harbor, N.Y., pp. 181-209). Another suitable promoter for use in yeast is the ADH2/GAPDH hybrid promoter as described in Cousens et al., *Gene* 61:265-275 (1987).

For expression of transport proteins in mammalian cells, exemplary promoters include SRα, CMV promoter (Miller, et al., *BioTechniques* 7:980), SV40 promoter (de la Luma, et al., (1998) *Gene* 62:121), RSV promoter (Yates, et al, (1985) *Nature* 313:812), MMTV promoter (Lee, et al., (1981) *Nature* 294:228). Expression in mammalian cells can be achieved, for example, using a variety of commonly available plasmids, including pSV2, pBC12BI, and p91023, pCDNA series, pCMV1, pMAMneo, as well as lytic virus vectors (e.g., vaccinia virus, adeno virus), episomal virus vectors (e.g., bovine papillomavirus), and retroviral vectors (e.g., murine retroviruses).

For expression of the polypeptides in insect cells a suitable promoter is from the baculovirus *Autographa Californica* nuclear polyhedrosis virus (NcMNPV) (Kitts, et al., (1993) *Nucleic Acids Research* 18:5667).

Construction of suitable vectors containing one or more of the above listed components uses methods described by e.g., Berger and Kimmel, *Guide to Molecular Cloning Techniques, Methods in Enzymology*, Volume 152, Academic Press, Inc., San Diego, Calif. (Berger); and Current Protocols in Molecular Biology, F. M. Ausubel et al., eds., *Current Protocols*, a joint venture between Greene Publishing Associates, Inc. and John Wiley & Sons, Inc., (1998 Supplement) (Ausubel).

IX. Detection Options

Complexes fall into three general classes. Complexes that simply do not interact with the target transport protein at all, those that bind to the surface of the cell and either interfere with binding of a substrate to the transport protein or bind to the transporter but are not internalized (inhibitors), and finally, complexes that are transported into the cell through the activity of the transport protein. Various detection schemes can be utilized to detect and distinguish between these different situations.

A. Detecting Binding of Complexes to Cell Membrane

External binding of complexes at the cell membrane is typically detected using a reporter that generates a signal directly (i.e., a label), usually an optical signal. Examples of suitable labels include a fluorophore, a chromophore, a radioisotope, a magnetic particle, a mass label, a spin label, a luminescent label and an electron dense agent. Examples of fluorescently labeled substrates are discussed in e.g., Kramer et al, *J. Biol. Chem.* 1994, 269: 10621; Mills et al, *Biochim. Biophys. Acta* 1992, 1126: 35) Börner et al, *Eur. J. Biochem.* 1998, 255: 698), Dieck et al., *Glia,* 1999, 25: 10; Otto et al, *Am. J. Physiol.* 1996, 271, C210).

The detector used varies according to the type of signal generated. When the label emits light, a variety of optical means can be utilized including, for example, confocal microscopy, charge coupled devices (CCD) and a variety of commercially available photomultiplier tube-based instruments. In general, such devices provide sufficient resolution to distinguish between label located within and outside a cell. Binding can also be detected by FACS methods. Some fluorophores give a different signal from outside and inside a cell allowing distinction between compounds that are bound to a cell and compounds that are within a cell.

B. Detecting Internalization of a Complex

1. General

Internalization of a complex can be detected by detecting a signal from a reporter (e.g., one of the foregoing labels) within a cell. It can be difficult, however, with conventional detection schemes to distinguish between labeled compounds that are effectively transported inside the cell from compounds that are not transported but nevertheless can still bind the transporter. These latter compounds (typically transporter inhibitors) are found bound to the outside of transporter-expressing cells. A variety of methods can be employed for detecting internalized substrates without detecting surface-bound ligands, or to at least selectively detect internalized substrate rather than surface-bound compounds. Selective or preferential detection means that at least 70%, more typically at least 80% and most typically at least 90% of the signal detected arises from internalized complexes compared to signal arising from complexes bound to the cell surface. To score specifically for uptake (as opposed to surface binding), several strategies are available and are discussed below.

2. Distinguishing Between Substrate and Inhibitor without Conditional Reporters

Confocal Imaging Confocal: imaging provides sufficient spatial resolution directly to distinguish between fluorescence on a cell surface and fluorescence within a cell. Optionally, the movement of a complex is monitored over time to determine if it moves into a cell. In such an approach, a monolayer of cells, generally polarized cells, is contacted with a library of complexes. Each complex bears an optically detectable reporter, such as a fluorescent compound, and the complexes are allowed to settle on the cell layer. The complexes are imaged (typically from above) with confocal optics, and the behavior of the complexes tracked over time. Confocal imaging allows differentiation between those complexes that have been internalized by the cells and those remaining on the surface of the optically deep layer of cells.

Cell Stripping and Cell Quenching: In another variation, the cells are stripped of complexes bound at the surface, or treated so as to disable the fluorophores that remain outside the cells by leaving the cells in wash buffer or washing the cells several times. In yet another method, the cells are analyzed in a solution of quencher that cannot penetrate the cells. Hence, the fluorescence of complexes bound to the surface is quenched, while internalized complexes fluoresce intensely.

2. Distinguishing Between Substrate and Inhibitor with Conditional Reporters

A powerful way of screening for bona fide transporter substrates is to incorporate conditional reporter groups into potential substrate molecules. The conditional reporter is a moiety that preferentially produces a readily detectable signal upon uptake by a transporter-expressing cell. In some instances, the conditional moiety can act without having to be cleaved from the complex; in other instances the conditional moiety must be chemically or enzymatically cleaved before it can generate a signal. Several such approaches are set forth below.

Reporter is a substrate for intracellular enzymatic activity: One general method for restricting signal generation to complexes that have been internalized within a cell is to make the reported event dependent on the action of some enzymatic activity that specifically resides intracellularly. This enzymatic activity may be provided by some exogenous expression cassette, or may be found endogenously within the transporter-expressing cell. Once a complex is taken up by a cell, the enzyme substrate (sometimes after being cleaved from the complex by intracellular enzymes) is metabolized by the enzyme expressed within the cell to generate an optical signal that indicates uptake of the complex into the cell. Light emission can be monitored by commercial PMT-based instruments or by CCD-based imaging systems.

A variety of enzymes are capable of metabolizing a reporter that includes an enzyme substrate to generate a readily detectable product. The intracelluar enzyme can be an endogenous enzyme or one that is expressed from an exogenous sequence introduced into the cells. Examples of suitable enzymes include proteases, nucleases, lipases, phosphatases, and various hydrolases, including sugar hydrolases and those capable of cleaving various other ester linkages. Specific examples include, for example, luciferase (de Whet et al., *Mol. Cell. Biol.* 7, 725-737 (1987)), chloramphenicol acetyl transferase, β-galactosidase (e.g., Kumar et al., *Bio/Technology* 10, 82-85 (1992)) and alkaline phosphatase (Toh et al., *Eur. J. Biochem.* 182, 231-238 (1989)) and β-glucuronidase.

The luciferin/luciferase substrate/enzyme pair provides a useful example of this general approach. A cell line that co-expresses the enzyme luciferase and a transport protein of interest is utilized. The preparation and selection of such cells is described in greater detail in Example 7. The natural substrate for luciferase, D-luciferin, can be conjugated to an appropriate transporter substrate via a labile bond (e.g., an ester, a carbonate or amide). The carboxyl and hydroxyl groups of luciferin provide useful functional groups for achieving such conjugation. Luciferin can be covalently attached to each test compound or to a support if the complex includes a support. Optionally, a spacer/linker is placed between the test compound and the luciferin or between the luciferin and the support. Example 7 describes the synthesis of certain luciferin-conjugated complexes that can be used to study transport by PEPT1 and the intestinal and liver bile acid transporters.

When a complex containing luciferin is taken into a cell, enzymes expressed within the cell (e.g., hydrolases) cleave luciferin from the complex. The liberated luciferin can then react with luciferase to generate an optical signal. Because the luciferin/luciferase system is very sensitive, only low amounts of complex need enter a cell in order to detect a signal. Thus, it is possible to detect substrates whose concentration is low relative to its $K_m$.

In some instances, the complex is modified through addition of a highly polar functionality to prevent passive uptake of the complex containing the enzyme substrate. To distinguish more clearly between passive uptake or uptake accompanying cell lysis, control cells transfected with the gene encoding the enzyme, but not the gene encoding the transport protein, are contacted with the complexes under test. The signal in the control cells is then compared with the signal from cells expressing the transport protein. A higher signal in the cells expressing the transport protein that is statistically significant is indicative of authentic transport activity.

Masked Reporters: Some conditional reporters contain "masked" moieties that generate only a weak signal until the masking group is removed by some intracellular enzymatic activity. For instance, the reporter can include a "masked" hydroxy-coumarin moiety that is weakly fluorescent until the masking group is cleaved away by an intracellular esterase, or other related activity. The resulting hydroxy-coumarin derivative is strongly fluorescent, thereby allowing transport of a complex into a cell to be read out using various fluorescent detectors (e.g., a fluorescence plate reader). The enzyme responsible for removing the masking group can be endogenously expressed within cells, or can be over-expressed so as to boost the signal from the transported substrate. Syntheses for certain conditionally fluorescent dipeptides that can be used to measure transport into a cell by the transport protein PEPT1 are set forth in Example 8 below.

Reporter Interaction with Intracellular Agent: Other conditional reporters are ones that do not require enzymatic activation but rather rely on the interaction between some intracellular agent or structure to produce a detectable signal. An example include nucleic acid-binding dyes (e.g., TOTO and YOYO from Molecular Probes), that are weakly fluorescent in the absence of DNA, but emit strongly upon binding to nucleic acids within the cell nucleus. Conjugation of transporter substrates to such dyes provides a convenient assay for transporter-dependent cellular uptake. This approach and other suitable dyes are discussed further in Example 6 infra.

Internally Quenched Reporters: In this approach, the complexes under investigation include a substrate, a fluorophore and a quencher. Outside a cell, the quencher can quench fluorescence from the fluorophore such that negligible signal is generated. In the cell, however, the conditions are sufficiently different such that the quencher is no longer able to efficiently quench fluorescence from the fluorophore. One typical mechanism involves cleavage (e.g., by an intracellular enzyme) of some element of the complex (e.g., an optional linker) that results in the separation of the fluorophore and quencher. Different types of quenchers can be utilized. Some quenchers absorb fluorescence emitted from the fluorophore (e.g., via fluorescence energy transfer (FRET) mechanisms). Other quenchers modify the electronic properties of the fluorophore so as to interfere with the ability of the fluorophore to emit fluorescence.

The quencher and fluorophore can be arranged in a variety of different orientations with respect to one another in a complex. For example, the fluorophore and quencher can be attached at different sites of the compound. In other instances, the complex also includes a linker. The linker can join the quencher or fluorophore; alternatively either the fluorophore or quencher is attached to the compound while the other is attached to the linker. As indicated above, the use of a labile linker susceptible to cleavage within a cell provides an effective way to separate the quencher from the fluorophore. The linker can include a cleavage site for any of a variety of intracellular enzymes, such as various hydrolases, including those capable of cleaving ester linkages.

Certain complexes that include a linker have the general form R—X—Y—Q, where X is the substrate for the transport protein of interest, R is the fluorophore, Q is the fluorescence quencher moiety and Y is a labile linker that typically is susceptible to cleavage by an intracellular enzyme. In the uncleaved complex, the quencher (Q) quenches fluorescence from the fluorophore (R). However, upon entry into a cell where the intracellular enzyme cleaves the labile linker, the quencher is released from the complex, thereby allowing detection of fluorescent emission from the fluorophore. Specifics regarding certain internally quenched complexes of this type are presented infra in Example 5.

In those instances in which donor/quencher dyes are utilized, a variety of such dyes can be selected from and are commercially available including, for example, CYA, FAM, R110, R6G, TAMRA, ROX, TET, JOE, HEX and ALEXA, which are available from suppliers such as Applied Biosystems Division of Perkin Elmer Corporation (Foster City, Calif.), Amersham Pharmacia Biotech (Piscataway, N.J.) and Molecular Probes, Inc. (Eugene, Oreg.). Further guidance regarding the selection of fluorophore and quencher pairs that can effectively be used with the methods of the present invention can be found, for example, in: *Fluorescence Spectroscopy* (Pesce et al., Eds.) Marcel Dekker, New York, (1971); White et al., *Fluorescence Analysis: A Practical Approach*, Marcel Dekker, New York, (1970); Berlman, *Handbook of Fluorescence Spectra of Aromatic Molecules*, 2$^{nd}$ ed., Academic Press, New York, (1971); Griffiths, *Colour and Constitution of Organic Molecules*, Academic Press, New York, (1976); *Indicators* (Bishop, Ed.). Pergamon Press, Oxford, 19723; and Haugland, *Handbook of Fluorescent Probes and Research Chemicals*, Molecular Probes, Eugene (1992).

Exemplary quenchers that disrupt the electronic properties of the fluorophore include acylated coumarins. In general, many aromatic fluorophores have an electron-pair containing heteroatom directly attached to a conjugated ring system. Acylation of these heteroatoms can frequently be used to block the fluorescence of the fluor by blocking the ability of the heteroatom to donate electrons into the ring system.

Reporter as a Bioactive Moiety. Certain other reporters include a bioactive molecule capable of triggering the formation of a detectable signal upon entry into a cell. For example, the complex can include a reporter capable of aggregating (e.g., dimerizing) intracellularly-expressed enzyme fragments, thereby activating an enzyme that reacts with a non-fluorescent substrate to generate a fluorescent signal. The reporter can also be an activator of a transcriptional promoter linked to a gene that expresses a protein that generates a signal. In certain methods, the promoter drives production of a reporter gene that is, as above, an enzyme capable of generating a signal (e.g., a fluorescent protein such as green fluorescent protein (GFP)). In other methods, the promoter drives expression of a cell surface marker that can be stained with a fluorescently-labeled ligand or antibody at the cell surface and then detected by FACS.

The reporter can also be an activator that, once inside the cell, induces, either recombinationally, transcriptionally or post-transcriptionally, a selectable marker conferring a growth advantage on the cell containing the complex. When the cell population is placed under selective pressure, those cells expressing the transport genes are capable of surviving and can be isolated from the other cells.

In another instances, the reporter is an agent that triggers a morphological change in the cell into which it is taken up either in uncleaved form or after being cleaved from the rest of the internalized complex. One such agent is one that inhibits various cytoskeleton components (e.g., cytocholasin). Other suitable agents include, but are not limited to, colchicine, latrunculin-A, taxol and nocodazole. Detection in this instance typically is by microscopy to detect the morphological change occasioned by entry of reporter into the cell.

3. Distinguishing Between an Authentic Substrate and Passive Diffusion

One approach for methods such as those just described in which the reporter for a complex includes a substrate for an intracellular enzyme, involves conducting a second set of parallel screens using control cells expressing the enzyme but not the transport protein. Incorporation of complex into the control cells provides a measure for uptake through mechanisms other than authentic transport activity, such as passive diffusion or cell lysis.

Another approach also utilizes one set of cells that express transport protein, and another set of cells that does not. These two groups of cells are differentially labeled (e.g., with fluorescent stains) so that the different cell types have different optical properties. Typically, the two cell types are mixed in near equal proportions and exposed to the complex(es) being tested. Using multi-color confocal microscopy, the two cell types can be distinguished and uptake separately monitored for each cell type. Thus, non-specific binding and passive diffusion due to a library complex can be distinguished from specific interaction with the transport protein. Commercial instruments capable of high resolution, high throughput confocal analysis of cells in multi-well plates are available (e.g., Cellomics, Praelux).

C. Detecting Transport Through a Cell

As described above, one method for detecting movement of a complex through a cell, such as via transcytosis for example, involves growing a monolayer of cells on a porous membrane support. A second membrane capable of immobilizing complexes that are transported through the cells and the first membrane is sometimes also used.

Movement of complexes through the layer of cells can be observed by direct optical observation, such as through the use of confocal microscopy, for example. The second membrane, if present, immobilizes the complex in the vicinity of the cell(s) expressing the cDNA that promote transcytosis. These active cells are then picked using e.g., micromanipulation techniques and the DNA segment located therein sequenced to determine the gene encoding a transport protein capable of transporting at least certain compounds.

Alternatively, movement of complexes through cells can be monitored using a reporter that is a substrate for an enzyme that is impregnated in a membrane supporting the cells. Localization of the signal "under" the cell layer by confocal microscopy identifies the cells expressing transport systems capable of transcellular transport. This assay can also be performed in the reverse format in which the reporter is the enzyme and substrate is impregnated in the membrane. The enzyme can be any of those described above in the section on detecting internalization.

In another approach, complexes bear a reporter that is an activator of a metabolic process in indicator cells. The indicator cells are then impregnated into a membrane supporting a cell monolayer. After passage of a complex through the monolayer, the reporter induces a metabolic event in the indicator cells that generates a signal in proximity to the cell(s) passing complex(es). Examples of suitable reporter include a bioactive compound that activates a cell surface receptor and a linked transcriptional promoter installed into the indicating layer of cells. The promoter drives a secondary reporter that can include, for example, an enzyme capable of generating a fluorescent signal, a fluorescent protein such as GFP, or a cell surface marker that can be stained by a fluorescently-labeled ligand or antibody at the cell surface for detection by FACS. Optical alignment of the active reporter cells with the polarized layer of library cells allows identification and recovery of the positive library cells in the layer above the reporters cells.

X. Steps Subsequent to Detection

Once a substrate of a transport process has been identified through one of the screening mechanisms described above, the identity of the test compound is determined according to methods described below. For screening methods in which a library of complexes is screened against cells expressing a known transport protein, the complexes yielding a positive result can be analyzed directly using the identification methods described below to determine the identity of the test compound.

If the screening methods involve screening a library of complexes against a population of cells expressing a cDNA library, those cells giving a positive signal can be identified as described above and then isolated from the other cells by hand picking, by various known micromanipulation techniques or by compartmentalizing the cell. The cDNA from positive cells is removed using standard techniques and typically amplified to facilitate the sequencing of the cDNA to identify a potential transport protein. For screens of this type, typically another round of screening is necessary to identify the test compounds in the complex library that are substrates of the transport protein expressed by the cells. In general this involves expanding positive clones and rescreening the compound library against each of the expanded clones according to the methods set forth herein. Determination of the structure of complexes that yield a positive signal is then performed by the decoding, deconvolution and direct structural methods described below.

Regardless of the screening methods, test compounds or cells that yield positive results in the initial round of screening can be rescreened in isolation to verify the authenticity of the apparent activity.

XI. Identifying and Synthesizing Positive Test Compound

Once a complex is identified through the screening methods set forth above, the test compound associated with transport activity can be identified through various methods. One approach is to directly determine the structure using standard chemical techniques such as mass spectrometry (MS), infrared spectroscopy (IR), high performance liquid chromatography (HPLC), nuclear magnetic resonance (NMR).

When the complex includes a tag the tags can be decoded according to conventional methods. For example, if the tags are nucleic acids, they can be decoded by PCR amplification and sequencing. Other types of tags can be decoded by, for example, mass spectrometry, FACS, gas chromatography or HPLC. The information obtained by decoding the tag identifies the compound (or component(s) thereof) originally from the same complex as the tag. Based on this information, a test compound associated with transport activity can be synthesized de novo. For example, if the compound is a peptide, it can be synthesized on a peptide synthesizer. If a substantial collection of test compounds are identified after an initial round of screening, the compounds can be resynthesized on supports and rescreened by reiteration of the methods described above.

XII. Additional Screens

A. Screening Substrates for Those Capable of Carrying Pharmaceutical Agent

1. Screening Methods

Screening libraries of potential transporter substrates conjugated with reporter moieties provides an efficient method for discovery of substrates that can also be conjugated with diverse substances such as pharmaceutical agents to confer substrate activity on such conjugates. Rather than directly developing a separate screen for uptake of each pharmaceutical agent of interest, the reporter can serve as a surrogate for the pharmaceutical agent during the preliminary screens. Essentially, the reporter serves as a place holder for the pharmaceutical agent. This approach has the advantage that uptake of a substrate bearing a reporter by the transport system is readily detected; whereas, a pharmaceutical agent coupled to a substrate often does not provide a readily detectable signal. The ability of the transporter to tolerate incorporation of some reporter moieties within a substrate motif suggests that conjugation of a fragment of a pharmaceutical agent having structural and chemical features that are at least somewhat similar to the reporter should generate a complex that is also recognized as a substrate by the transporter protein. Moreover, should a diversity of reporters be accepted when conjugated at a particular site within a substrate molecule, this indicates that the site is especially favorable for conjugation of a pharmaceutical agent.

Hence, once a substrate for a transport protein is identified, variant libraries such as described supra can be prepared in which different reporters are conjugated to the substrate and then the resulting complexes screened to determine whether activity of the substrate is retained. The type of different reporters attached to the substrate in the variant library can vary with regard to charge, size, isomeric form and other chemical or physical parameters. Alternatively, libraries can be generated in which the same reporter is simply positioned at different sites of the substrate backbone (see Example 4). As indicated above, substrates demonstrating the ability to retain activity with a wide range of reporter types suggest that the substrate is a candidate for the transport of a wide array of pharmaceutical agents.

Once the preliminary screens with various reporters has identified one or more candidate substrates, the pharmaceutical agent(s) of interest is (are) substituted for the reporter and the resulting substrate-pharmaceutical agent conjugates rescreened according to the methods disclosed herein. The pharmaceutical agents used to replace the reporter often are selected to be approximately isostructural and/or to have similar electronic characteristics with the reporters shown to be transported. Likewise, the pharmaceutical agent is positioned at the same sites(s) shown in the preliminary assays with reporters to correlate with transport. This process is illustrated further in Example 10 infra.

Various known transporters are attractive candidates for the development of substrate-drug conjugates developed according to the foregoing methods. For example, the development of substrates for the intestinal bile acid transporter (ASBT) is attractive because this transport protein is responsible for the absorption of large quantities of bile acids in through the ileum. In humans, approximately 20 g of free an conjugated bile acids are absorbed each day. Bile acids are synthesized in the liver and are secreted in the small intestine to facilitate absorption of lipophilic vitamins and cholesterol.

2. Detection of Transport for Complexes Bearing Pharmaceutical Agents

Complexes synthesized to include an agent (e.g., a drug) at the site at which a reporter was initially attached often require specialized methods for detecting cellular uptake as often the attached agent is not readily detectable. Various options are available to accomplish detection in such situations.

One detection approach is to utilize various analytical techniques to separate and detect substrate that is internalized within a cell. For example, LC/MS/MS (LC=liquid chromatography; MS=mass spectroscopy) can be utilized in such a manner. Test cells and control cells are contacted with the substrate/pharmaceutical agent conjugate for a sufficient length of time to allow uptake by the cells. The cells are then washed to remove substrate that has not been internalized, the cells lysed to release internalized substrate and the released substrate detected by LC/MS/MS (see Example 11). Other chromatographic and spectroscopic methods can be used individually or in combination to achieve similar detection as will be appreciated by those with skill in the art.

Figure 4:
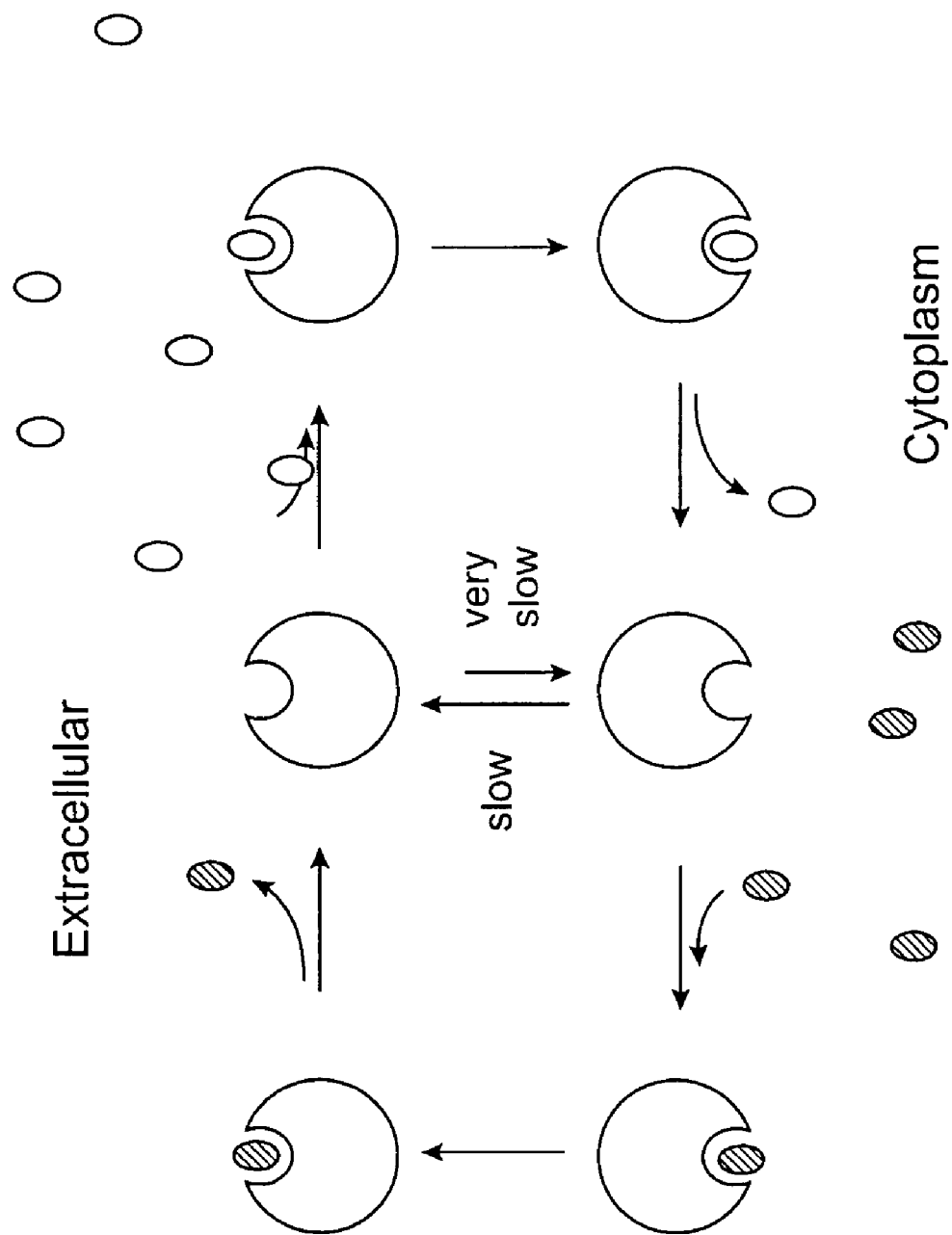
FIG. 4 is a schematic diagram illustrating the process of trans-stimulation, or the process of substrate-mediated efflux of labeled substrate from within the cell to the cell exterior.

Trans-stimulation assays can also be used to detect substrate uptake. The general theory of this method is illustrated in FIG. 4. As depicted in this figure, the method takes advantage of the fact that the flip-flop conformational change of a transport protein can exchange labeled substrates within a cell for unlabeled substrates outside the cell. Initially, cells expressing a transport protein of interest are contacted with a known labeled substrate (e.g., radiolabeled substrates) so that the cells become loaded with the labeled substrate. The cells are washed to remove non-internalized labeled substrate and then contacted with unlabeled test complexes. The efflux of labeled substrate is measured. In the case of radiolabeled substrates, such efflux can be detected by scintillation counting. Substrate activity of the test complex is indicated by accelerated efflux of the labeled substrate from the cell.

In the case of screens in which one is screening complexes wherein a drug has been substituted for the reporter, the test complex is the substrate-drug conjugate. The labeled known substrate loaded into the cells can be the same substrate conjugated to the drug or another known substrate. If the substrate-drug conjugate accelerates efflux of the labeled substrate from the cell, such activity indicates that the test substrate is able to transport the pharmaceutical agent into the cell. This approach is discussed further in Example 11.

It should be recognized that the LC/MS/MS and trans-stimulation assays just described are generally adaptable to high throughput screening assays for libraries of complexes that lack a reporter. Hence, the assays can be used to screen unlabeled compounds for potential activity with a transporter of interest. The methods, however, are not limited to simply screening complexes in which an agent has been substituted for a reporter but can be used generally to assay complexes lacking a reporter.

B. Competition Assays

With the above methods, a number of new substrates for specific transport proteins can be identified. Such newly identified substrates can then be utilized to conduct high throughput competition assays. In general, the method involves contacting a cell or multiple cells expressing a transport protein with a complex that includes a known substrate for the expressed transport protein and a reporter and detecting a signal generated by the reporter within the cell. In a parallel reaction, cells of the same type are contacted with the same amount and type of complex and also contacted with a test compound. Another signal is detected for the second set of cells and compared with that obtained for the first set of cells. Reduced signal for those cells contacted with the test compound relative to those cells not contacted with the test compound indicates that the test compound is a substrate or an inhibitor of the transport protein expressed by the cells. If desired, tests such as those described above can be performed to ascertain whether the test compound is a substrate or an inhibitor. The test compound used in the competition assays can be of virtually any chemical type. Use of a competition assay is detailed in Example 2 below.

IN Vivo Methods for Screening for Substrates of Transport Proteins

I. Initial Screening

A. General

The methods described above have focused on in vitro methods for screening for substrates of transport proteins and in vitro methods for identifying new transport proteins. However, the invention also provides a number of in vivo screening methods that can be used solely or in combination with in vitro methods to screen a library of complexes to identify new substrates for transport proteins. In general, the in vivo methods involve introducing a population of complexes into a body compartment in a test animal and then recovering and identifying the subset of introduced complexes transported through cells lining the body compartment into which the complexes were placed. More specifically, the screens typically involve monitoring a tissue or body fluid (e.g., the mesenteric blood and lymph circulation) for the presence of complexes that have entered the blood or lymph of the test animal.

B. Structure of Library Complexes

The structure of the library complexes introduced into the animal compartment have the same general structure of the complexes in the bead libraries discussed above. Hence, the library complexes typically include a support, a test compound, a reporter and an optional encoding tag (i.e., a tag encoding for the test compound). Similarly, the libraries are of the same chemical type and can be synthesized according to the methods set forth above. In some methods, the support is a nanoparticle. Libraries of soluble compounds not attached to supports can also be used. These also have the same composition, structure, and size attributes described earlier, as well as being synthesized as described above.

Typically, the reporter used in the in vivo screen methods is a capture tag that facilitates retrieval and concentration of the transported complexes from the blood and lymph circulatory system of the test animal. Examples of suitable capture tags include, biotin, magnetic particles associated with the library complex, haptens of high affinity antibodies, and high density metallic particles such as gold or tungsten. The complexes can also include a detection tag to further enhance the retrieval and detection process. As the name implies, detection tags are molecules that are readily identifiable and can be used to monitor the retrieval and concentration of transported complexes. Examples of such compounds include fluorescent molecules, amplifiable DNA molecules, enzymatic markers, and bioactive molecules.

C. Location at which Complexes Deposited

The complexes can be deposited into any body compartment that contains transport proteins capable of transporting a complex into a second body compartment, provided transported complexes can be retrieved from the second compartment. Typically, the complexes are placed into a body cavity wherein transported complexes are transported into the blood and lymph circulation system of the test animal. Thus, for example, the complexes can be deposited into the intestinal lumen of the test animal, and the transfer of the particles into blood and subsequently other organs can be monitored.

Another preferred application is the tracking of particle transported from the circulation, through the blood brain barrier and into the CNS compartment. In these methods, the particles are injected intravenously, and their appearance in the cerebral spinal fluid or the brain tissue is followed. CSF monitoring can be done periodically on an anesthetized animal. Analysis of particle transit into the tissues of the brain requires that the animals be anesthetized, the brain vasculature flushed by saline perfusion, and the tissue removed for homogenization prior to particle isolation. The particles are then isolated by physical capture techniques as described below for recovery from the blood.

D. Methods by which Complexes Deposited

In instances in which the complexes are deposited into the intestinal lumen, it is sometimes useful to close the intestine on either side of the site of deposit. This maneuver increases the residence time of the complexes in the relevant portion of the gut, thus allowing increased transport and ultimately more sensitive detection of transport.

E. Retrieving/Concentrating and Identifying Transported Complexes

As described above, the reporter (capture tag) and detection tags are used to filter, detect and concentrate transported complexes from the compartment into which the complexes are transported. In some instances, this involves retrieving and concentrating transported complexes from the large blood volume that perfuses the intestine.

Once the transported complexes have been retrieved and suitably concentrated, the identity of the test compound responsible for conferring transportability can be determined by any of the direct chemical analysis, decoding or deconvolution methods set forth above. Further details are also set forth is Example 16, below.

F. Animals

Essentially any animal can be used to conduct the in vivo screening tests described herein subject to regulations concerning test animals. For example, the screening tests can be performed with humans, monkeys, chimpanzees, horses, sheep, pigs, rabbits, dogs, cats, rats, and mice.

II. Variation

In some screening methods, the test compound library is supplied in large library-equivalent excess (i.e., there is a large number of copies of each member of the library, such as from about 1,000 to about 1,000,000 copies for example). However, in other respects, the method is as generally set forth above. Although in some instances the size of the library particles consists primarily of smaller particles (e.g., about 10 to 100 nm). Methods utilizing this approach enable many copies of each transported complex to be retrieved. In fact, the number of beads recovered with a given compound is a good indication of the effectiveness of the transport pathway taken by that compound, the affinity for the transported complex and/or the capacity of the transport protein.

Regardless of the particular in vivo method, the initial enrichment process can be repeated with the recovered complexes in the same or a different animal for additional enrichment (although typically at the expense of yield in complexes retrieved). If at the conclusion of multiple rounds of screening, there are only a relatively few remaining complexes, the identity of the test compound associated with each transported complex can be determined directly according to the methods described above, providing the final yield of complexes is sufficiently high.

Another screening option after in vivo enrichment, is to further enrich the pool of transported complexes according to one of the in vitro methods described herein. Since the in vivo screens are directed at identifying substrates that can be transported across a cell, further in vitro screening is typically performed using the bilayer transwell system described above which is a way to identify cells that are capable of transporting complexes through a cell monolayer. If such further screening is performed, initially a portion of the pool of complexes retrieved from the animal circulation is typically exposed to the transwell system, and cells transporting a complex identified, selected and each clonally expanded.

Next, the remaining complexes from the pool selected in the animal are exposed (sequentially) to each of the expanded clones in the same transwell format. Each clone passes complexes that belong to a single ligand family and these can be recovered from the bottom compartment of the transwell. The remaining complexes of the pool (those not transported) are removed from the top compartment of the transwell and placed on the next clone of cells, and so on. At the end of this process, the pool of complexes recovered from below each cell clone layer represents a population enriched for compounds able to direct the cellular transport (e.g., transcytosis) of an attached particle utilizing the transport protein expressed in the clone of cells the particle passed through. By virtue of this enrichment, the compound can be more easily and reliably identified by direct structural analysis, or by identification of a representative tag. In addition, this process maps or correlates the compound families to their corresponding transport protein.

In another variation, a series of separate pools of complexes are sequentially applied to a single animal, retaining the ability to determine which group of compounds each bead belongs to by "pool tagging". Each library or final pool (from the final synthesis step) is labeled with a distinguishable tag (e.g., fluorescence). Each library or pool can be administered to the intestinal loop or the intact intestine of the test animal, and the transported beads recovered by the methods described above. The library or pool from which the beads derive is determined by the pool tag associated with each bead. This method can be used sequentially as a means to deconvolute a library of compounds.

For example, one group of compounds having a certain structural characteristic is labeled with a fluorescent molecule that generates a first color; a second set of compounds having a different structural characteristic than the first set is labeled with a fluorescent molecule that generates a second color. Once the compounds that have passed through the cells have been recovered, it is possible from the relative amount of each colored compound to determine the relative number of each group of compounds that were capable of being transported through the cells. The group of compounds having the highest activity can then be further subdivided into subfamilies, each subfamily having a certain characteristic structure, and the process repeated as many times as desired. Each time the process is repeated it becomes possible to more closely identify what structural characteristics are associated with transport activity.

Pharmaceutical Compositions

Substrates for a transport protein identified according to one of the methods described above can be attached to an existing pharmaceutical agent to confer more efficient and/or more specific uptake on the pharmaceutical agent. The ability of substrate so attached to the pharmaceutical agent to transport the pharmaceutical agent can be confirmed according to the screening method described above.

I. Primary Components

Some pharmaceutical composition contain a ligand for a transport protein directly attached to a pharmaceutical agent or indirectly attached thereto via a linker. Optionally, the linker is cleavable. Other pharmaceutical compositions include a ligand of a transport protein, a pharmaceutical agent, and a nanoparticle. The nanoparticles are preferably from 50-200 nm in diameter. The nanoparticles provide an attachment point for the substrate and pharmaceutical agent, and can also protect the pharmaceutical agent by enclosing it non-covalently in a biodegradable particle. The pharmaceutical agent can be attached to the nanoparticle or located within it. The ligand is exposed on the exterior surface of the nanoparticles and is effective in promoting cellular uptake and/or transport of the nanoparticle through a cell. The ligand can be directly attached to the nanoparticle or attached via a linker. Typically, the ligand is effective in promoting uptake over at least 5, 10, 20, 50 or 90% of nanoparticles administered bearing the ligand and pharmaceutical agent. Typically, the ligand is a substrate of the transporter, such as a receptor for receptor mediated transcytosis. However, ligands that bind to a cellular molecule and thereby juxtapose a pharmaceutical agent in proximity to a suitable receptor can also be used.

The nanoparticles used in pharmaceutical compositions have the general composition, size, and shape as set forth above. The pharmaceutical agent attached to or located within the nanoparticle can vary widely provided it can be attached or encapsulated by the nanoparticle. For example, the pharmaceutical agent can be an antibacterial pharmaceutical agent, a antihypertensive pharmaceutical agent, a vasodilator, an antiviral pharmaceutical agent and an anticancer pharmaceutical agent. Ligands and pharmaceutical agents can be attached to nanoparticles by the same types of linkages discussed in synthesis of compound libraries.

II. Secondary Components

A. Additional Ligands

Some pharmaceutical compositions include a second ligand of a transport protein. In such compositions, typically one ligand is a substrate of a membrane bound transporter protein, and the other ligand binds to an exposed cellular molecule in proximity to the transporter protein For example, one ligand the can bind to a receptor on the cell surface and induce the formation of a pit to initiate the events that lead to internalization. The other ligand binds to a proximate cellular molecule.

Alternatively, one ligand is a substrate for a cell membrane bound transporter protein, and the other ligand binds to an intracellular transport protein that directs the basolateral trafficking of vesicles from the central sorting endosome. Binding of the first ligand results in internalization of the particle. In the absence of the second ligand, the particle is sometimes recycled to the same cell surface (e.g., the apical side) from which it originated rather than moved to the basolateral side. By selecting a second ligand that can direct basolateral trafficking in such a situation, the particle is transferred from the initially-bound receptor to another receptor and associated vesicle destined for the basolateral side of the cell.

In some pharmaceutical compositions, the second ligand is attached so that it be released from the nanoparticle in use. Such compositions are useful when the second ligand is needed to induce the internalization response, but is unable to do some unless released into the local environment to activate endocytosis. The first ligand, meanwhile, acts to retain the bead in the pit as it invaginates to form a transport vesicle.

B. Optional Agents within the Nanoparticle

Other components can be contained within or otherwise attached to nanoparticles. For example, nanoparticles can include a compound to inhibit the acidification of a vesicle enclosing the particle, thereby reducing or preventing damage to the pharmaceutical agent compound as it is transported in the vesicle. A similar result is obtained by placing a buffering compound in the nanoparticle. The buffering agent can be designed to remain in the bead, buffering only the interior of the bead itself, or can elute from the bead to buffer the vesicular compartment. In situations in which the bead is to be directed to the cytosol (and subsequently to other cellular compartment outside of the vesicular system), an agent causing lysis of the vesicle can be included within or attached to the nanoparticle. Suitable agents include adenovirus coat protein.

In some pharmaceutical compositions, nanoparticles are decorated on their outside with a substance that resists rapid clearance of particles by the reticuloendothelial system (RES). PEG is a suitable substance for this purpose (e.g. see Bocca et al, *Int. J. Pharm.* 1998, 175, 185). Example 6 below describes the use of commercially available amino-functionalized fluorescent nanoparticles for library synthesis by the split-pool method. Note that the bead surface is first coupled with a mixture of PEGylated carboxylic acid and a β-amino acid spacer. The β-amino acid serves as linker upon which the dipeptide is synthesized. The ratio of PEG to dipeptide on the nanoparticle surface can be varied as required.

Once a nanoparticle is released from the vesicle and exposed to the cytoplasm, additional targeting strategies can be employed to direct to the beads to the desired cellular compartments. For example, a short peptide motif known to target proteins and vesicles to certain cellular destinations can be attached to the nanoparticle. Examples of such basolateral targeting peptide motifs are known as "di-leucine" and "tyrosine-dependent type" (e.g. LeuLeu and TyrXXPhe, respectively) found in the cytoplasmic domains of certain basolaterally localized proteins such as LDL receptor, mannose 6-phosphate receptor, lysosomal acid phosphatase, and various viral proteins such as Influenza Virus hemaglutinin. (LeBorgne and Hayflick, *Curr Opin Cell Biol.* 1998, 10, 499-503; Kirchhuasen, et al. *Curr. Opin. Cell. Biol.* 1997, 9, 488-495; Jacob, et al, *J. Biol. Chem.* 1999, 274, 8061-8067).

III. Other Components and Delivery

The pharmaceutical compositions can also include, depending on the formulation desired, pharmaceutically-acceptable, non-toxic carriers of diluents, which are defined as vehicles commonly used to formulate pharmaceutical compositions for animal or human administration. The diluent is selected so as not to affect the biological activity of the combination. Examples of such diluents are distilled water, buffered water, physiological saline, PBS, Ringer's solution, dextrose solution, and Hank's solution. In addition, the pharmaceutical composition or formulation can also include other carriers, adjuvants, or non-toxic, nontherapeutic, non-immunogenic stabilizers, excipients and the like. The compositions can also include additional substances to approximate physiological conditions, such as pH adjusting and buffering agents, toxicity adjusting agents, wetting agents, detergents and the like (see Remington's Pharmaceutical Sciences, Mace Publishing Company, Philadelphia, Pa., 17th ed. (1985). For a brief review of methods for pharmaceutical agent delivery, see, Langer, Science 249:1527-1533 (1990), each incorporated by reference in their entirety).

The compositions can be administered for prophylactic and/or therapeutic treatments. The pharmaceutical agent attached to or encapsulated by the nanoparticle in the pharmaceutical compositions is typically is present in a therapeutic amount, which is an amount sufficient to remedy a disease state or symptoms, or otherwise prevent, hinder, retard, or reverse the progression of disease or any other undesirable symptoms in any way whatsoever. The concentration of the pharmaceutical agent in the pharmaceutical composition can vary widely, i.e., from less than about 0.1% by weight, usually being at least about 1% by weight, to as much as 20% by weight or more.

In therapeutic applications, compositions are administered to a patient already suffering from a disease, as just described, in an amount sufficient to cure or at least partially arrest the symptoms of the disease and its complications. An appropriate dosage of the pharmaceutical composition or polypeptide of the invention is readily determined according to any one of several well-established protocols. For example, animal studies (e.g., mice, rats) are commonly used to determine the maximal tolerable dose of the bioactive agent per kilogram of weight. In general, at least one of the animal species tested is mammalian. The results from the animal studies can be extrapolated to determine doses for use in other species, such as humans for example. An effective dose also depends on the nature and severity of the disease or condition, and on the general state of the patient's health.

In prophylactic applications, compositions containing the compounds of the invention are administered to a patient susceptible to or otherwise at risk of a particular disease or infection. Such an amount is defined to be a "prophylactically effective" amount or dose. In this use, the precise amounts again depends on the patient's state of health and weight.

The pharmaceutical compositions can be administered in a variety of different ways. Examples include administering a composition containing a pharmaceutically acceptable carrier via oral, intranasal, rectal, topical, intraperitoneal, intravenous, intramuscular, subcutaneous, subdermal, transdermal, intrathecal, and intracranial methods. The route of administration depends on the substrate present in composition. For example, substrates for ileal transport proteins are useful for oral administration.

For oral administration, the active ingredient can be administered in solid dosage forms, such as capsules, tablets, and powders, or in liquid dosage forms, such as elixirs, syrups, and suspensions. The active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate. Examples of additional inactive ingredients that can be added to provide desirable color, taste, stability, buffering capacity, dispersion or other known desirable features are red iron oxide, silica gel, sodium lauryl sulfate, titanium dioxide, and edible white ink. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

Compositions prepared for intravenous administration typically contain 100 to 500 ml of sterile 0.9% NaCl or 5% glucose optionally supplemented with a 20% albumin solution. Methods for preparing parenterally administrable compositions are described in more detail in various sources, including, for example, Remington's Pharmaceutical Science, Mack Publishing, Philadelphia, Pa., 17th ed., (1985).

Particularly when the compositions are to be used in vivo, the components used to formulate the pharmaceutical compositions of the present invention are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which can be present during the synthesis or purification process. Compositions for parental administration are also sterile, substantially isotonic and made under GMP conditions.

The following examples are provided to illustrate certain aspects of the invention and are not to be construed to limit the invention.

EXAMPLE 1

Preparation of Cells Expressing Exogenous Transport Proteins

I. Transfection and Selection of Transporter-Expressing Cell Lines

CHO K1 cells ($10^7$/ml) were transfected by electroporation (400V, 250 μfarads) with 40 μg of transporter DNA with neo as the selectable marker. After allowing two days for integration of the DNA into the cellular genome, G418 (1.0 mg/ml) was added. The cells were selected for ten days. The selected population was then incubated at 37° C. for 30 min in transport buffer containing a fluorescent substrate for the transporter. For hPEPT1 and rPEPT1, 500 μM XP10486 was used as the fluorescent substrate (see Example 4 for the preparation and structure of XP10486); the transport buffer utilized with these particular transporters contained 150 mM NaCl, 3 mM KCl, 1 mM $CaCl_2$, 1 mM $MgCl_2$, 1 mM $NaH_2PO_4$, 5 mM glucose and 5 mM MES, pH 6.0.

The cells were then cloned using a Cytomation MoFlo flow cytometer gated on the most highly fluorescent cell population and the live cell population (forward vs. side scatter). The resultant clones were transferred to additional 96-well plates and assayed for transport activity using a radioactive substrate. The clone with the highest transport activity was selected and expanded for screening libraries of potential fluorescent substrates.

EXAMPLE 2

Protocols for Direct Uptake Assays

Figure 5:
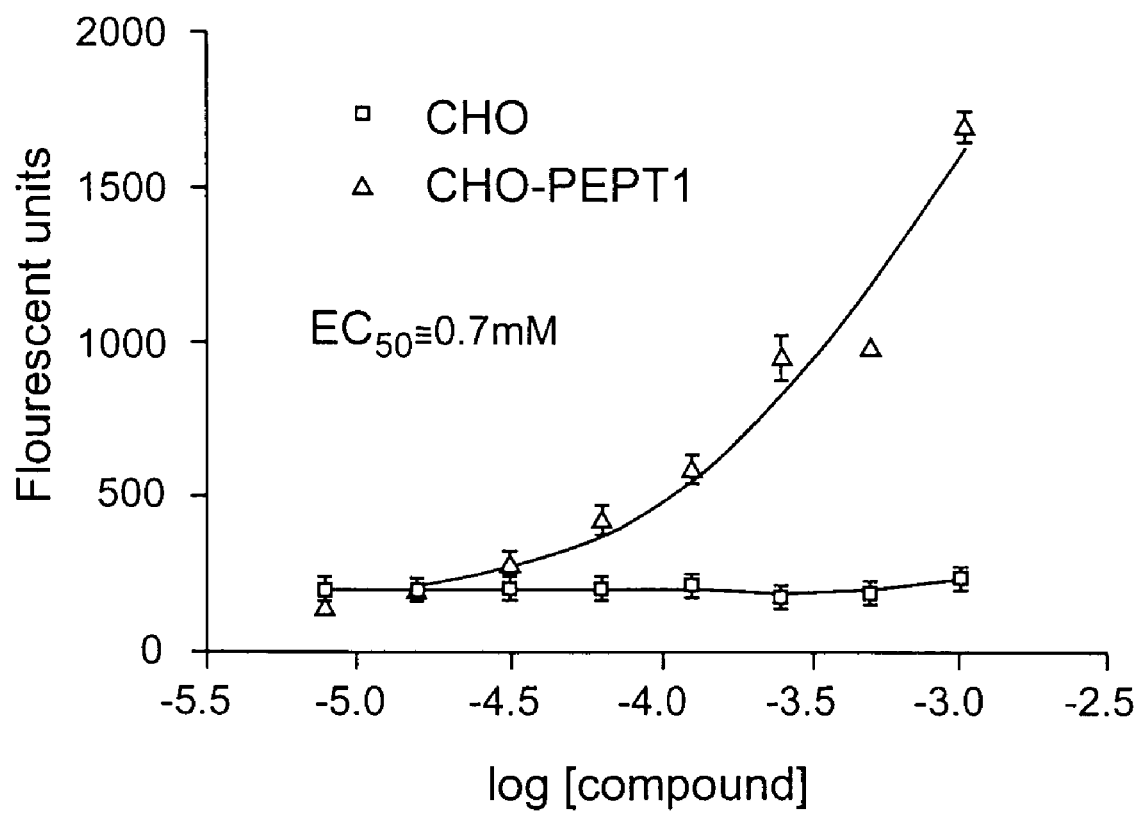
FIG. 5 is a chart showing uptake of the PEPT1 substrate XP 10486 (see Example 4 for synthesis) into CHO cells expressing PEPT1 and control cells that do not express PEPT1.

I. Methods for Detecting Fluorescent Substrate Uptake
  A. Bile Acid Transporters
  Day 1: Seed cells (e.g., CHO IBAT or CHO LBAT) at 100K/well into clear bottom black 96-well tissue culture treated plates.
  Day 2: Wash cells 2× with HBSS buffer (HBSS from Gibco, 10 mM Hepes, pH 7.0) at 100 µl/well.
  Add 50 µl of various concentrations of compounds dissolved in HBSS buffer (Hanks Balanced Salt Solution).
  or buffer alone to each well.
  Incubate 1 hr at RT in the dark (to minimize any negative effects of light on fluorescent properties of putative substrate).
  Read Input Fluorescent Units (FU) in Tecan Spectrafluor instrument, measuring from the bottom of the well. Appropriate excitation and emission wavelengths are utilized as determined by instrument at optimal gain.
  Wash each well 4× with 100 µl/well HBSS at 4° C.
  Add HBSS at 50 µl/well.
  Determine amount of fluorescent substrate transported by measuring FU in wells as above, using the same gain.
  CHO K1 cells used as control for non-transporter dependent transport.
  B. PEPT1 Transporters
  Day 1: Seed CHO hPEPT1 cells at 100K/well into clear bottom black 96-well tissue culture treated plates.
  Day 2: Wash cells 2× with pH 6.0 buffer (1 mM $CaCl_2$, 1 mM $MgCl_2$, 150 mM NaCl, 3 mM KCl, 1 mM $NaH_2PO_4$, 5 mM D-glucose and 5 mM MES, pH 6.0) at RT.
  Add 50 µl of various concentrations of compounds dissolved in pH 6.0 buffer or buffer alone to each well.
  Incubate 1 hr RT in the dark (to minimize any negative effects of light on fluorescent properties of putative substrate).
  Read Input Fluorescent Units (FU) in Tecan Spectrafluor instrument (read from bottom of plate). Use appropriate excitation and emission wavelengths, using optimal gain, determined by instrument.
  Wash 2×100 µl/well pH 6.0 at 4° C. Add 100 µl/well of the same buffer, let sit for 10 min. at RT. Wash 2×100 µl/well pH 6.0 at 4° C. This washing procedure helps minimize the non-specific adherence of fluorescent compounds to the outside of the cells.
  Add above buffer at 50 µl/well.
  Determine amount of fluorescent substrate transported by measuring FU in wells as above, using the same gain.
  Untransfected CHO K1 cells used as control for non-transporter dependent transport.
  Results demonstrating the uptake of XP10486 in CHO cells expressing PEPT1 as compared to control cells not expressing PEPT1 are presented in FIG. 5.

II. Methods for Determining Radioactive Substrate Uptake
  A. Bile Acid Transporters
  Day 1: Seed cells (e.g., CHO IBAT or CHO LBAT) at 100K/well into clear bottom white 96-well tissue culture treated plates.
  Day 2: Wash cells 2× with HBSS buffer pH 7.0 at 100 µl/well.
  Add 50 µl of various concentrations of radiolabeled compounds dissolved in HBSS buffer or buffer alone to each well.
  Incubate 1 hr. RT.
  Wash cells 4×100 µl/well with HBSS at 4° C.
  Add 200 µl scintillation fluid/well. Shake for 5-15 min. RT.
  Count in Wallac microbeta counter for 1 min/well.
  Untransfected CHO K1 cells used as control for non-transporter dependent transport.
  B. PEPT1 Transporters
  Day 1: Seed CHO hPEPT1 cells at 100K/well into clear bottom white 96-well tissue culture treated plates.
  Day 2: Wash cells 2× with pH 6.0 buffer (1 mM $CaCl_2$, 1 mM $MgCl_2$, 150 mM NaCl, 3 mM KCl, 1 mM $NaH_2PO_4$, 5 mM D-glucose and 5 mM MES, pH 6.0) at RT at 100 µl/well.
  Add 50 µl of various concentrations of radiolabeled compounds dissolved in pH 6.0 buffer or buffer alone to each well.
  Incubate 1 hr. RT.
  Wash 2×100 µl/well pH 6.0 at 4° C. Add 100 µl/well of the same buffer, let sit for 10 min. at RT. Wash 2×100 µl/well pH 6.0 at 4° C. This wash procedure minimizes the non-specific adherence of radioactivity to the cells.
  Add 200 µl scintillation fluid/well. Shake for 5-15 min. RT.
  Count in Wallac microbeta counter for 1 min/well.
  Untransfected CHO K1 cells used as control for non-transporter dependent transport.

III. Methods for Detecting Radioactive Substrate Uptake in Competitive Format
  A. Bile Acid Transporters—96 Well Format
  Day 1: Seed cells (e.g., CHO IBAT or CHO LBAT) at 100K/well into clear bottom white 96-well tissue culture treated plates.
  Day 2: Wash cells 2× with HBSS buffer pH 7.0 at 100 µl/well.
  To each well, add:
    25 µl/well of buffer (HBSS, pH 7.0) or test compounds at 2× final concentration in buffer; and
    25 µl/well of $^3$H-taurocholate at 50,000 CPM/well in HBSS buffer containing 10 µM cold taurocholate for IBAT cells, or 20 µM cold Taurocholate for LBAT cells (final concentration of taurocholate in assay is 5 µM or 10 µM, respectively).
  Incubate 1 hr. RT.
  Wash cells 4×100 µl/well with HBSS at 4° C.
  Add 200 µl scintillation fluid/well. Shake for 5-15 min. RT.
  Count in Wallac microbeta counter for 1 min/well.
  B. PEPT1 Transporters—96 Well Format
  Day 1: Seed CHO hPEPT1 cells at 100K/well into clear bottom white 96-well tissue culture treated plates.
  Day 2: Wash cells 2× with pH 6.0 buffer (1 mM $CaCl_2$, 1 mM $MgCl_2$, 150 mM NaCl, 3 mM KCl, 1 mM $NaH_2PO_4$, 5 mM D-glucose and 5 mM MES, pH 6.0) at RT at 100 µl/well.
  To each well, add:
    25 µl/well of pH 6.0 buffer or test compounds at 2× final concentration in buffer;
    25 µl/well of $^3$H-Gly-Sar (Glycylsarcosine) at 100,000 CPM/well in pH 6.0 buffer containing 400 µM unlabeled GlySar (final concentration will be 200 µM).
  Incubate 1 hr. RT.
  Wash 2×100 µl/well pH 6.0 at 4° C. Add 100 µl/well of the same buffer, let sit for 10 min. at RT. Wash 2×100 µl/well pH 6.0 at 4° C. This wash procedure minimizes the non-specific adherence of radioactivity to the cells.
  Add 200 µl scintillation fluid/well. Shake for 5-15 min. RT.
  Count in Wallac microbeta counter for 1 min/well.

C. A. Bile Acid Transporters—384 Well Format

Day 1: Seed cells (e.g., CHO IBAT or CHO LBAT) at 50K/well into clear bottom white 384-well tissue culture treated plates.

Day 2: Wash cells 2× with HBSS buffer pH 7.0 at 70 µl/well.

To each well, add:
25 µl/well of buffer (HBSS, pH 7.0) or test compounds at 2× final concentration in buffer; and
25 µl/well of $^3$H-taurocholate at 75,000 CPM/well in HBSS buffer containing 0.2 µM cold Taurocholate for LBAT cells (final concentration of taurocholate in assay is 0.1 µM).

Incubate 1 hr. RT.

Wash cells 3×70 µl/well with HBSS at 4° C.

Add 200 µl scintillation fluid/well. Shake for 5-15 min. RT.

Count in Wallac microbeta counter for 1 min/well.

D. Results

Figure 6A:
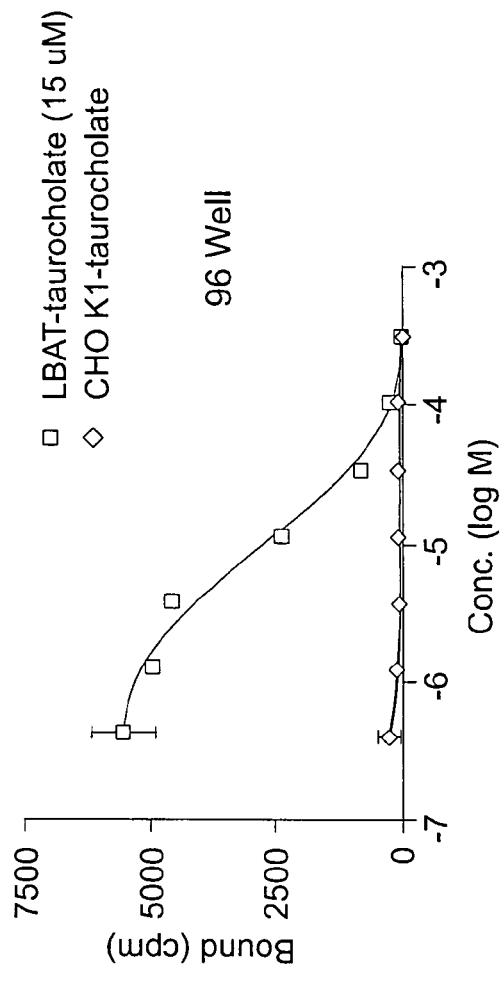
FIGS. 6A and 6B provide charts summarizing competition experiments conducted in both 96 and 384 well formats.
Figure 6B:
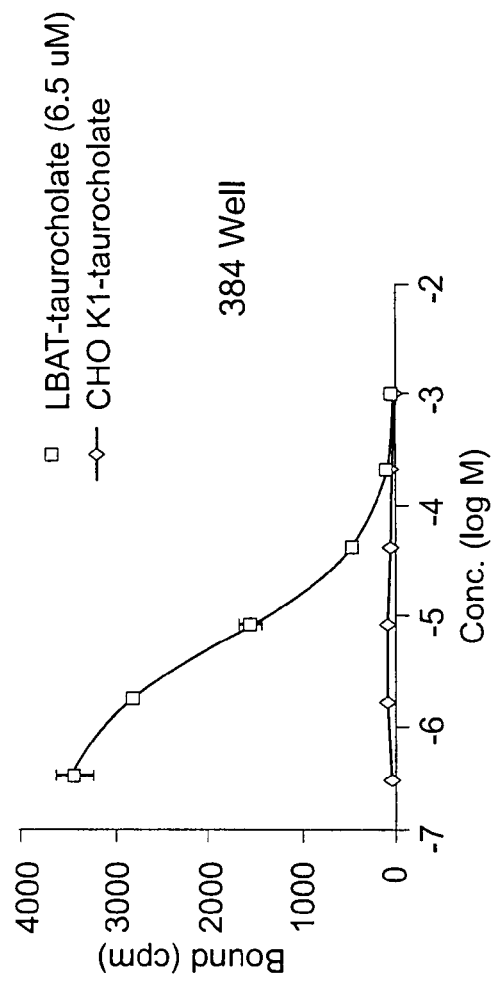

Results of competition experiments conducted with CHO cells expressing the liver bile acid transporter (LBAT) in a 96-well and 384-well format are shown in FIGS. 6A and 6B.

EXAMPLE 3

Library Screening Methods for Cells Expressing Carrier-Type Transport Proteins

I. Screening 200 Member Fluorescent Dipeptide Library

A. Synthesis of Dipeptide Library

Wang resin preloaded with the following 20 protected amino acids can be obtained from Novabiochem: Fmoc-Gly, Fmoc-Ala, Fmoc-Val, Fmoc-Leu, Fmoc-Ile, Fmoc-Met, Fmoc-Pro, Fmoc-Cys(Trt), Fmoc-Ser(O$^t$Bu), Fmoc-Thr(O$^t$Bu), Fmoc-Asn(Trt), Fmoc-Gln(Trt), Fmoc-Asp(O$^t$Bu), Fmoc-Glu(O$^t$Bu), Fmoc-Lys(Boc), Fmoc-Arg(Pmc), Fmoc-Phe, Fmoc-Tyr(O$^t$Bu), Fmoc-His(Trt), Fmoc-Trp(Boc). 100 mg of each resin (loading ~1 mmole/g) is pooled and shaken with 20 mL of a 20% (v/v) solution of piperidine in DMF for 20 min. The resins are washed with DMF (3×), CH$_2$Cl$_2$, MeOH, and CH$_2$Cl$_2$ again, then dried in vacuo and divided into 2 equal aliquots. The first is treated with 20 mL of a DMF solution containing α-Fmoc-γ-Alloc-diaminobutyric acid (250 mM), HATU (250 mM) and DIEA (500 mM). The resin is agitated for 8 h then filtered and washed with DMF (3×), CH$_2$Cl$_2$, MeOH, and CH$_2$Cl$_2$ again, then dried in vacuo. The second aliquot of resin is similarly treated with α-Fmoc-ε-Alloc-lysine. The Alloc protecting group is removed from these 2 aliquots by separately treating each with Pd(PPh$_3$)$_4$ (0.23 g) in CH$_2$Cl$_2$ (20 mL) followed by addition of tetrabutylammonium fluoride (0.78 g) and azidotrimethylsilane (1.06 mL). The resin is shaken under nitrogen for 30 min, then drained and the resin washed with CH$_2$Cl$_2$ (2×20 mL). The deprotection procedure is then repeated.

Figure 7:
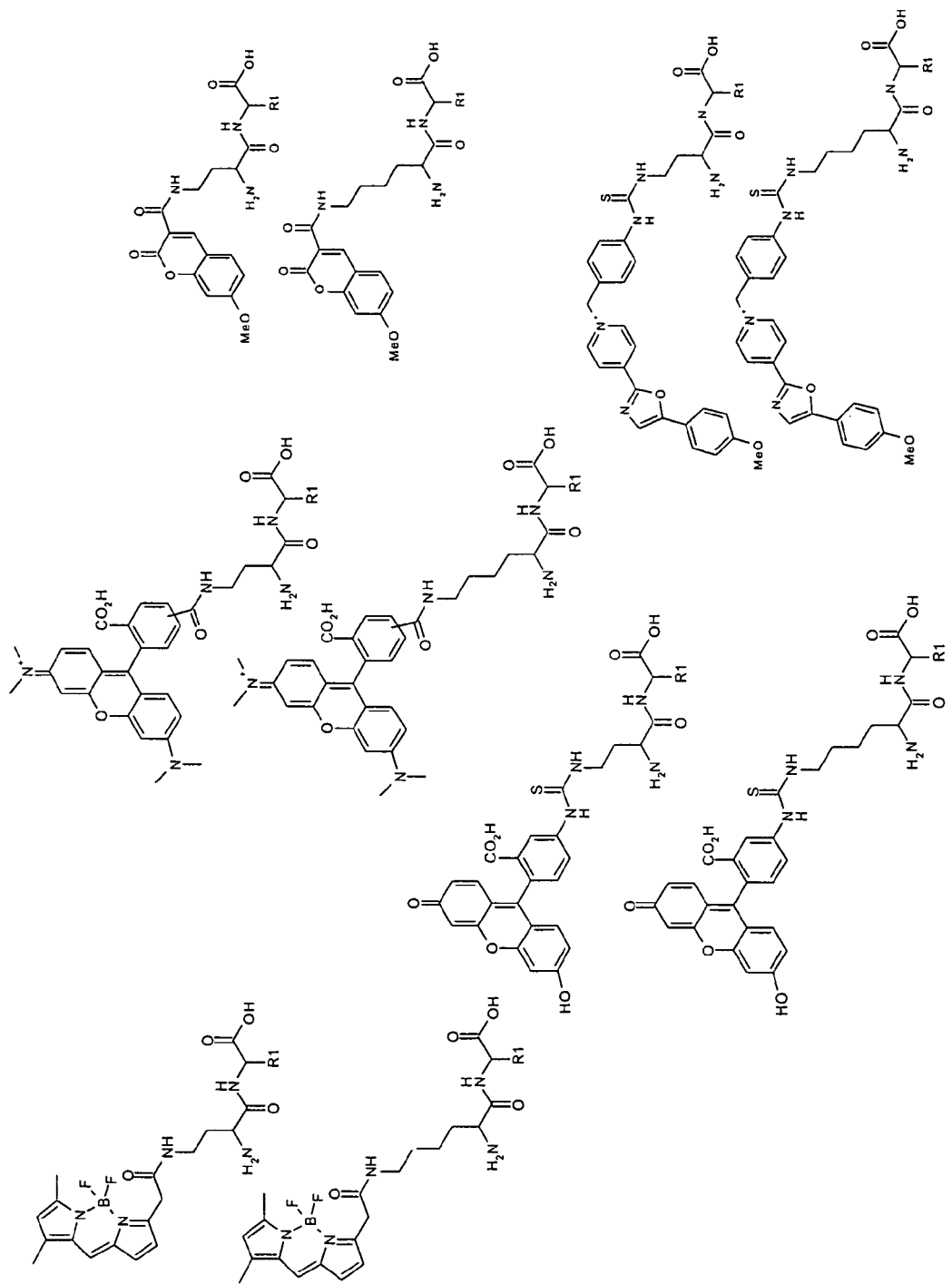
FIG. 7 shows ten pools of compounds obtained during synthesis of a 200 member fluorescent dipeptide library.

The resins are subsequently treated with a 3% (v/v) solution of sodium diethyldithiocarbamate in DMF containing 5% (v/v) DIEA (20 mL) to remove any residual palladium. After shaking for 10 min, the mixture is drained and then washed with DMF (3×), CH$_2$Cl$_2$, MeOH, and CH$_2$Cl$_2$ again, then dried in vacuo. Each aliquot is then equally divided into 5 sub-pools for reaction with one of 5 DMF solutions containing 1 mmole of a different fluorescent reagent, i.e. (a) 4,4-difluoro-5,7-dimethyl-4-bora-3a,4a-diaza-s-indacene-3-propionic acid, succinimidyl ester (BODIPY FL, SE); (b) fluorescein-5-isothiocyanate (FITC); (c) 5 and 6-carboxytetramethylrhodamine, succinimidyl ester (5(6)-TAMRA, SE); (d) 7-methoxycoumarin-3-carboxylic acid, succinimidyl ester; (e) 1-(3-isothiocyanatophenyl)-4-(5-(4-methoxyphenyl)oxazol-2-yl))pyridinium bromide (PyMPO-ITC). After shaking for 4 h, the supernatants are drained and the resins washed extensively with DMF (6×), CH$_2$Cl$_2$ (2×), MeOH (2×), and CH$_2$Cl$_2$ (2×) again, then dried in vacuo. Each of the 10 pools is treated with 2 mL of a 20% (v/v) solution of piperidine in DMF for 20 min. The resins are washed with DMF (3×), CH$_2$Cl$_2$, MeOH, and CH$_2$Cl$_2$ again, then dried in vacuo. A small portion (~5 mg) of each pool is reserved for single bead screening while the remainder is cleaved by addition of 10 mL of a 90:5:5 solution of TFA: H$_2$O: Et$_3$SiH. After agitation for 30 min, the supernatants are drained, the resins washed with 50% TFA:CH$_2$Cl$_2$ (10 mL) and the combined filtrates evaporated to dryness. The resulting 10 pools are shown in FIG. 7.

B. Library Screening for hPEPT1 Substrates

CHO cell lines expressing the human dipeptide transporter PETP1 are prepared as described in Example I, with CHO-K1 cells serving as a negative-control cell-line. The library just described in section I.A. of this example is then screened according to the protocol set forth in Example II. The best peptide substrate (i.e., with the greatest $V_{max}/K_m$) is selected for use as a fluorescent probe for screening libraries for hPEPT1 substrates in competition assays.

Figure 8:
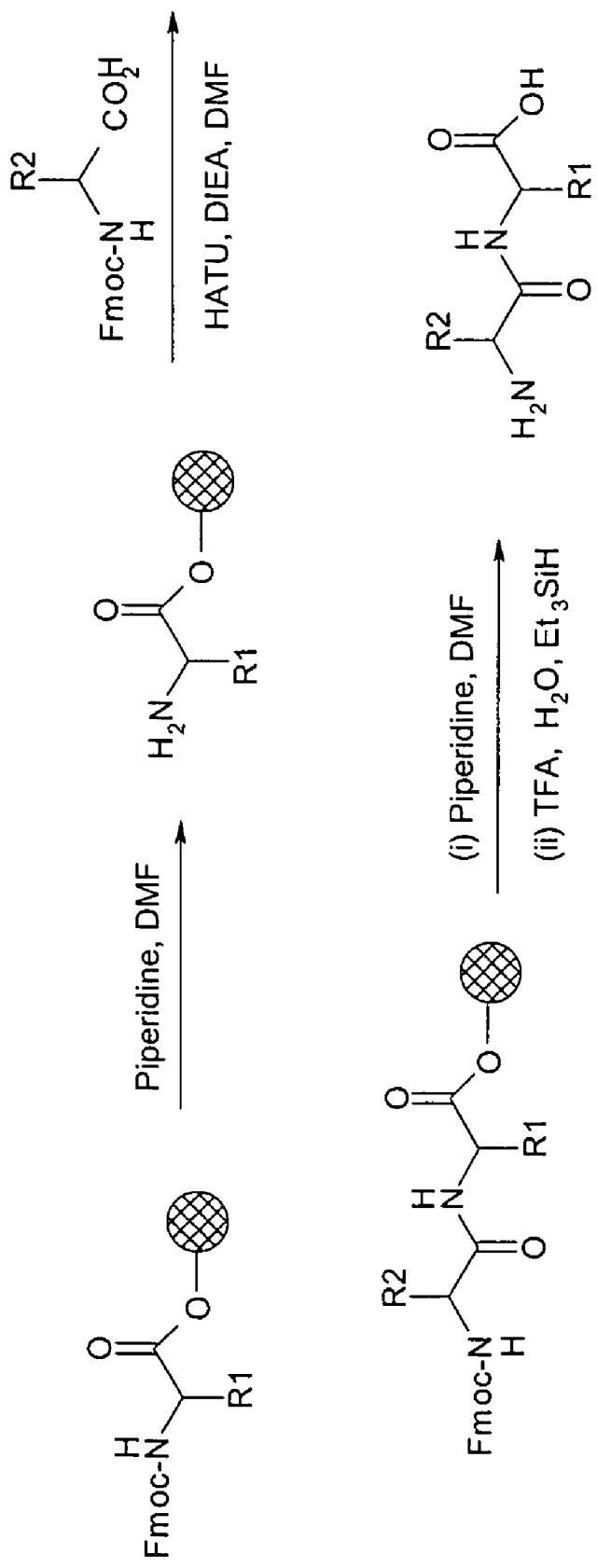
FIG. 8 shows an example of the synthetic steps involved in preparing a dipeptide library for use in screening against certain transporters.

II. Screening 400-Member Dipeptide Library and 400-Member β-Lactam Libraries for PEPT1 Substrate A. Synthesis of 400 Member Dipeptide Library A summary of the major steps in the synthesis of this library is presented in FIG. 8. Wang resin preloaded with the following 20 protected amino acids can be obtained from Novabiochem: Fmoc-Gly, Fmoc-Ala, Fmoc-Val, Fmoc-Leu, Fmoc-Ile, Fmoc-Met, Fmoc-Pro, Fmoc-Cys(Trt), Fmoc-Ser(O$^t$Bu), Fmoc-Thr(O$^t$Bu), Fmoc-Asn(Trt), Fmoc-Gln(Trt), Fmoc-Asp(O$^t$Bu), Fmoc-Glu(O$^t$Bu), Fmoc-Lys(Boc), Fmoc-Arg(Pmc), Fmoc-Phe, Fmoc-Tyr(O$^t$Bu), Fmoc-His(Trt), Fmoc-Trp(Boc). 1 g of each resin (loading ~1 mmole/g) is divided into 20×50 mg aliquots and individual aliquots are added to 5 deep-well microtiter plates (80 wells per plate) fitted with filter frits (e.g. available from Polyfiltronics or Robbins Scientific). To each well is added 0.5 mL of a 20% (v/v) solution of piperidine in DMF. The plates are agitated for 20 min and the supernatants drained (by evacuation). The resins are washed with DMF (3×), CH$_2$Cl$_2$, MeOH, and CH$_2$Cl$_2$ again, then dried in vacuo.

Separate DMF solutions are prepared containing one of the 20 protected amino acids [i.e. Fmoc-Gly, Fmoc-Ala, Fmoc-Val, Fmoc-Leu, Fmoc-Ile, Fmoc-Met, Fmoc-Pro, Fmoc-Cys(Trt), Fmoc-Ser(O$^t$Bu), Fmoc-Thr(O$^t$Bu), Fmoc-Asn(Trt), Fmoc-Gln(Trt), Fmoc-Asp(O$^t$Bu), Fmoc-Glu(O$^t$Bu), Fmoc-Lys(Boc), Fmoc-Arg(Pmc), Fmoc-Phe, Fmoc-Tyr(O$^t$Bu), Fmoc-His(Trt), Fmoc-Trp(Boc)] at 250 mM, plus HATU (250 mM) and DIEA (500 mM). 1 mL of each solution is added to an aliquot of each resin and the plates agitated for 8 h to form the 400 discrete protected dipeptides. The supernatants are drained and the resins washed with DMF (3×), CH$_2$Cl$_2$, MeOH, and CH$_2$Cl$_2$ again, then dried in vacuo. To each well is added 0.5 mL of a 20% (v/v) solution of piperidine in DMF, the plates agitated for 20 min, then the supernatants are drained and the resins washed with DMF (3×), CH$_2$Cl$_2$, MeOH, and CH$_2$Cl$_2$ again, then dried in vacuo. The 400 dipeptides are cleaved from resin by addition to each well of 0.5 mL of a 90:5:5 solution of TFA: H$_2$O: Et$_3$SiH. After agitation for 30 min, the supernatants are drained into deep well microtiter plates, the resins washed with CH$_2$Cl$_2$ (0.5 mL) and the combined filtrates evaporated to dryness using a Genevac concentrator.

B. Parallel Synthesis of a 400 Member β-Lactam Library

Figure 9:
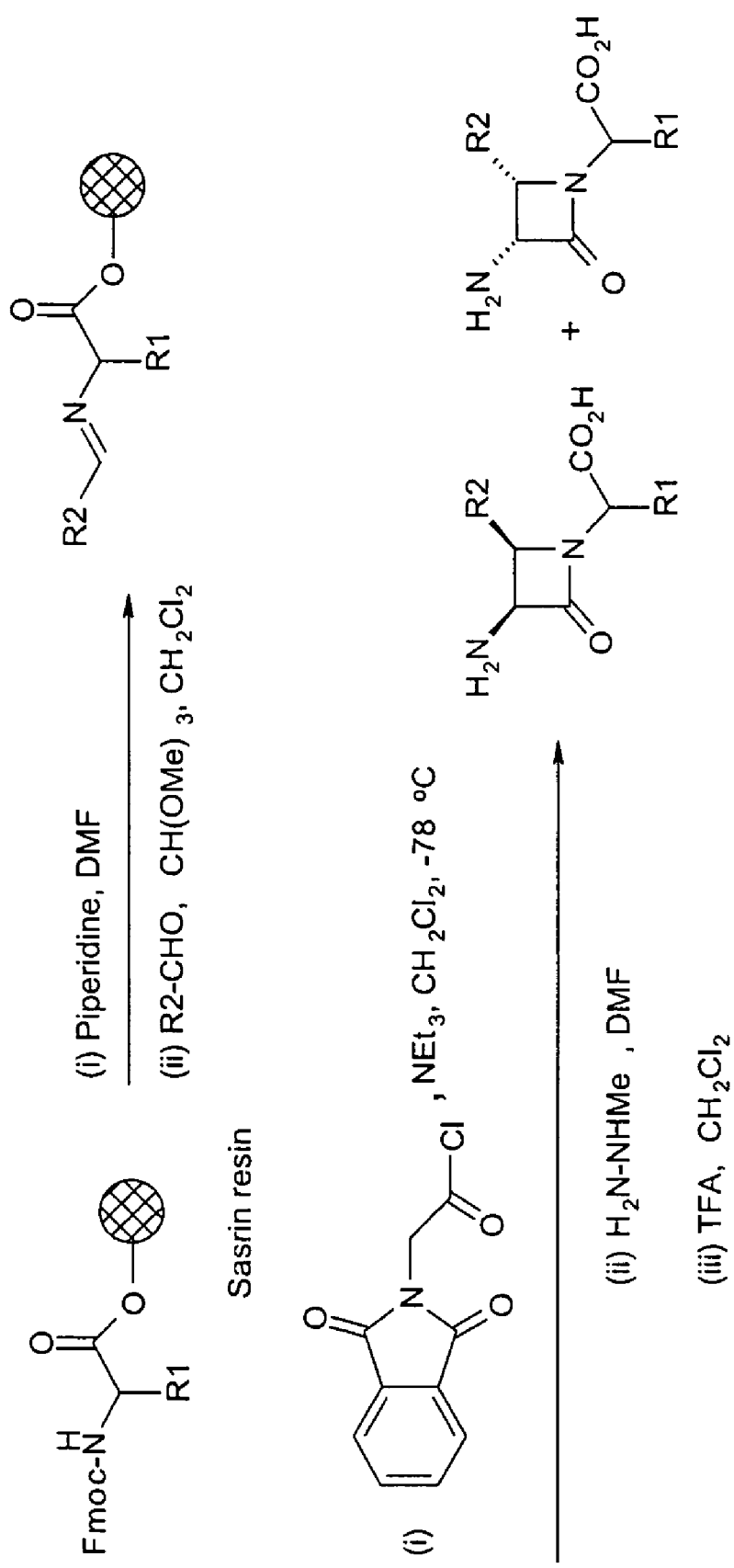
FIG. 9 shows an example of the synthetic steps involved in preparing a β-lactam library for use in screening against certain transporters.

A scheme for synthesizing a β-lactam library for use in screening methods is presented in FIG. 9. Sasrin resin preloaded with the following 20 protected amino acids can be obtained from Bachem: Fmoc-Gly, Fmoc-Ala, Fmoc-Val, Fmoc-Leu, Fmoc-Ile, Fmoc-Met, Fmoc-Pro, Fmoc-Cys(Trt), Fmoc-Ser(O$^t$Bu), Fmoc-Thr(O$^t$Bu), Fmoc-Asn(Trt), Fmoc-Gln(Trt), Fmoc-Asp(O$^t$Bu), Fmoc-Glu(O$^t$Bu), Fmoc-Lys (Boc), Fmoc-Arg(Pmc), Fmoc-Phe, Fmoc-Tyr(O$^t$Bu), Fmoc-His(Trt), Fmoc-Trp(Boc). 1 g of each resin (loading ~0.6 mmole/g) is treated with 10 mL of a 20% (v/v) solution of piperidine in DMF for 20 min. The resins are washed with DMF (3×), CH$_2$Cl$_2$, MeOH, and CH$_2$Cl$_2$ again, then dried in vacuo. Each sample is divided into 10×100 mg aliquots and the resins suspended in a 80% (v/v) solution of trimethylorthoformate in CH$_2$Cl$_2$ (1 mL). 200 different imines are formed by addition of one of ten aldehydes: (i) benzaldehyde; (ii) cinnamaldehyde; (iii) cyclohexyl aldehyde; (iv) 2-furyl aldehyde; (v) 2-thiophene aldehyde; (vi) 2-pyridyl aldehyde; (vii) 3-quinolyl aldehyde; (viii) 3,4-dichlorobenzaldehyde; (ix) 4-carbomethoxybenzaldehyde; (x) 4-biphenylaldehyde. 1 mL of a 1.6 M solution of the aldehyde in CH$_2$Cl$_2$ is added, the resins shaken for 3 h then drained and washed with CH$_2$Cl$_2$ (2×).

The resins are resuspended in CH$_2$Cl$_2$ (2 mL) and cooled to −78° C. Triethylamine (1.2 mmol) and phthalimidoacetyl chloride (0.9 mmol) are added to each and the resins warmed to room temperature overnight with stirring. The resins are drained and washed with CH$_2$Cl$_2$ (2×). The phthalimido protecting group is removed by treatment with a DMF solution of N-methylhydrazine (1M) and the samples cleaved from resin by treatment with a 3% (v/v) solution of TFA in CH$_2$Cl$_2$. The resulting products are dried in vacuo using a Genevac concentrator to yield 200 samples containing approximately equimolar mixtures of β-lactams as two cis-diastereomers.

C. Screening the Dipeptide and β-Lactam Libraries for hPEPT1 Substrates

The libraries prepared as just described (i.e., sections II.A and II.B of this example) are screened for the presence of hPEPT1 substrates in a two-part protocol. Initially a competition assay is used to identify the most effective inhibitors of uptake of a reporter substrate (e.g., either radiolabeled Gly-Sar, or the fluorescent substrate identified in section I.B. of this Example). The selected inhibitors are then retested in either a CHO/hPEPT1 uptake assay or a transepithelial flux assay across a confluent Caco-2 cell monolayer. The transported substrates are detected by LC-MS analysis using an HP 1100 MSD instrument and a reversed-phase C18 column (5 μm, 2.1 mm×10 cm) eluting with MeCN/H$_2$O/0.1% formic acid.

1. Fluorescence Competition Assay

CHO/hPEPT1 cells are seeded in microtiter plates at a density of 5×10$^4$ cells/well. At 2 days post-seeding, the medium is removed and the cells washed twice with pH 6.0 uptake buffer (1 mM CaCl$_2$, 1 mM MgCl$_2$, 150 mM NaCl, 3 mM KCl, 1 mM NaH$_2$PO$_4$, 5 mM D-glucose and 5 mM MES). The library samples are dissolved in uptake buffer at concentrations ranging from 5 μM to 10 mM together with the fluorescent reporter substrate at 50 μM and added to the CHO/hPEPT1 cells in duplicate experiments. At various time points (10, 20, 30, 45, 60 and 90 min) the supernatants are removed and the cells washed with ice-cold uptake buffer (3×). The cells are visualized by confocal fluorescence microscopy and scored for accumulation of the fluorescent reporter in the cytoplasm. Compounds strongly inhibiting reporter uptake are selected for further analysis.

2. CHO/hPEPT1 Uptake Assay

CHO/hPEPT1 cells are seeded in six-well culture plates at a density of 10$^5$ cells/cm$^2$. At 2 days post-seeding, the medium is removed and the cells washed twice with pH 6.0 uptake buffer (1 mM CaCl$_2$, 1 mM MgCl$_2$, 150 mM NaCl, 3 mM KCl, 1 mM NaH$_2$PO$_4$, 5 mM D-glucose and 5 mM MES). The library samples are dissolved in uptake buffer at concentrations ranging from 5 μM to 10 mM and added to the CHO/hPEPT1 cells in duplicate experiments. At various time points (10, 20, 30, 45, 60 and 90 min) the supernatants are removed and the cells washed with ice-cold uptake buffer (3×). Water (1 mL) is added to each well and incubated for 30 min at 25° C. Cells are harvested and sonicated for 2 min. ZnSO$_4$ solution (8%, 0.2 mL) is added to the cell lysate, vortexed vigorously and centrifuged for 5 min at 3000 rpm. After passage through a 0.45 μm filter, the samples are analyzed for the presence of library compound by LC-MS. Samples for which uptake exceeded that observed for the control CHO-K1 cell line are identified as hPEPT1 substrates.

3. Caco-2 Transepithelial Flux Assay

Caco-2 cells, which naturally express the hPEPT1 transporter, are cultured for ~20 days on permeable polycarbonate Transwell cell culture inserts (diameter 24.5 mm, Costar) at starting densities of 4×10$^4$ cells/cm$^2$. The lower (receiver) compartment contained 2.5 mL medium and the upper (donor) compartment contained 1.5 mL medium. Transepithelial flux of library compounds is performed at 37° C. by addition of uptake buffer (pH 6.0, 1.5 mL) containing the sample (1 mM) to the donor side. At time intervals of 10, 30, 60 and 120 min, 0.2 mL samples are taken from the receiver compartment and replaced with fresh buffer (pH 7.5). Samples are analyzed for the presence of transported compound by LC-MS. Integrity of the Caco-2 monolayer is confirmed by measuring the flux of [$^{14}$C]-mannitol.

EXAMPLE 4

Library Screening Methods to Assess Structure-Activity Relationships

I. Compound and Library Synthesis

A. Synthesis of XP 10486

Figure 10:
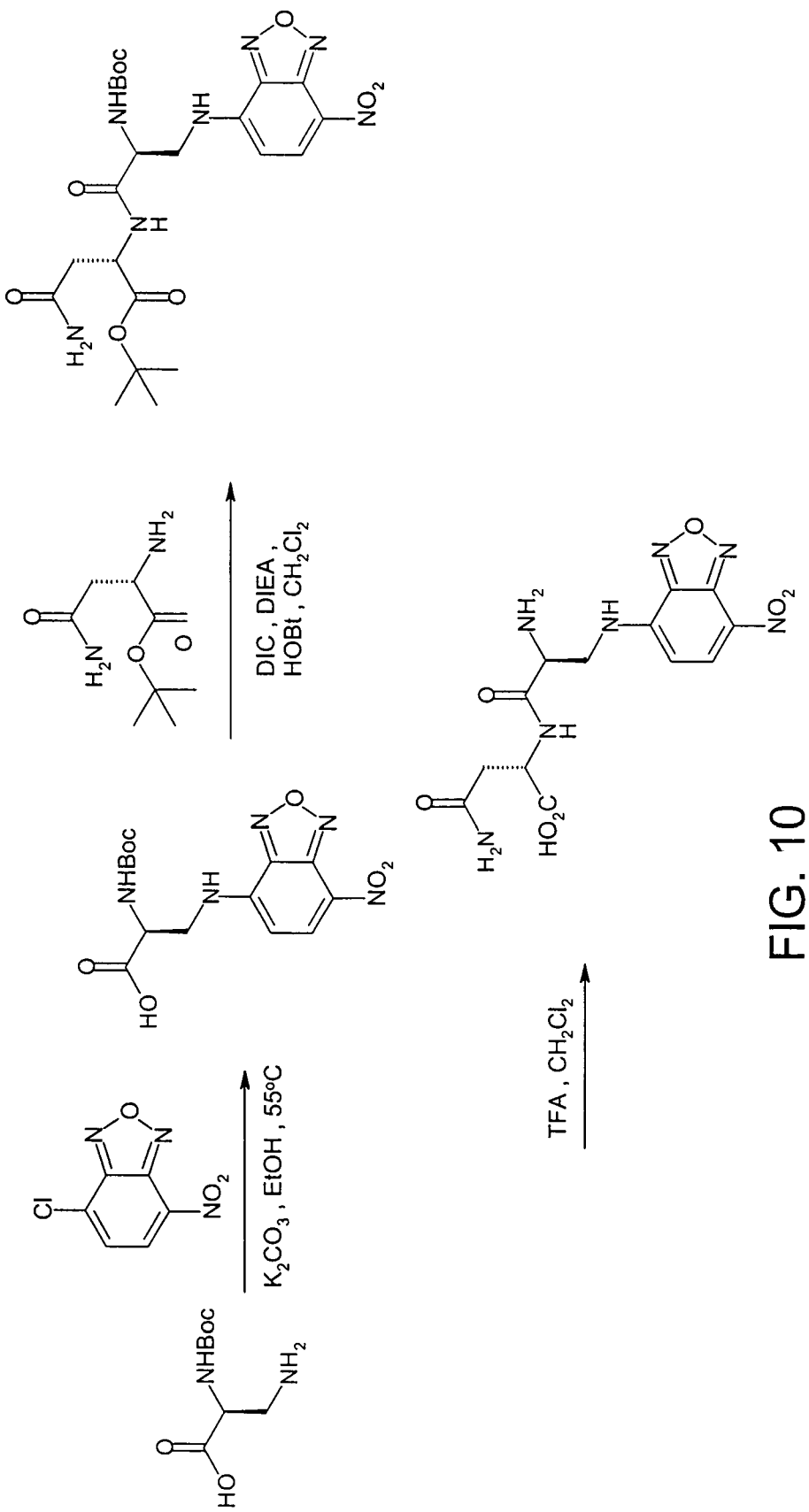
FIG. 10 depicts the major steps in the synthesis of the PEPT1 substrate XP 10486.

FIG. 10 depicts the major steps in the preparation of XP 10486. To α-N-Boc-diaminopropionic acid (1.0 g) and finely powdered, potassium carbonate (1.35 g, 2 eq) in a 100 mL round-bottom flask was added ethanol (30 mL) and 4-chloro-7-nitrobenzofurazan (NCB—Cl, 1.07 g, 1.1 eq). The mixture was heated at 65-70° C. for 1 h, then cooled to room temperature. The solvent was removed in vacuo and the solid material dissolved in water (30 mL). This aqueous solution was extracted with ether (2×30 mL). The aqueous solution was acidified to pH=1-2 with 1M HCl solution, extracted with dichloromethane (3×30 mL) and the organic layer dried over anhydrous sodium sulfate. The solvent was removed in vacuo to yield α-N-Boc-β-N—NBD-diaminopropionic acid (1.63 g, 91% based on starting diaminopropionic acid).

Freshly prepared α-N-Boc-β-N—NBD-diaminopropionic acid (0.8 g) was dissolved in dichloromethane (40 mL) containing HOBt (0.33 g, 1.5 eq), asparagine t-butyl ester hydrochloride (0.59 g, 1.2 eq) and DIEA (0.46 mL, 1.2 eq). DIC (0.51 mL, 1.5 eq) was added dropwise and the reaction mixture stirred at room temperature for 18 h. The reaction mixture was diluted with dichloromethane (40 mL) and extracted with 1M HCl solution (2×10 mL) and then saturated sodium bicarbonate solution (2×10 mL). The organic layer was dried over anhydrous sodium sulfate and the solvent removed in vacuo.

Column chromatography on silica gel provided the pure protected dipeptide. TFA (20 mL) was added to this product and the reaction mixture stirred at room temperature for 12 h. The solvent was removed in vacuo to yield XP10486 (575 mg, 69% based on starting α-N-Boc-β-N—NBD-diaminopropionic acid). Electrospray mass spectrometry showed the expected molecular ion at m/z=382 (M+H$^+$).

B. Synthesis of NBD-Containing Dipeptide Libraries

Figure 11:
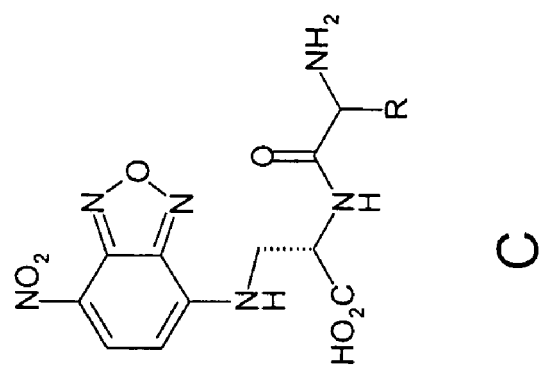
FIG. 11 presents the three major structural motifs in which the reporter NBD is positioned at different locations on a dipeptide backbone.
Figure 11:
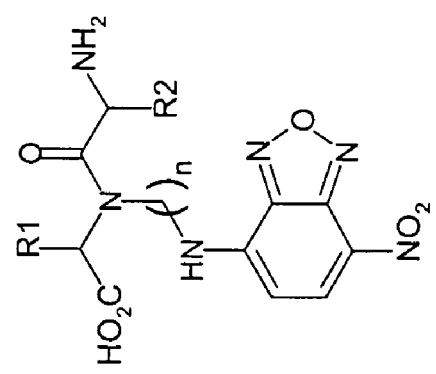
Figure 11:
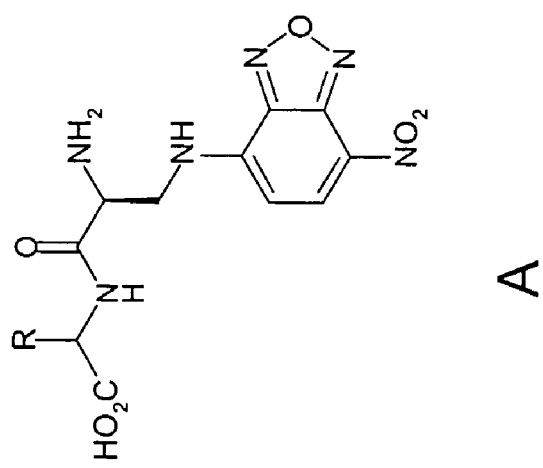

Structure-activity relationships for hPEPT1 substrates can be assessed by synthesizing variant structures based upon the XP 10486 just described in the foregoing section. More specifically, sub-libraries are prepared in which the NBD moiety is conjugated at different sites on the dipeptide backbone of XP 10486. The different types of general structures that can be prepared are shown in FIG. 11.

1. Sub-Library A

Figure 12:
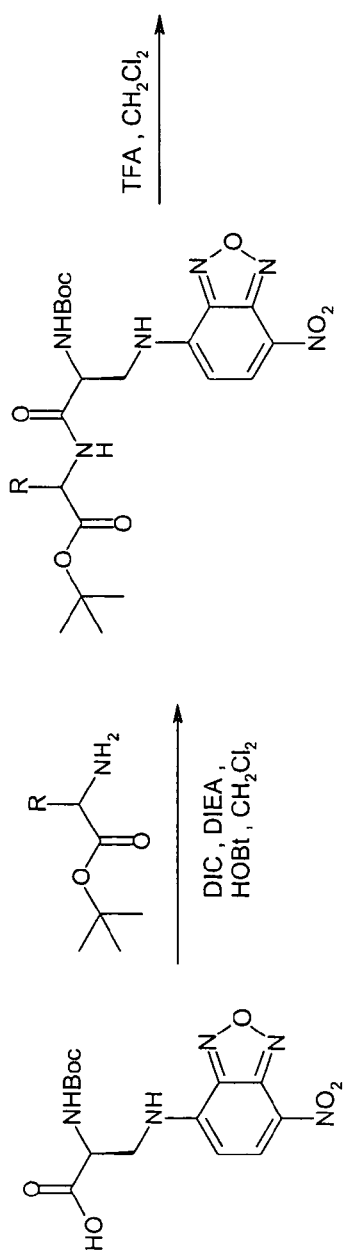
FIGS. 12-14 show steps in the synthesis of different NBD-containing sub-libraries.

As shown in FIG. 12, α-N-Boc-β-N—NBD-diaminopropionic acid (80 mg), prepared as described above in section A of this example, is dissolved in dichloromethane (4 mL) containing HOBt (33 mg, 1.5 eq), DIEA (46 µL, 1.2 eq) and one of the following ten tert-butyl protected α-amino acids (1 eq): Gly-O$^t$Bu, Ala-O$^t$Bu, Val-O$^t$Bu, Pro-O$^t$Bu, Ser(O$^t$Bu)-O$^t$Bu, Asn-O$^t$Bu, Glu(O$^t$Bu)-O$^t$Bu, Lys(Boc)-O$^t$Bu, Phe-O$^t$Bu, His (Trt)-O$^t$Bu. DIC (51 µL, 1.5 eq) is added to each solution and the mixtures stirred at room temperature for 18 h. The mixtures are diluted with dichloromethane (4 mL) and extracted with 1M HCl (2×1 mL) and then saturated sodium bicarbonate (2×1 mL). The organic layers are dried over anhydrous sodium sulfate and the solvent removed in vacuo. Flash chromatography on silica gel provided the pure protected dipeptides. TFA (2 mL) is added to each of these products and after 1 h at room temperature the solvent is removed in vacuo to afford the NBD-containing dipeptides, which are characterized by electrospray mass spectrometry.

2. Sub-Library B

Figure 13:
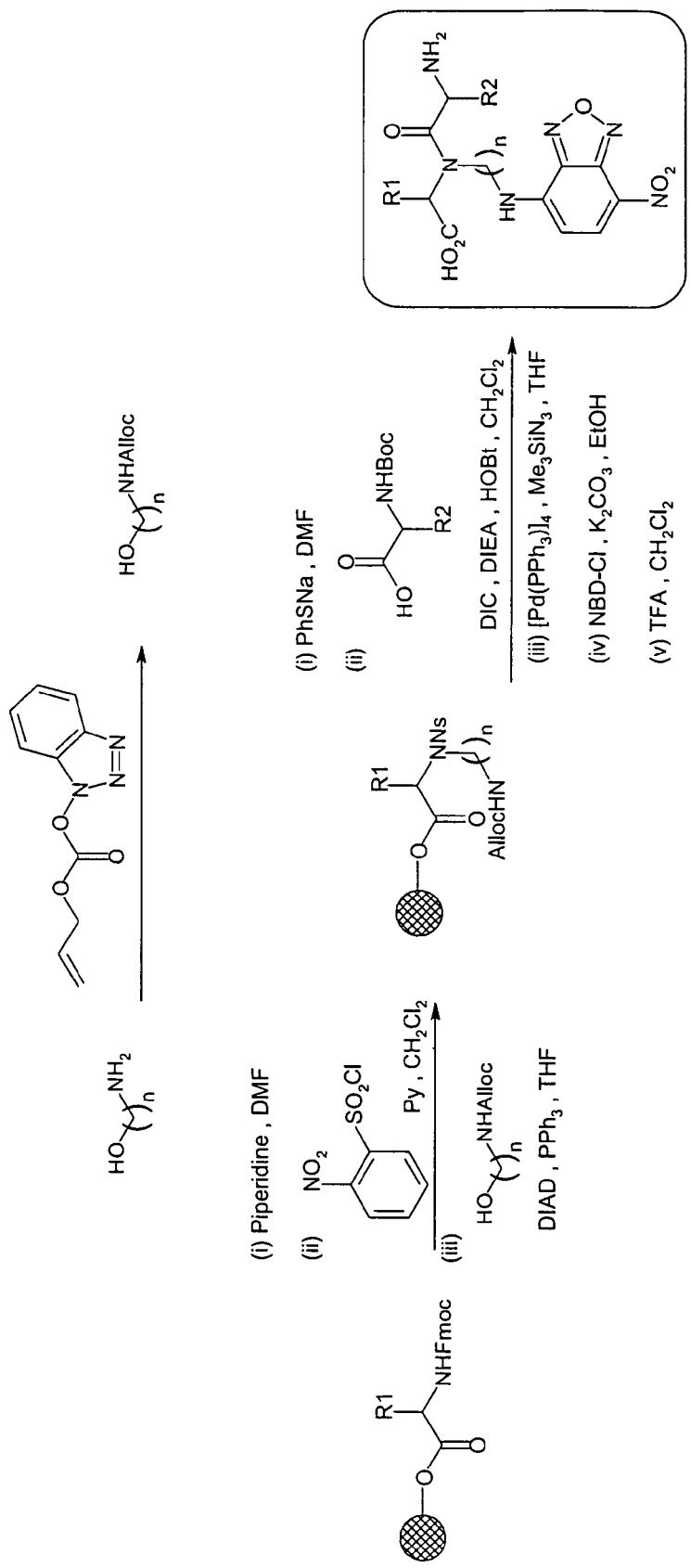

The synthesis of sub-library B is shown in FIG. 13. As shown, to 3-aminopropan-1-ol (10 mmol) is added allyl 1-benzotriazolyl carbonate (10 mmol, 1 eq) in DMF (40 mL) containing DIEA (12 mmol, 1.2 eq) and the reaction mixture stirred at room temperature for 12 h. The solvent is removed in vacuo and the residue dissolved in dichloromethane (40 mL) and extracted with 1M HCl (2×10 mL) and then saturated sodium bicarbonate (2×10 mL). The organic layer is dried over anhydrous sodium sulfate and the solvent removed in vacuo. Chromatography on silica gel provided the pure Alloc-protected amino alcohol. The reaction sequence is repeated starting with 5-aminopentan-1-ol to afford 5-N-Alloc-aminopentan-1-ol.

Two gram samples of Wang resin loaded with each of the 10 following 25, protected amino acids (at 1 mmol/g): Fmoc-Gly, Fmoc-Ala, Fmoc-Val, Fmoc-Pro, Fmoc-Ser(O$^t$Bu), Fmoc-Asn, Fmoc-Glu(O$^t$Bu), Fmoc-Lys(Boc), Fmoc-Phe, Fmoc-His(Trt); are divided into two equal aliquots and are separately treated first with 20% piperidine in DMF for 20 min (followed by washing with DMF (3×) and CH$_2$Cl$_2$), then 2-nitrobenzensulfonyl chloride (10 mmol) in CH$_2$Cl$_2$ (20 mL) containing pyridine (10 mmol), followed by washing with DMF (3×) and CH$_2$Cl$_2$. The first aliquots of resin are suspended in 1:1 v/v anhydrous THF/CH$_2$Cl$_2$ (15 mL) and triphenylphosphine (10 mmol) and 3-N-Alloc-aminopropan-1-ol (10 mmol) are added. The reaction mixture is cooled to 0° C. under nitrogen and diisopropyl azodicarboxylate (DIAD, 10 mmol) in 1:1 v/v anhydrous THF/CH$_2$Cl$_2$ (3 mL) added dropwise. The mixture is then agitated at room temperature for 3 h and the resin filtered and washed with anhydrous DMF, MeOH and CH$_2$Cl$_2$ and dried in vacuo. This Mitsunobu coupling protocol is repeated using the second aliquots of resin with 5-N-Alloc-aminopentan-1-ol.

The twenty resin samples are next treated for 1 h at room temperature with a 1M solution of PhSNa in anhydrous DMF (10 mL) to remove the nitrobenzensulfonyl protecting group and the resins washed with DMF. Each resin sample is divided into 10 equal sized aliquots for coupling to 0.5 mmol of one of the 10 following protected amino acids: Boc-Gly, Boc-Ala, Boc-Val, Fmoc-Pro, Boc-Ser(O$^t$Bu), Boc-Asn, Boc-Glu(O$^t$Bu), Boc-Lys(Boc), Boc-Phe, Boc-His(Boc); in DMF solutions (2 mL) containing HOBt (0.75 mmol), DIEA (0.6 mmol) and DIC (0.75 mmol). After agitating the reaction mixtures for 12 h the resins are filtered and washed with DMF, MeOH and CH$_2$Cl$_2$ then dried in vacuo.

Each sample is next treated with a solution of tetrakis (triphenylphosphine)-palladium(0) (0.02 mmol) in THF (2 mL) followed by addition of tetrabutylammonium fluoride (0.3 mmol) and azidotrimethylsilane (0.8 mmol) in THF (2 mL). After 30 min. the reactions are drained and the resins washed with CH$_2$Cl$_2$ then dried in vacuo. Each sample is then reacted with 4-chloro-7-nitrobenzofurazan (NCB—Cl, 0.5 mmol) in a 1:1 v/v mixture of DMF and EtOH for 1 h at 65-70° C. The samples are cooled, washed with DMF, MeOH and CH$_2$Cl$_2$ and dried in vacuo. Each resin aliquot is finally treated for 1 h with 1 mL of a 1:1 v/v mixture of TFA and CH$_2$Cl$_2$ to cleave the NBD-containing dipeptides from resin. The 200 samples are dried in vacuo.

3. Sub-Library C

Figure 14:
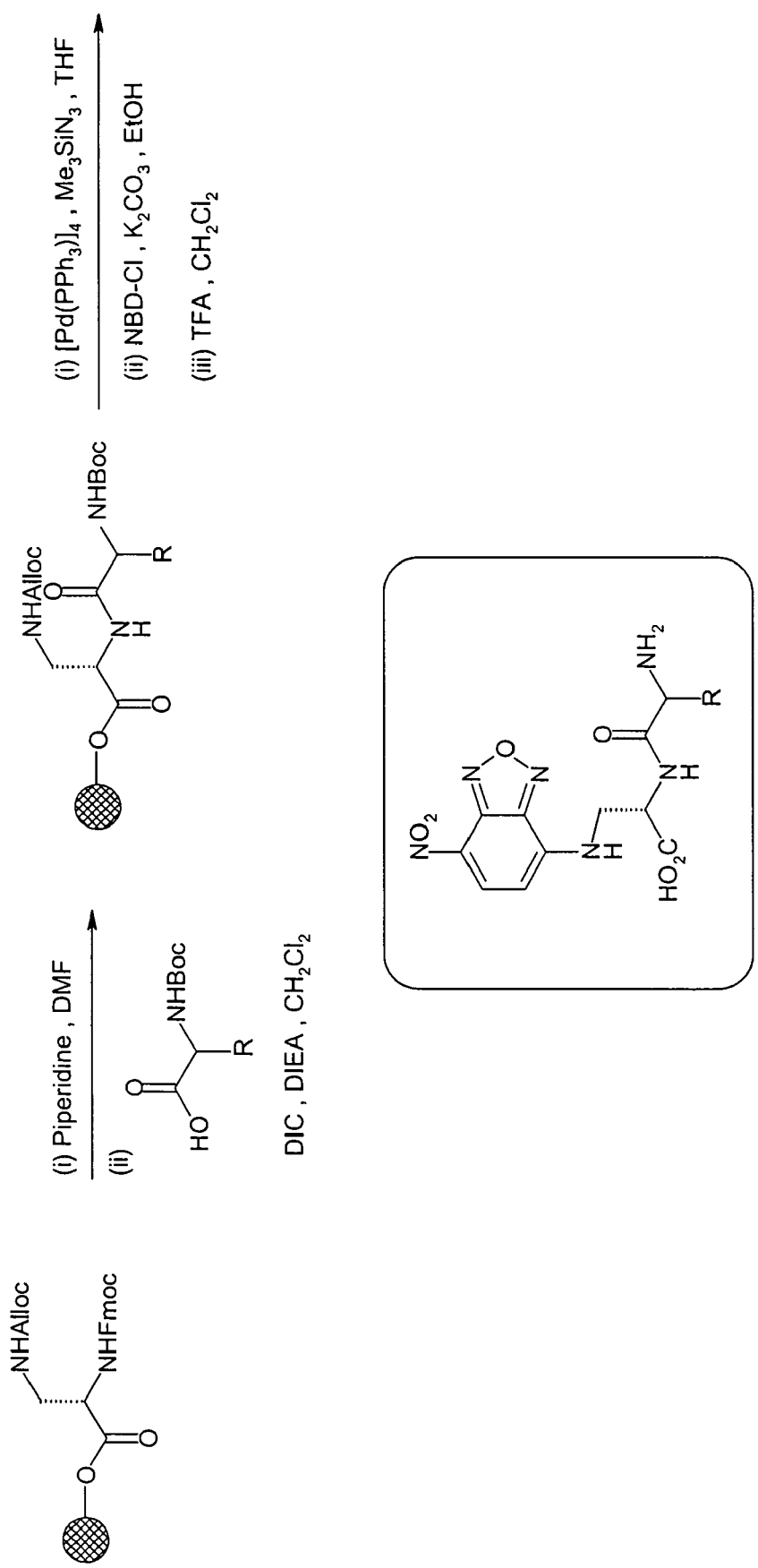

As illustrated in FIG. 14, a 1 g sample of Wang resin loaded with α-N-Fmoc-β-N-Boc-diaminopropionic acid (at 1 mmol/g) is treated with 20% piperidine in DMF for 20 min (followed by washing with DMF (3×) and CH$_2$Cl$_2$), then divided into 10 equally sized aliquots for coupling to 0.5 mmol of one of the 10 following protected amino acids: Boc-Gly, Boc-Ala, Boc-Val, Fmoc-Pro, Boc-Ser(O$^t$Bu), Boc-Asn, Boc-Glu (O$^t$Bu), Boc-Lys(Boc), Boc-Phe, Boc-His(Boc); in DMF solutions (2 mL) containing HOBt (0.75 mmol), DIEA (0.6 mmol) and DIC (0.75 mmol). After agitating the reaction mixtures for 12 h the resins are filtered and washed with DMF, MeOH and CH$_2$Cl$_2$ then dried in vacuo. Each sample is next treated with a solution of tetrakis(triphenylphosphine)-palladium(0) (0.02 mmol) in THF (2 mL) followed by addition of tetrabutylammonium fluoride (0.3 mmol) and azidotrimethylsilane (0.8 mmol) in THF (2 mL). After 30 min. the reactions are drained and the resins washed with CH$_2$Cl$_2$ then dried in vacuo. Each sample is then reacted with 4-chloro-7-nitrobenzofurazan (NCB—Cl, 0.5 mmol) in a 1:1 v/v mixture of DMF and EtOH for 1 h at 65-70° C. The samples are cooled, washed with DMF, MeOH and CH$_2$Cl$_2$ and dried in vacuo. Each resin aliquot is finally treated for 1 h with 1 mL of a 1:1 v/v mixture of TFA and CH$_2$Cl$_2$ to cleave the NBD-containing dipeptides from resin. The 10 samples are dried in vacuo.

II. Screening Sub-Libraries

The various sub-libraries prepared according to the foregoing procedures can then be screened for activity with the transport protein hPEPT1 according to the methods and protocols described in the examples and specification above. Active compounds are isolated and characterized to identify chemical and/or structural motifs common to the active compounds. Such common features indicate elements that are important in conferring activity with PEPT1.

EXAMPLE 5

Distinguishing Between Inhibitors (Surface-Bound Complexes) and Substrates

Internally Quenched Reporters

Certain methods utilize complexes having the general structure R—X—Y—Q, where: X is an actively transported moiety (i.e., a substrate), R is a reporter that includes a fluorescent moiety, Q is a fluorescence quencher moiety (quencher), and Y is a linker, typically an enzymatically labile linker.

Such a complex can be prepared by covalent attachment of a fluorescent moiety (e.g., 2-aminobenzoic acid, 7-methoxycoumarin, etc.) (reporter) to the substrate backbone and attachment of a fluorescence quencher moiety (e.g., O-(2,4-dinitrophenyl)-ethylenediol, N-(2,4-dinitrophenyl)-ethylenediamine, etc.) (quencher) to the substrate backbone by any suitable enzymatically labile linker (e.g., ester, carbonate, carbamate, etc.). Such a compound is not significantly fluorescent due to intramolecular resonance energy transfer between the fluorescent moiety and the quencher. However, intracellular enzymatic cleavage of the labile linker results in loss of the quencher moiety, leading to increased fluorescence of the remaining substrate-reporter conjugate. Hence, such complexes can be used to demonstrate cellular uptake of the substrate moiety. Extracellular fluorescence is generally negligible. A statistically significant increase in fluorescence indicates cellular uptake of the complex and cleavage of the labile linker, thereby releasing the quencher from the reporter to produce the increase in fluorescence.

One example of a suitable conjugate is shown below. This particular conjugate uses 2-aminobenzoic acid as the reporter, O-(2,4-dinitrophenyl)-ethylenediol as the quencher, and contains an esterase labile linker;

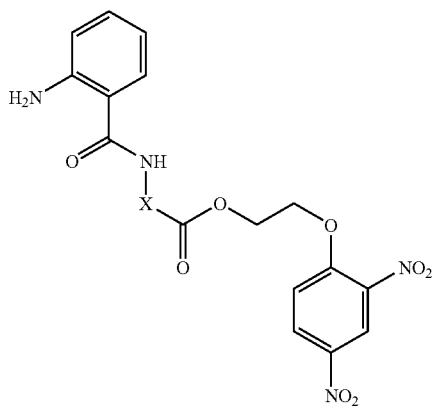

A second suitable conjugate uses 7-methoxycoumarin as the reporter and O-(2,4-dinitrophenyl)-ethylenediol as the quencher, with an esterase labile linker:

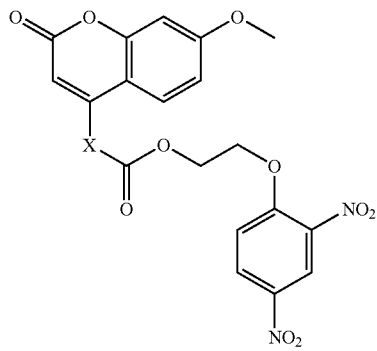

EXAMPLE 6

Distinguishing Between Inhibitors (Surface-Bound Complexes) and Substrates

Reporter Binding to Intracellular Agent

This assay utilizes a "conditional" reporter or tag in which the reporter includes a DNA-binding dye that is not fluorescent until it is transported into the cell by the transporter of interest. Upon entry into the cell, the reporter, either with or without being cleaved from the rest of the complex by intracellular hydrolases, is available to interact with the DNA in the nucleus of the cell. The method is performed as follows:

Day 1: Seed transporter-expressing cells at 100K/well into clear bottom black 96-well tissue culture treated plates.

Day 2: Wash cells 2× with 100 µl appropriate buffer.

Add 50 µl of various concentrations of compounds dissolved in buffer or buffer alone to each well.

Incubate 1 hr. at RT.

Wash each well 4× with 100 µl/well buffer at 4° C.

Add 50 µl/well buffer.

Determine the amount of fluorescent substrate transported by measuring Fluorescent Units (FU) in wells using the Tecan Spectrafluor instrument, measuring from the bottom of the well and using appropriate excitation and emission wavelengths for the particular dyes employed.

CHO K1 cells are used as control for non-transporter dependent transport.

A wide variety of DNA-binding fluorophores can be utilized. The dyes should be cell impermeant so that only when the dye is transported into the cell is the dye available for binding to the cellular DNA. Exemplary cell-impermeant dyes include, but are not limited to, SYTOX Blue, SYTOX Green, SYTOX Orange, POPO-1, BOBO-1, YOYO-1, TOTO-1, JOJO-1, POPO-3, LOLO-1, BOBO-3, YOYO-3, TOTO-3, PO-PRO-1, BO-PRO-1, YO-PRO-1, TO-PRO-1, JO-PRO-1, PO-PRO-3, LO-PRO-3, BO-PRO-3, YO-PRO-3, TO-PRO-3, TO-PRO-5, all of which are commercially-available from Molecular Probes.

EXAMPLE 7

Distinguishing Between Inhibitors (Surface-Bound Complexes) and Substrates

Reporter Includes Substrate for Intracellular Enzyme

Another approach for selective detection of complexes that have been internalized through the action of a transport protein is for the complex to include a substrate for an enzyme that resides within the cells utilized in the assay. As indicated supra, the reporter can include a substrate for a number of different enzymes. The following examples describe methods in which the reporter comprises luciferin, a substrate for luciferase, which enzyme is expressed intracellularly from an exogenous expression cassette.

I. Transfection and Selection of Luciferase Clones

Figure 15:
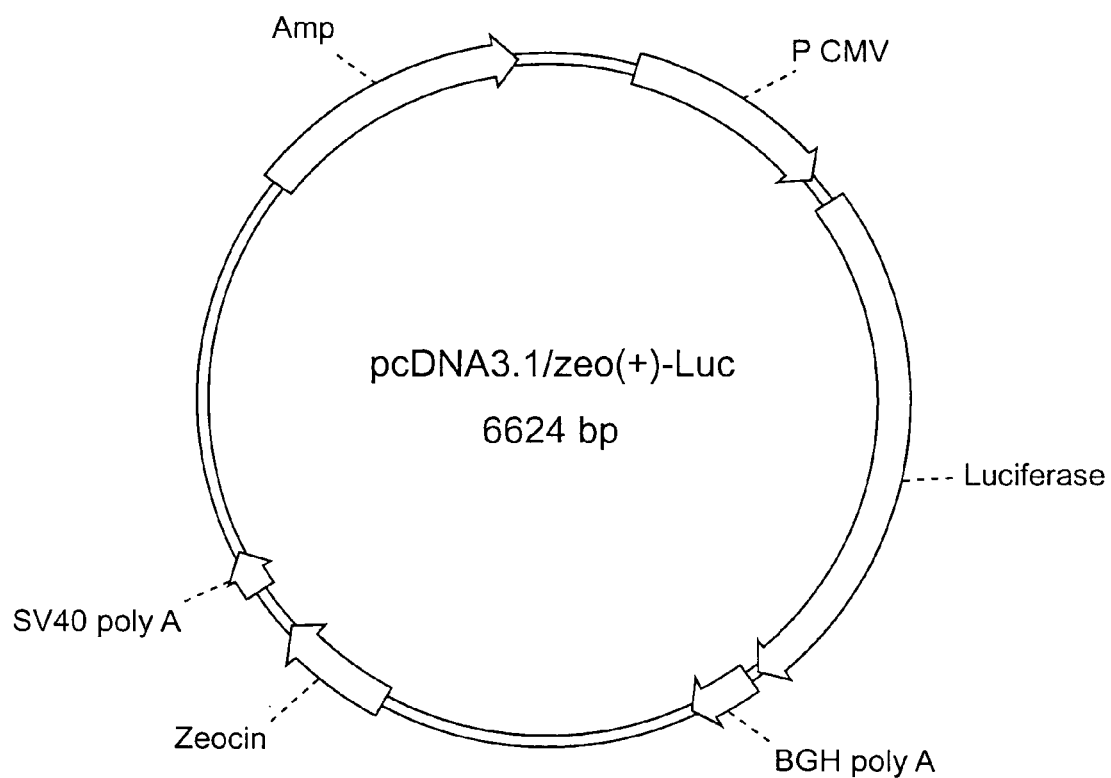
FIG. 15 depicts a luciferase vector construct used to transfect cells such that they express luciferase.

CHO K1 cells ($10^7$/ml) were transfected by electroporation (400V, 250 µfarads) with 40 µg of pcDNA3 luciferase with zeocin as the selectable marker (pcDNA3.1/zeo(+)-Luc (see FIG. 15). After allowing two days for integration of the DNA into the cellular genome, zeocin (0.6 mg/ml) was added. The cells were selected for ten days. The selected population was then cloned using a Cytomation MoFlo flow cytometer gated on the live cell population (forward vs. side scatter). The resultant clones were transferred to replica plates and assayed for luciferase activity. Several clones with high and medium levels of expression were selected for long-term stability studies in the absence of zeocin. Selected clones can be used for expressing transporters that can be selected using an additional selectable marker.

II. Isolation of Clonal Cell Lines Constitutively Expressing Luciferase

Day 1: Cloned cells to be assayed were seeded at 100K cells/well in black clear-bottom 96-well plates. Replica plates were made in clear 96-well plates for use in protein determination assays.

Day 2: Media was removed from wells and cells were washed 2× with 100 µl/well of PBS.

For luciferase assays:
100 µl per well of commercially-available luciferase detection reagent was added to each well (e.g., Steady-Glo (Promega) or Luc-lite (Packard))

The plate containing the cells was shaken for 5 minutes on a plate mixer

Luminescence was detected by reading on a Wallac microbeta scintillation/luminescence microplate reader.

For protein assays:
Cells were solubilized in 30 µl/well of 0.1 NaOH. 10 µl of this solution was removed to a fresh plate and mixed with 200 µl of a 1:5 dilution of BioRad protein assay dye.

After 5 min, absorbance was read at 595 on the Tecan plate reader.

Luminescence from each well was normalized for amount of protein determined in each well. A number of cell lines that efficiently expressed luciferase were identified according to this protocol.

III. General Assay Protocol

Day 1: Cells expressing luciferase and transporter of interest are seeded at 100K/well in black or white clear-bottom 96-well plates.

Day 2: Cells are washed 2× with 100 µl/well of the appropriate buffer for the transporter being studied (HBSS for bile acid, pH 6.0 buffer for PEPT1).

Luciferin-tagged compounds at various concentrations are added in 50 µl assay buffer to the wells and the plate is incubated at RT or at 37° C.

Plates are read on the Wallac Microbeta scintillation/luminescence microplate reader every 20 mins for up to two hours to monitor increase in luciferase-generated light production.

To increase signal by providing excess ATP and Coenzyme A, necessary cofactors for the luminescence assay, 100 µl of assay buffer (made fresh daily) is added to the wells, and the plate is monitored as above on the microplate reader. The assay buffer includes: 0.1 M $KHPO_4$, 1 mM DTT, 2 mM EDTA, 30 mM Tricine, 15 mM $MgSO_4$, 3 mM ATP, 10 mM DTT and 1 mM CoA.

As a positive control to monitor luciferase enzyme activity in lysed cells, 1% Triton X-1000 and 1 mM luciferin is added to the above buffer and plates read as above.

IV. Synthesis of Luciferin Conjugated Substrates for PEPT1

Figure 16:
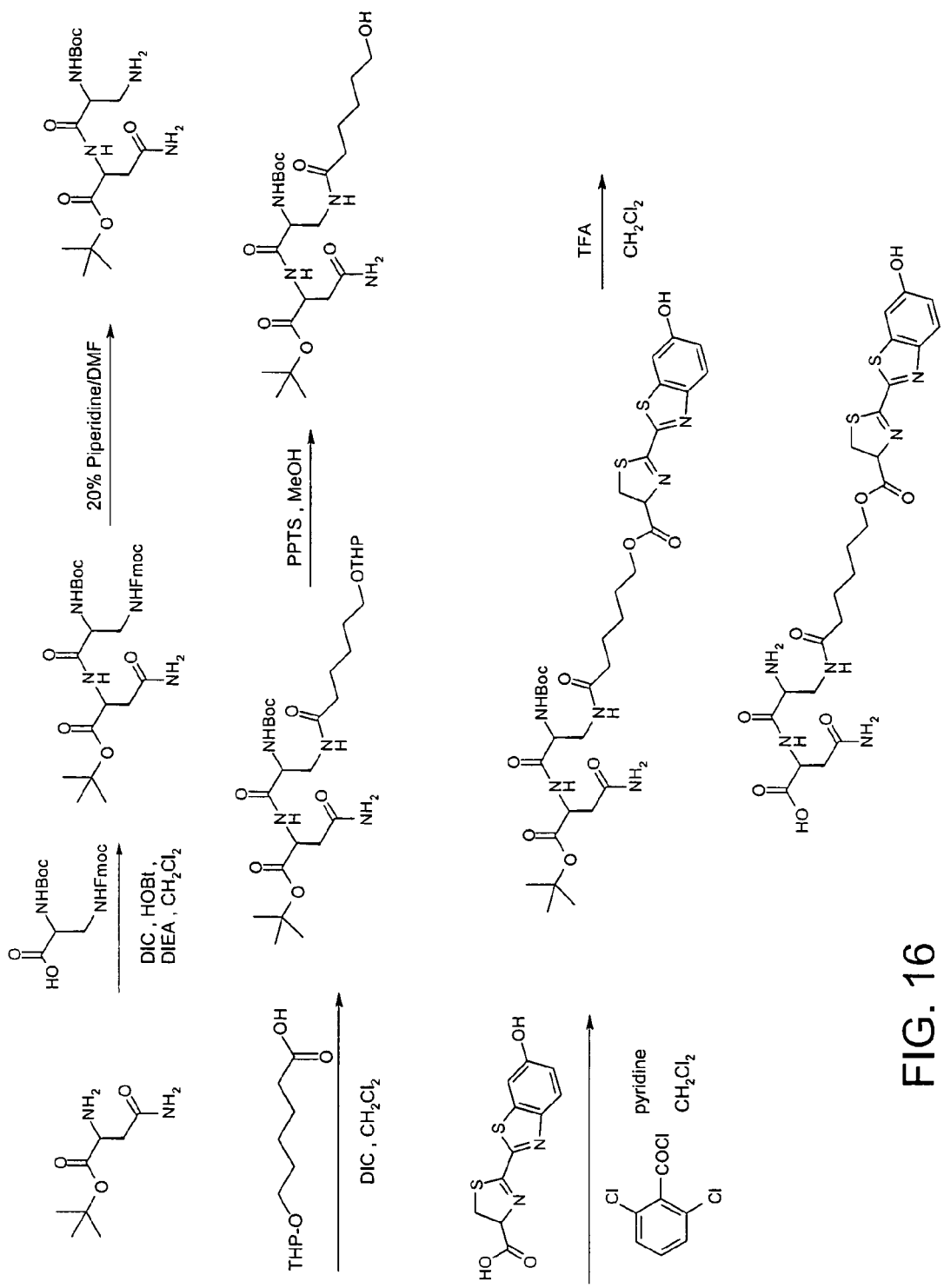
FIGS. 16-18 illustrate the synthesis of various luciferin conjugated substrates.

The main steps in a method for synthesizing a dipeptide conjugated to luciferin (referred to as GP5-71) is set forth in FIG. 16. To a 100 mL round-bottom flask was added asparagine t-butyl ester hydrochloride (675 mg), DIEA (0.52 mL, 1 eq) and dichloromethane (10 mL). α-N-Boc-β-N-Fmoc diaminopropionic acid (1.28 g, 1 eq) and DIC (0.47 mL, 1 eq) were added and the mixture stirred at room temperature for 16 h. The reaction mixture was diluted with dichloromethane (30 mL) and extracted with 1M HCl solution (2×10 mL) then saturated sodium bicarbonate solution (2×10 mL). The organic layer was dried over anhydrous sodium sulfate and the solvent removed in vacuo. 20% piperidine in DMF (5 mL) was added and the reaction mixture stirred at room temperature for min. The solvent was removed in vacuo and column chromatography on silica gel gave the pure dipeptide product (1.0 g, 89% yield based on asparagine t-butyl ester hydrochloride).

This product was dissolved in dichloromethane (10 mL) and 6-tetrahydropyranoxy-hexanoic acid (0.58 g, 1 eq) and DIC (0.42 mL, 1 eq) were added. The mixture was stirred at room temperature for 16 h, then diluted with dichloromethane (30 mL) and extracted with 1M HCl solution (2×5 µL) then saturated sodium bicarbonate solution (2×5 mL). The organic layer was dried over anhydrous sodium sulfate and the solvent removed in vacuo. Methanol (10 mL) and pyridinium p-toluenesulfonate (60 mg) were added to this residue, the reaction mixture was heated at 60° C. for 2 h, and the solvent removed in vacuo. The residue was dissolved in dichloromethane (20 mL) and shaken with saturated sodium bicarbonate solution (2 mL). The organic layer was dried over anhydrous sodium sulfate and the solvent removed in vacuo. Column chromatography on silica gel gave the dipeptide alcohol (636 mg, 49% yield based on 6-tetrahydropyranoxyhexanoic acid).

To a sample of the above alcohol (100 mg) in dichloromethane (2 mL) was added a mixture of D-(−)-2-(6'-hydroxy-2'-benzothiazolyl)-thiazoline-4-carboxylic acid (i.e. D-luciferin) (86 mg, 1.5 eq), 2,6-dichlorobenzoyl chloride (0.029 mL, 3 eq) and pyridine (0.066 mL, 4 eq) in DMF (3 mL). The reaction mixture was stirred at room temperature for 18 h, then diluted with dichloromethane (20 mL) and extracted with 1M HCl solution (2×3 mL) then saturated sodium bicarbonate solution (1×3 mL). The organic layer was dried over anhydrous sodium sulfate and the solvent was removed in vacuo. The luciferin-peptide conjugate was isolated after preparative TLC purification and treated with TFA (5 mL) at room temperature for 4 h. The solvent was removed in vacuo and the product purified by preparative HPLC to afford the desired luciferin-conjugated dipeptide GP5-71 (36 mg, 30% yield based on starting alcohol). Electrospray mass spectrometry showed the expected molecular ion at m/z=595 (M+H$^+$).

Figure 17:
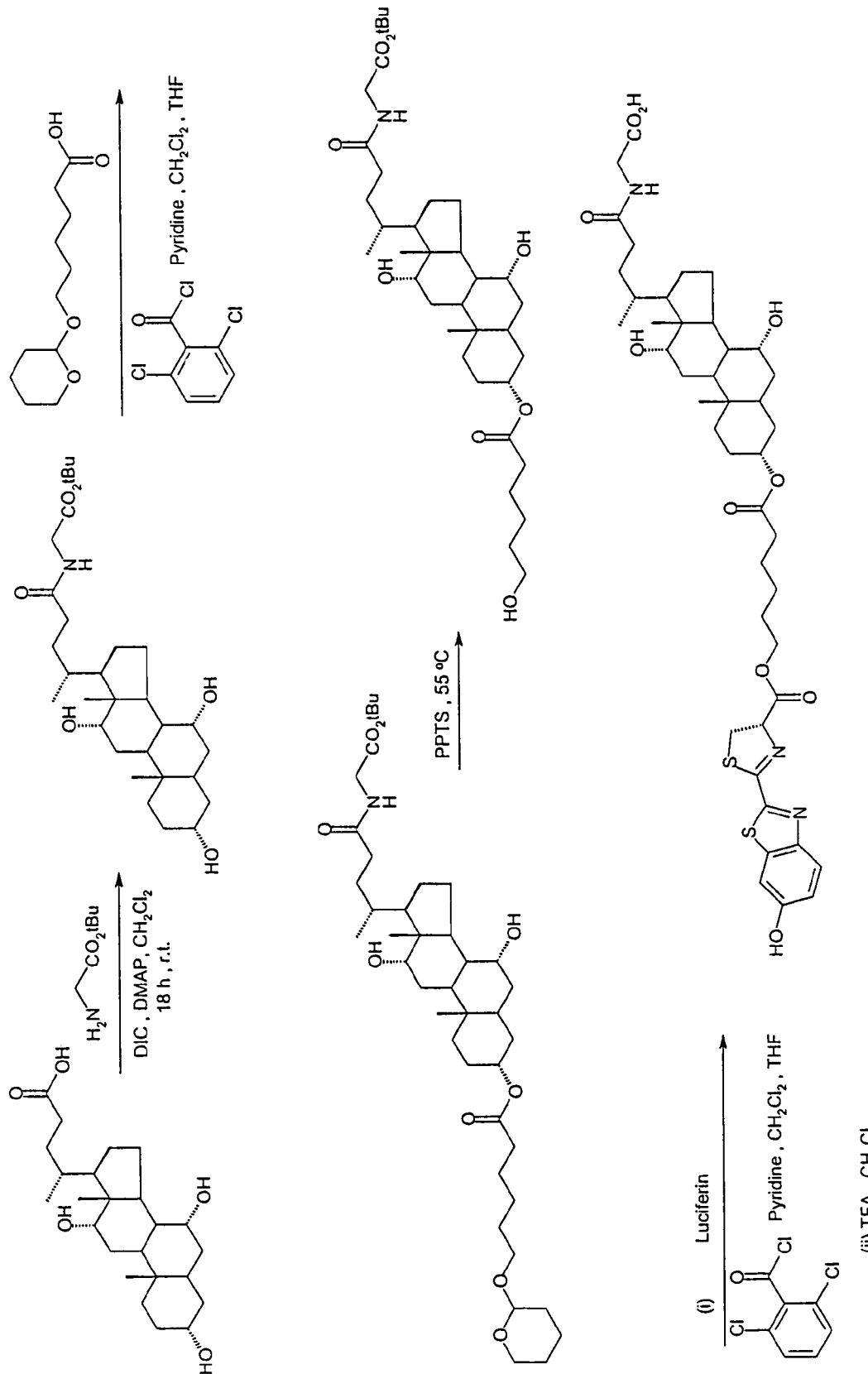

V. Synthesis of Luciferin-Conjugated Substrates for Intestinal or Liver Bile Acid Transport Protein The following synthesis for a luciferin conjugate of glycocholic acid (referred to as CZ15-73) is shown in FIG. 17. Glycocholic acid tert-butyl ester: Cholic acid (408 mg, 1 mmol) was dissolved in dry THF (20 mL) in a 100 mL round-bottom flask provided with a magnetic stirrer. DIC (157 µL, 1 mmol) was added and after 10 minutes, a solution of glycine tert-butyl ester hydrochloride (167 mg, 1 mmol) and DIEA (174 µL, 1 mmol) in dry THF (30 ml) was added dropwise, followed by a catalytic amount of 4-dimethylaminopyridine (10 mg). The reaction mixture was stirred at room temperature for 18 h. Solvent removal in vacuo afforded the crude product, which was dissolved in CH$_2$Cl$_2$ (100 mL) and washed with brine (2×15 mL). The organic phase was dried over MgSO$_4$ and concentrated to give the crude product, which was purified by flash chromatography on silica gel (CH$_2$Cl$_2$-MeOH 95:5) to give pure glycocholate ester (470 mg, 90% yield). Electrospray mass spectrometry showed the expected molecular ion at m/z=522 (M+H$^+$).

6-Tetrahydropyranoxyhexanoic acid: A solution of ethyl 6-hydroxyhexanoate (162 µL, 1 mmol), 3,4-dihydro-2H-pyran (137 µL, 1.5 mmol) and pyridinium p-toluenesulfonate (25 mg, 0.1 mmol) in dry CH$_2$Cl$_2$ (10 mL) was stirred at room temperature for 4 h. The reaction mixture was diluted with CH$_2$Cl$_2$ (10 mL) and washed with brine (2×5 mL). The organic phase was dried over MgSO$_4$ and the solvent removed in vacuo. The residue was treated with aqueous 0.5 M NaOH (10 mL) and MeOH (10 mL) at 55° C. for 2 h. After removal of MeOH and washing with CH$_2$Cl$_2$ (10 mL), the aqueous phase was acidified with citric acid. Extraction with ether (3×15 mL) and concentration of the organic phase gave the protected hexanoic acid product (216 mg, 100% yield). Electrospray mass spectrometry showed the expected molecular ion at m/z=215 (M−H$^-$). This material was used in the next reaction without further purification.

To a solution of 6-tetrahydropyranoxyhexanoic acid (216 mg, 1 mmol) in dry CH$_2$Cl$_2$ (10 mL) was added pyridine (97 µL, 1.2 mmol) followed by 2,6-dichlorobenzoyl chloride (143 µL, 1 mmol). After 10 min. a solution of glycocholic acid tert-butyl ester (418 mg, 0.8 mmol) in dry CH$_2$Cl$_2$ (20 mL) was added dropwise. The reaction mixture was heated to 50° C. with stirring. Additional pyridine/2,6-dichlorobenzoyl chloride (in ratio 1.2:1) was added in several small portions until a trace amount of di-ester was detected by TLC. (TLC analysis: eluent CH$_2$Cl$_2$-MeOH 97:3). The reaction mixture was washed with saturated sodium bicarbonate solution (10 mL) and saturated citric acid solution (2×10 mL). The organic phase was dried over MgSO$_4$ and concentrated in vacuo to give the crude ester, which was purified by flash chromatography on silica gel (CH$_2$Cl$_2$-MeOH 97:3) to give the pure 3-(6-tetrahydropyranoxyhexanoyl)-glycocholic acid tert-butyl ester product (230 mg, 32% yield). Electrospray mass spectrometry showed the expected molecular ion at m/z=742 (M+Na$^+$).

The THP group from the above ester (230 mg, 0.32 mmol) was removed by treatment with pyridinium p-toluenesulfonate (8 mg, 0.032 mmol) in ethanol (10 mL) at 55° C. for 4 h. The solvent was removed in vacuo, and the residue chromatographed on a silica gel column to afford the pure alcohol product (159 mg, 78% yield). Electrospray mass spectrometry showed the expected molecular ion at m/z=636 (M+H$^+$).

To a solution of D-luciferin (50 mg, 0.18 mmol) in dry THF (5 mL) containing pyridine (18 µL, 0.22 mmol) was added 2,6-dichlorobenzoyl chloride (26 µL, 0.18 mmol). After stirring for 10 min. a solution of the above alcohol (117 mg, 0.18 mmol) in dry CH$_2$Cl$_2$ (5 mL) was added dropwise. The reaction mixture was further stirred at room temperature for 48 h. Additional pyridine/2,6-dichlorobenzoyl chloride (in ratio 1.2:1) was added in several small portions to drive the reaction to completion. (TLC analysis: eluent CH$_2$Cl$_2$-EtOAc 60:40). The reaction mixture was diluted with CH$_2$Cl$_2$ (10 mL), then washed with saturated sodium bicarbonate solution (5 mL) and saturated citric acid solution (2×5 mL). The organic phase was dried over MgSO$_4$ then concentrated to give the crude luciferin conjugate, which was purified by using a silica solid phase extraction (SPE) cartridge, eluting sequentially with CH$_2$Cl$_2$ (50 mL), 20% EtOAc/CH$_2$Cl$_2$ (50 mL), 40% EtOAc/CH$_2$Cl$_2$ (50 mL), 60% EtOAc/CH$_2$Cl$_2$ (50 mL), and 80% EtOAc/CH$_2$Cl$_2$ (50 mL). The tert-butyl ester product was collected in the 80% EtOAc/CH$_2$Cl$_2$ fraction, which upon concentration in vacuo gave the desired thiazoline product (118 mg, 73% yield) contaminated with 30% (by weight) of the oxidized thiazole adduct. Electrospray mass spectrometry showed the expected molecular ion at m/z=898 (M+H$^+$) for the thiazoline and m/z=896 (M+H$^+$) for the oxidized thiazole product.

This tert-butyl ester (118 mg, 0.13 mmol) was treated with a mixture of trifluoroacetic acid/CH$_2$Cl$_2$/H$_2$O (50:49:1, 5 mL) at room temperature for 4 h. After removal of solvent in vacuo, the resulting residue was treated with 50% piperidine in CH$_2$Cl$_2$ at room temperature for 30 min. The solvent was removed in vacuo and the residue dissolved in CH$_2$Cl$_2$ (10 mL) and extracted with saturated sodium bicarbonate solution (20 mL). The aqueous phase was collected, acidified with citric acid then extracted again with EtOAc (3×20 mL). The combined organic phases were dried over anhydrous sodium sulfate and concentrated in vacuo. The desired luciferin-glycocholate ester product CZ15-73 was isolated by preparative TLC (eluent: 5% HOAc/EtOAc), and further purified by preparative HPLC (column: Phenomenex, luna C18; mobile phase: H$_2$O/MeOH) to give the pure conjugate (18 mg, 22% yield). Electrospray mass spectrometry showed the expected molecular ion at m/z=842 (M+H$^+$).

VI. Synthesis and Screening of Library of Bile Acid-Luciferin Conjugates

A. Synthesis

Figure 18:
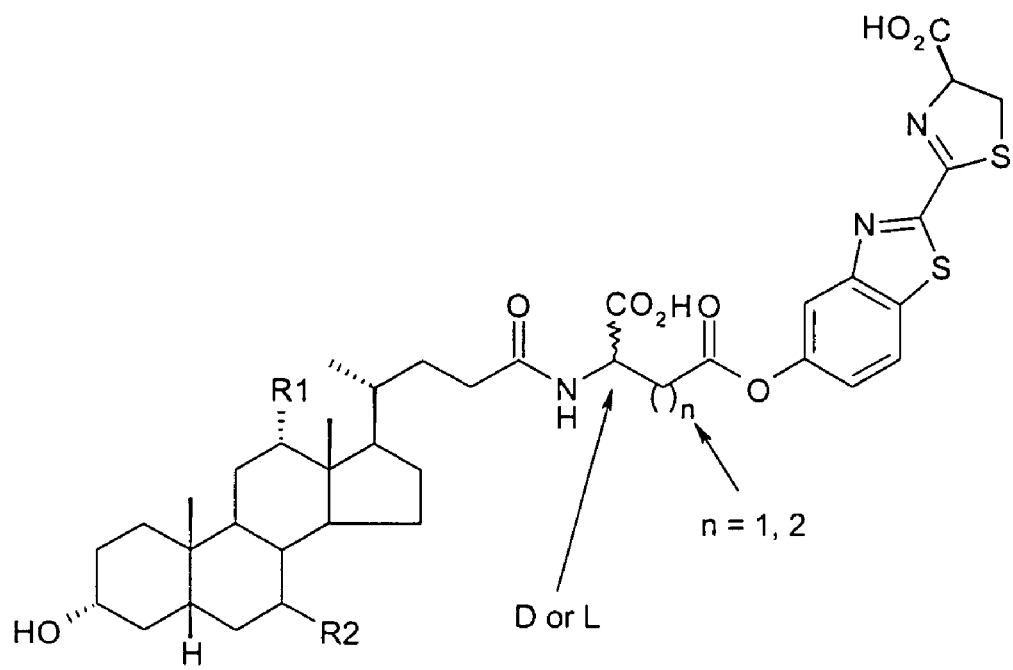

A method for synthesizing a library of bile acid-luciferin conjugates is shown in FIG. 18. To 0.5 g of Wang resin (Novabiochem) (loading ~1 mmole/g) is added 5 mL of a DMF solution containing D-luciferin (Sigma) (2.5 mmol), HATU (2.5 mmol) and DIEA (5 mmol). The suspension is stirred for 8 h and the resin washed with DMF (3×). The resin is shaken for 30 min with 5 mL of a 0.2 M solution of potassium carbonate in 50% aqueous MeOH to hydrolyze any phenolic ester formed, and then washed with DMF, CH$_2$Cl$_2$, MeOH, and CH$_2$Cl$_2$ again, then dried in vacuo. The resin is divided into 4 equal portions and then treated with 5 mL of a DMF solution containing 1 mmol of either (i) N-α-Fmoc-L-aspartic acid-α-tert-butyl ester, (ii) N-α-Fmoc-D-aspartic acid-α-tert-butyl ester, (iii) N-α-Fmoc-L-glutamic acid-α-tert-butyl ester or (iv) N-α-Fmoc-D-glutamic acid-α-tert-butyl ester, together with diisopropylcarbodiimide (DIC, 0.5 mmol) and DMAP (0.1 mmol). After stirring for 4 h, the resins are washed with DMF (3×).

Each batch of resin is next treated with 1 mL of a 5% (v/v) solution of DBU in DMF for 20 min then washed with DMF (3×), CH$_2$Cl$_2$, MeOH, and CH$_2$Cl$_2$ again, then dried in vacuo.

The four resin samples are each divided into five equal aliquots for coupling to one of five different bile acids (i.e. cholic acid, deoxycholic acid, chenodeoxycholic acid, ursodeoxycholic acid and lithocholic acid). These reactions contained 0.2 mmol of the bile acid in DMF (2 mL) with HATU (0.2 mmol) and DIEA (0.4 mmol), and after 4 h, the resins are washed with DMF (3×), $CH_2Cl_2$, MeOH, and $CH_2Cl_2$ again, then dried in vacuo. Each of the 20 samples is cleaved from resin by treatment with 1 mL of a 50% (v/v) solution of TFA in $CH_2Cl_2$ for 1 h, the resins washed with $CH_2Cl_2$ (0.5 mL) and the filtrates evaporated to dryness using a Genevac concentrator.

B. Screening of Bile Acid-Luciferin Conjugates

CHO cell lines expressing the human ileal sodium bile acid cotransporter transfected with a vector directing the expression of firefly luciferase are prepared as described in sections I and II of this example. A parental CHO-K1 cell line also expressing firefly luciferase is utilized as a negative control. The library of bile acid-luciferin conjugates synthesized in section VI.A of this example are screened according the protocol described in section III of this example. Samples that give selective emission from the ABST-expressing cells are identified as substrates for the ileal bile acid cotransporter.

EXAMPLE 8

Distinguishing Between Inhibitors (Surface-Bound Complexes) and Substrates

Masked Fluorescent Dipeptides

The following methods describe approaches for synthesizing fluorescent dipeptides that can be utilized to study transport into a cell expressing the PEPT1 transport protein. The following compounds include a "masked" hydroxy-coumarin moiety; this masking moiety is cleaved from the compound by an intracellular esterase to yield a hydroxy-coumarin derivative that fluoresces strongly.

I. Synthesis of the Conditionally Fluorescent Dipeptide GP5-75-2

Figure 19:
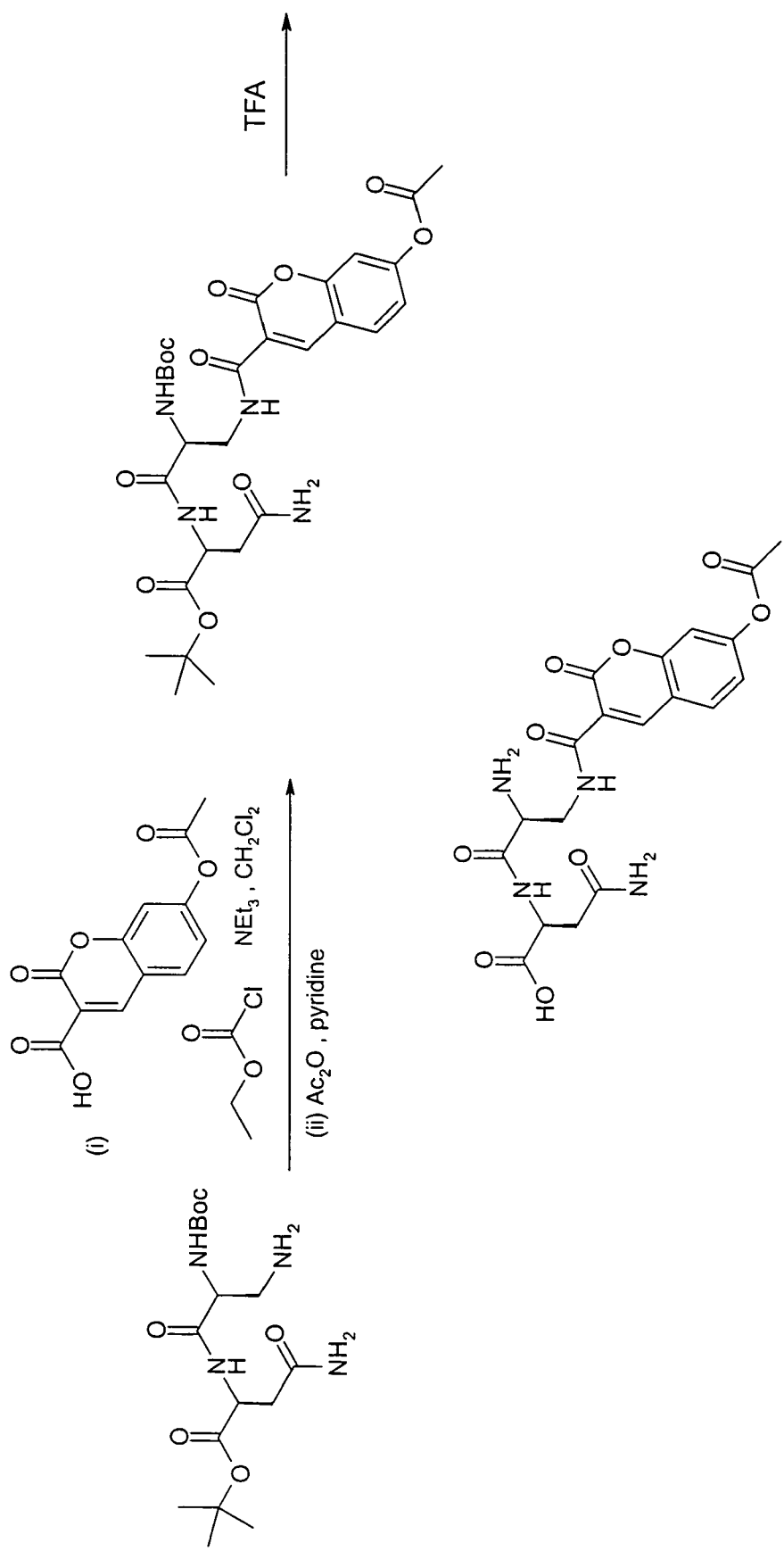
FIGS. 19-21 present the synthesis of conditionally fluorescent substrates that include mask moieties that mask signal formation until the substrate has been internalized within a cell.

The major steps in synthesizing this "masked" dipeptide are shown in FIG. 19. To a 100 mL round-bottomed flask was added asparagine t-butyl ester hydrochloride (675 mg), DIEA (0.52 mL, 1 eq) and dichloromethane (10 mL). α-N-Boc-β-N-Fmoc diaminopropionic acid (1.28 g, 1 eq) and DIC (0.47 mL, 1 eq) were added and the mixture stirred at room temperature for 16 h. The reaction mixture was diluted with dichloromethane (30 mL) and extracted with 1M HCl solution (2×10 mL) then saturated sodium bicarbonate solution (2×10 mL). The organic layer was dried over anhydrous sodium sulfate and the solvent removed in vacuo. 20% piperidine in DMF (5 mL) was added and the reaction mixture stirred at room temperature for 5 min. The solvent was removed in vacuo and column chromatography on silica gel gave the pure dipeptide product (1.0 g, 89% yield based on asparagine t-butyl ester hydrochloride).

7-Acetoxycoumarin-3-carboxylic acid (51 mg) was dissolved in dichloromethane (2 mL) containing triethylamine (43 μL, 1.5 eq) and the reaction mixture cooled to 0° C. Ethyl chloroformate (20 μL) in dichloromethane (0.5 mL) was added, and after stirring at 0° C. for 10 min, this solution was added to a sample of the above dipeptide (76 mg, 1 eq). After stirring at 0° C. for 30 min, the reaction mixture was diluted with dichloromethane (10 mL) and extracted with 1M HCl solution (2 mL) then saturated sodium bicarbonate solution (2 mL). The organic layer was dried over anhydrous sodium sulfate and the solvent removed in vacuo. Acetic anhydride (2 mL) and pyridine (2 mL) were added to this residue and after stirring at room temperature for 20 min., the solvent was again removed in vacuo. The protected conditionally fluorescent dipeptide was purified by preparative TLC and then treated with TFA (3 mL) for 4 h. Solvent was removed in vacuo to afford the conditionally fluorescent dipeptide GP5-75-2. Electrospray mass spectrometry showed the expected molecular ion at m/z=449 (M+H$^+$).

II. Synthesis of the Conditionally Fluorescent Dipeptide GP5-77

Figure 20:
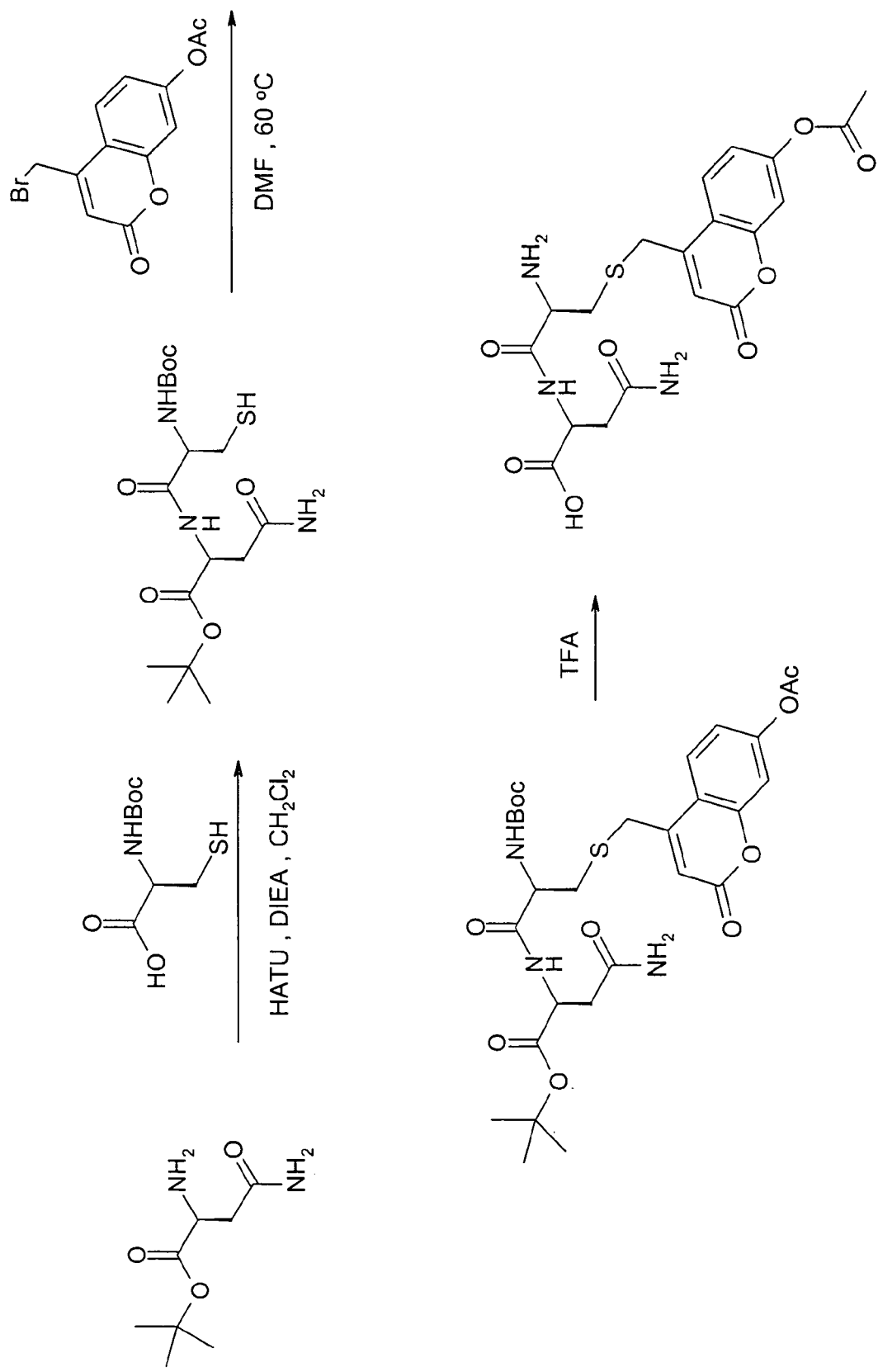

The synthesis of this masked dipeptide is set forth in FIG. 20. To a 100 mL round-bottomed flask was added asparagine t-butyl ester hydrochloride (564 mg), DIEA (1.04 mL, 2 eq) and dichloromethane (20 mL). N-Boc-Cys-OH (660 mg, 1 eq) and HATU (1.14 g, 1 eq) were added and the mixture stirred at room temperature for 16 h. The reaction mixture was diluted with dichloromethane (30 mL) and extracted with 1M HCl solution (2×10 mL) then saturated sodium bicarbonate solution (2×10 mL). The solvent was removed in vacuo and column chromatography on silica gel gave the pure dipeptide product (1.04 g, 89% yield based on asparagine t-butyl ester hydrochloride).

A sample of the above dipeptide (250 mg) was dissolved in DMF (2 mL) and 7-acetoxy-4-(bromomethyl)-coumarin (190 mg) added. The mixture was heated at 60° C. for 14 h and the solvent was removed in vacuo. The protected conditionally fluorescent dipeptide was purified by column chromatography on silica gel and then treated with TFA (2 mL) for 5 h. Solvent was removed in vacuo to afford the conditionally fluorescent dipeptide GP5-77. Electrospray mass spectrometry showed the expected molecular ion at m/z=452 (M+H$^+$).

III. Synthesis of the Conditionally Fluorescent Dipeptide GP5-00

Figure 21:
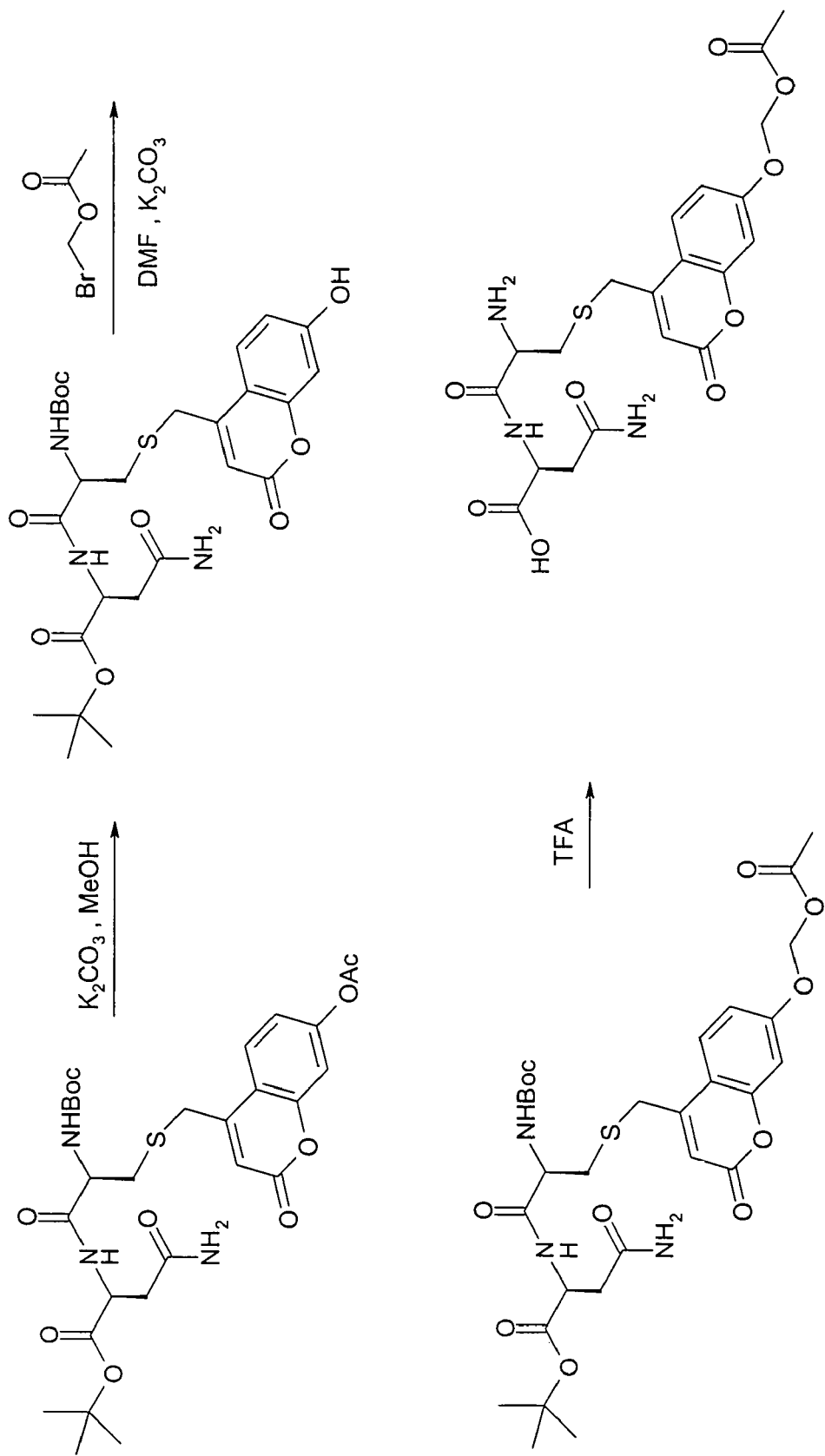

A sample of the protected dipeptide prepared as just described in section II of this example (93 mg) was stirred in MeOH (5 mL) with potassium carbonate (30 mg, 1.1 eq) at room temperature for 2 h (see FIG. 21). The solvent was removed in vacuo and dry DMF (5 mL) and additional potassium carbonate (30 mg, 1.11 eq) added to the residue. Bromomethyl acetate (30 mg, 1 eq) in dry DMF (1 mL) was added dropwise and the reaction mixture stirred at room temperature for 4 h. The solvent was removed in vacuo and the residue dissolved in dichloromethane and shaken with saturated sodium bicarbonate solution (2 mL). The organic layer was dried over anhydrous sodium sulfate and the protected conditionally fluorescent dipeptide purified by column chromatography on silica gel. The product was treated with TFA (1 mL) for 1 h and the solvent removed in vacuo to afford the conditionally fluorescent dipeptide GP5-00. Electrospray mass spectrometry showed the expected molecular ion at m/z=482 (M+H$^+$).

EXAMPLE 9

Distinguishing Between Inhibitors (Surface-Bound Complexes) and Substrates

Detection by Microscopy

Day 1: Seed CHO hPEPT1 cells at 100K/well into clear bottom black 96-well tissue culture treated plates.

Day 2: Wash cells 2× with pH 6.0 buffer (1 mM $CaCl_2$, 1 mM $MgCl_2$, 150 mM NaCl, 3 mM KCl, 1 mM $NaH_2PO_4$, 5 mM D-glucose and 5 mM MES) at RT.

Add 50 µl of 1 mM XP10486 (NBD-labeled DAP-Asn dipeptide) in pH 6.0 buffer to cells.

Incubate 1 hr at RT. Wash 2×100 µl/well with pH 6.0 buffer at 4° C. Add 100 µl/well of the same buffer, let sit for 10 min. at RT. Wash 2×100 µl/well with pH 6.0 buffer at 4° C. This washing procedure helps minimize the non-specific adherence of fluorescent compounds to the outside of the cells.

Add 50 µl of 10 µg/ml of Texas Red-labeled Wheat-germ agglutinin (in HBSS buffer) to cells and incubate at 4° C. for 30 min. This reagent binds to the glycosylated proteins on the surface of the cells.

Wash cells 2× with 100 µl/well with HBSS buffer at 4° C. Add 50 µl of cold HBSS buffer to each well.

Image each well with the Universal Imaging Automated Fluorescent Microscope System with a 10× objective using appropriate excitation and emission filters for the two fluorophores.

Untransfected CHO K1 cells used as control for non-transporter dependent transport.

EXAMPLE 10

Reporter as Surrogate for Pharmaceutical Agent

The screening methods described herein provide a way to screen for activity of conjugates between substrates and pharmaceutical agents with particular transport proteins without having to develop a specific screen for the pharmaceutical agent of interest. In screening methods utilizing reporter-substrate complexes, the reporter can be viewed as serving as a surrogate for a wide variety of pharmaceutical agents. Initially screening complexes with reporter rather than pharmaceutical agent has the advantage that the reporter is easily detectable whereas the pharmaceutical agent frequently is not. Once it has been demonstrated that a complex including a reporter is a substrate for a transport protein, a pharmaceutical agent (typically having similar physical and chemical characteristics) can be substituted for the reporter and activity retested.

The following syntheses (syntheses I.A., I.B. and I.C.) illustrate the application of this concept. Conjugation of the NBD reporter group to the epsilon amino group of cholyl-lysine generates a fluorescent substrate (synthesis I.A. below) for the intestinal bile acid transporter that is effectively absorbed orally in rat. The analogous compound in which the NBD moiety is replaced by the anti-inflammatory pharmaceutical agent Naproxen (as an epsilon carboxamide; synthesis I.B. below) affords a conjugate that also serves as a bile acid substrate, and upon oral absorption is hydrolyzed (by some uncharacterized amidase activity) to release the parent naproxen. This observation can be further extended to provide an oral propharmaceutical agent of the anti-Parkinson's agent L-Dopa, where the structural analogy between NBD-Lysine and L-Dopa (another α-amino acid) indicates a strategy for conjugating the pharmaceutical agent to cholic acid to afford an orally absorbed substrate of the bile acid transporter (see synthesis I.C.).

Once the reporter is substituted with a pharmaceutical agent, techniques for detecting transport of the substrate/pharmaceutical agent are needed because, as just noted, often the pharmaceutical agent is not readily detectable. Sections II.A. and II.B. of this example describe two approaches that permit the facile detection of substrate/pharmaceutical agents that have been internalized within a cell. One approach utilizes a liquid chromatography (LC) and mass spectroscopy (MS) to detect transport, more specifically LC/MS/MS (section II.A.). A trans-stimulation approach can also be used; this technique is described supra, illustrated in FIG. 4 and described further in Example 11.

Figure 22:
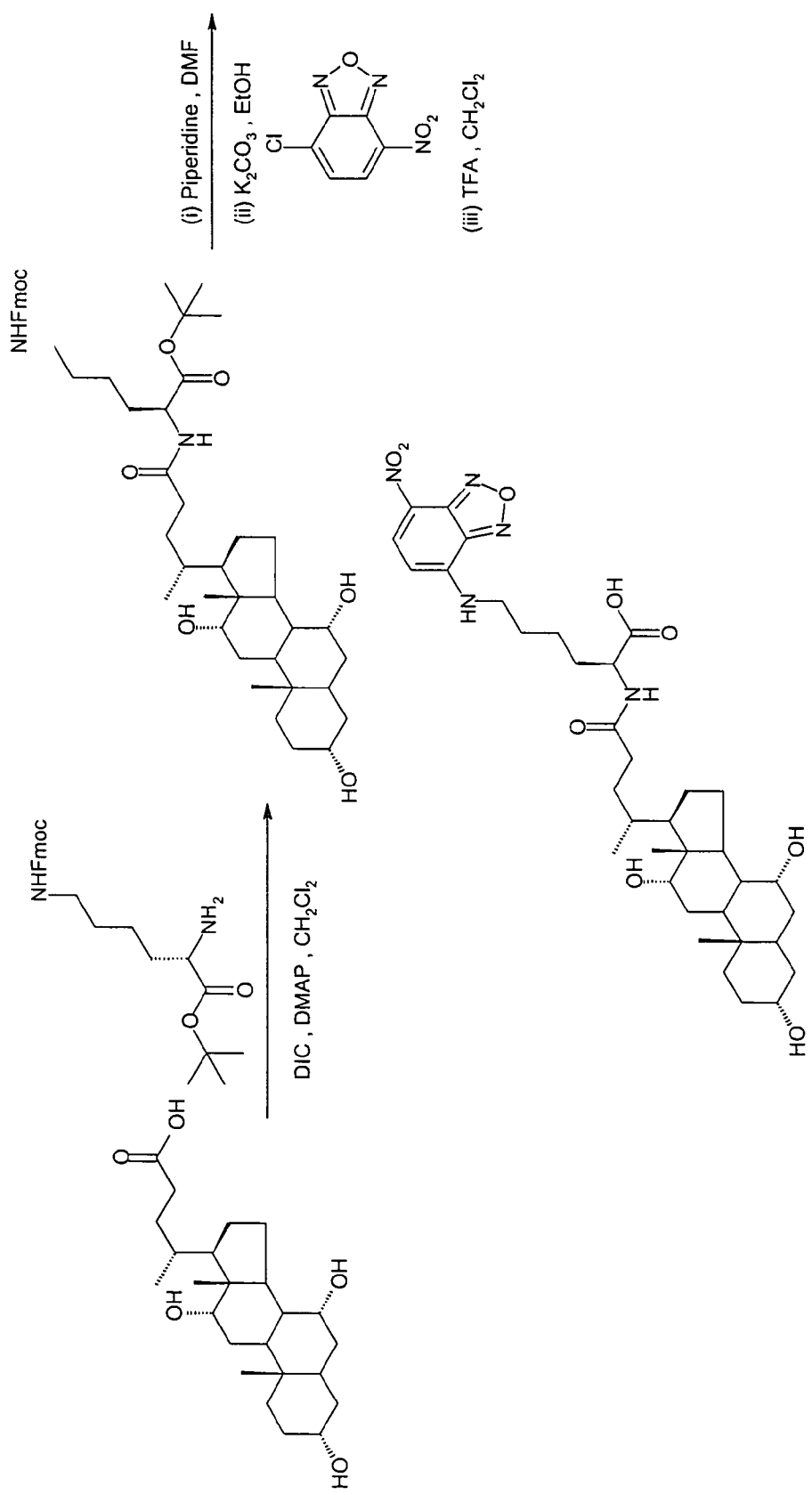
FIGS. 22-24 describe the process of synthesizing complexes in which a pharmaceutical agent is substituted for a reporter in a complex.

I. Synthesis of Complexes in which Pharmaceutical Agent is Substituted for Reporter A. Synthesis of Cholyl-Lysine-(ε-NBD)-OH FIG. 22 depicts the major steps in the synthesis of this complex that includes the NBD reporter. Cholic acid (408 mg, 1 mmol) was dissolved in dry THF (20 mL) in a 100 mL round-bottom flask provided with a magnetic stirrer. DIC (157 µL, 1 mmol) was added and after 10 min., a solution of lysine-ε-N-Fmoc-tert-butyl ester hydrochloride (410 mg, 1 mmol) and DIEA (174 µL, 1 mmol) in dry THF (30 mL) was added dropwise. The reaction mixture was stirred at room temperature for 18 h. The solvent was removed in vacuo and the residue dissolved in $CH_2Cl_2$ (100 mL) and washed with brine (2×15 mL). The organic phase was dried over $MgSO_4$ and concentrated to give the crude product, which was purified by flash chromatography on silica gel ($CH_2Cl_2$-MeOH 95:5) to give pure protected cholyl-lysine conjugate (720 mg, 90% yield). The product was treated with 20% v/v piperidine in DMF (5 mL) for 20 min. and the solvent removed in vacuo. The residue was treated with 4-chloro-7-nitrobenzofurazan (NCB—Cl, 0.22 g, 1.1 eq) in ethanol (15 mL) at 55° C. for 1 h, then cooled to room temperature and the solvent was removed in vacuo. The protected NBD conjugate was purified by chromatography on silica gel then treated in 1:1 v/v TFA/$CH_2Cl_2$ for 1 h at room temperature. The solvent was removed in vacuo to afford cholyl-lys-(ε-NBD)-OH (550 mg, 80% yield). Electrospray mass spectrometry showed the expected molecular ion at m/z=686 (M+H$^+$).

B. Synthesis of Cholyl-Lysine-(ε-Naproxen)-OH

Figure 23:
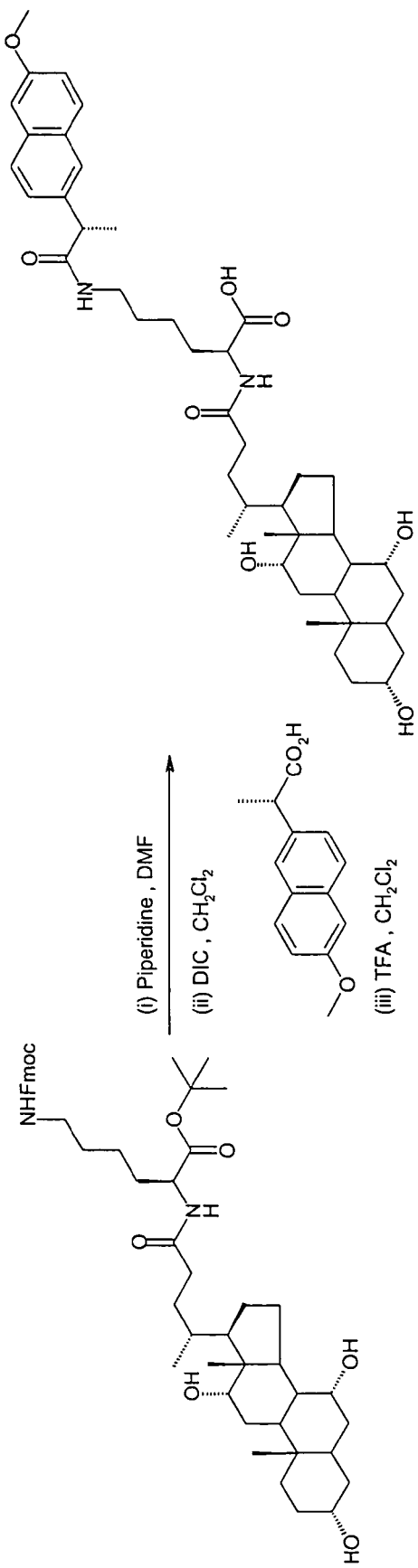

FIG. 23 shows the primary steps in preparing this complex in which the pharmaceutical agent Naproxen is substituted for NBD reporter. Cholyl-Lys-(ε-Fmoc)-O$^t$Bu (400 mg, 0.5 mmol) prepared as described above is treated with 20% v/v piperidine in DMF (5 mL) for 20 min. and the solvent removed in vacuo. The residue is dissolved in dichloromethane (10 mL) and a solution containing DIC (80 µL, 0.5 mmol), naproxen (127 mg, 0.5 mmol) and DIEA (87 µL, 0.5 mmol) in dichloromethane (10 mL) is added dropwise. The reaction mixture is stirred at room temperature for 18 h and the solvent removed in vacuo. The product is purified by column chromatography on silica gel and then treated with a 1:1 v/v mixture of TFA/$CH_2Cl_2$ (5 mL) for 1 h. The solvent is removed in vacuo to afford pure cholyl-lysine-ε-naproxen)-OH (280 mg, 75% yield). Electrospray mass spectrometry shows the expected molecular ion at m/z=749 (M+H$^+$).

C. Synthesis of Cholyl L-Dopa

Figure 24:
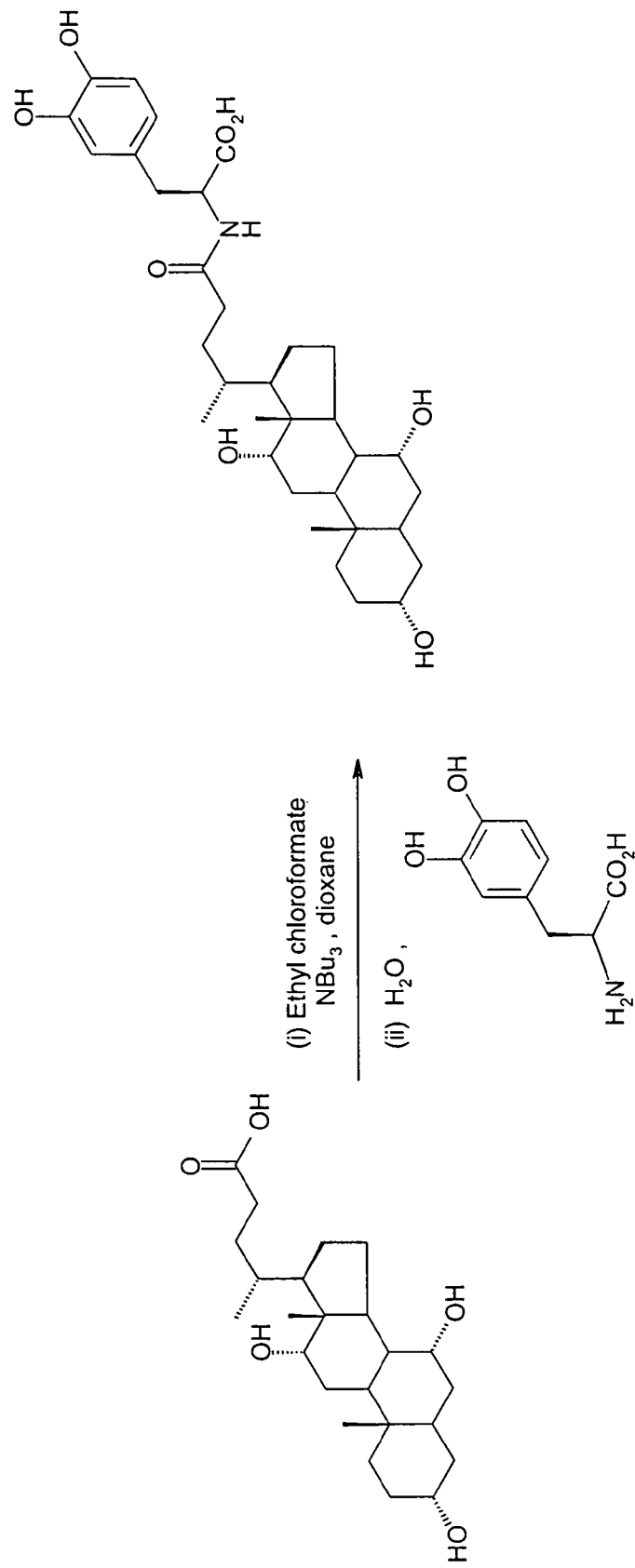

This compound is synthesized according to the steps shown in FIG. 24. Cholic acid (10 mmol) is dissolved in dry dioxane (100 mL) containing tri-n-butylamine (20 mmol), cooled to 0° C., and ethyl chloroformate (10 mmol) added dropwise. After stirring for 20 min a solution of L-Dopa (20 mmol) in 2 M aqueous NaOH (10 mL) is slowly added and the mixture warmed to room temperature with stirring for 2 h. The mixture is poured into water (200 mL), neutralized with 1M aqueous HCl, and extracted thoroughly with ethyl acetate containing 5% (v/v) methanol. The organic layer is dried over $MgSO_4$ and chromatographed on silica gel to afford the pure cholyl-L-Dopa.

EXAMPLE 11

Detecting Internalization of Complexes that Lack Reporters

I. Determination of Complex Internalization by LC/MS/MS

Control CHO K1 cells or PEPT1-transfected, epitope-tagged CHO EE 412 cells (Covitz, et al., (1998) *Biochemistry* 37:15214-15221) (100,000 cells per well) were exposed to 50 µL of 200 µM Gly-Sar in pH 6.0 buffer (1 mM $CaCl_2$, 1 mM $MgCl_2$, 150 mM NaCl, 3 mM KCl, 1 mM $NaH_2PO_4$, 5 mM D-glucose and 5 mM MES) for 0, 10, 20, 30, 40, 50, 60, 70, 80 minutes. Cells were washed twice with 100 µL of pH 6.0 buffer to remove extracellular Gly-Sar. Washed cells were then lysed before analysis by addition of 100 µL of water followed by sonication for 5 min. A standard curve was constructed in blank (untreated) lysed cells. A stock solution of Gly-Sar (1 M) was prepared in HPLC grade water and diluted 1:100 to provide a 10 mM working stock solution. This solution was further diluted to 10 µM solution using water. A serial dilution of 1:2 was then performed to produce final standard solutions with Gly-Sar concentrations ranging from 0.039 to 10 µM.

One hundred microliters of each of these standards were added to a 96 well plate containing blank CHO K1 cells or blank CHO EE 412 cells (100,000 cells per well) followed by sonication for 5 min to lyse the cells. All lysed cell samples (treated and control) were then transferred to 200 µL vials and analyzed using an API 2000 LC/MS/MS system (PE Sciex) equipped with a TurboIonSpray source, an Model 1100 binary pump system (Agilent), and temperature controlled autosampler. The analytical column was a BDS Hypersil 2*50 mm column (Keystone) heated to 45° C. The mobile phase consisted of 0.1% formic acid in water (A) and acetonitrile/0.1% formic acid (B). The gradient condition was 5% B for 1 min, increasing to 90% B over 0.2 min, maintained for 2.8 min, and returning to 5% B for 2 min. The analysis was performed in positive ion mode and an MRM transition of 147/90 was used to selectively detect Gly-Sar. The injection volume was 10 µl.

Figure 25:
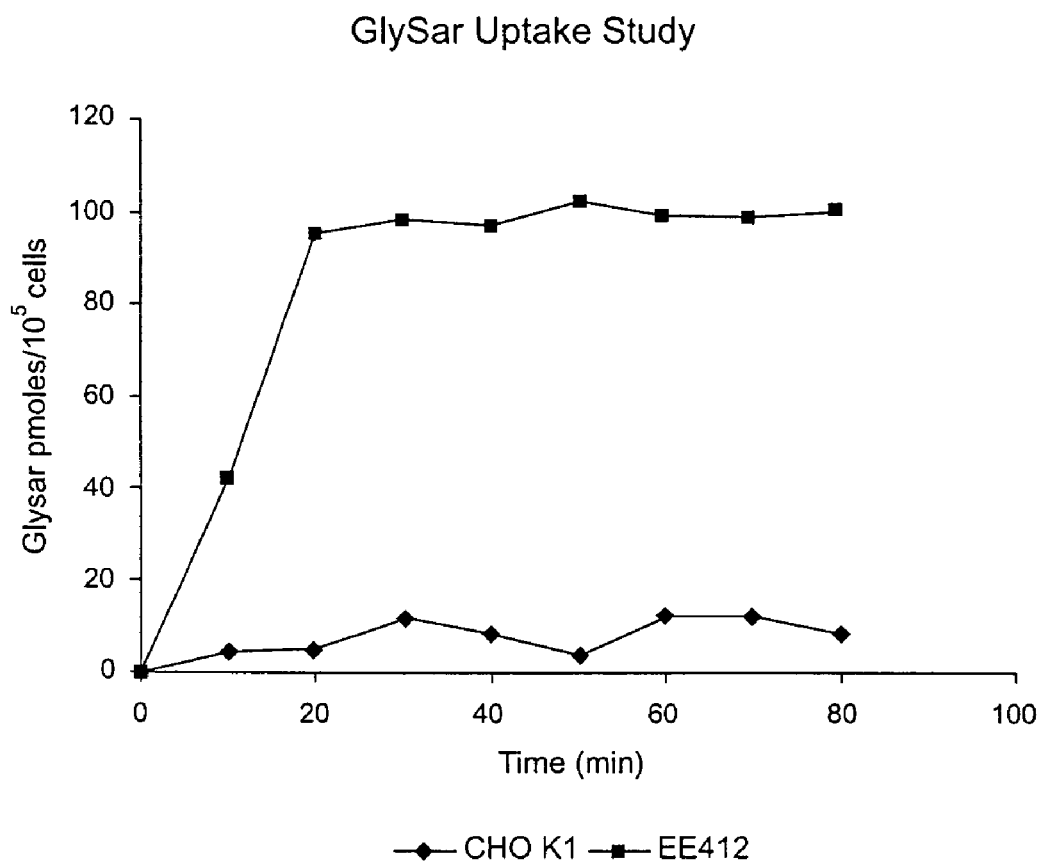
FIG. 25 shows the results of a LC/MS/MS analysis used to determine uptake of the unlabeled substrate Gly-Sar (Glycylsarcosine) in PEPT1-transfected CHO EE 412 test cells and CHO K1 control cells not expressing PEPT1.

The resulting chromatograms were integrated using Analyst™ quantitation software (PE Sciex). The analytical method was linear over the Gly-Sar concentration range of 3.9 pmoles/$10^5$ cells to 1 nmole/$10^5$ cells. The detection limit was 3.9 pmoles/$10^5$ cells (0.39 pmoles on-column). Results are shown in FIG. 25 and demonstrate the ability to monitor uptake of substrate lacking reporter into the cells.

II. Detection of Complex Internalization by Trans-Stimulation

A. Protocol

1. Plate cells expressing IBAT, LBAT, or PEPT1 in 96-well white clear bottom plates (100,000 cells/well). Let attach overnight.

2. Wash cells 2× with HSBS (bile acid) or pH 6.0 buffer (PEPT1)-no serum.

3. Load cells with $^3$H labeled substrates (bile acids-taurocholate, 200,000 cpm/well-2 µM unlabeled taurocholate, in HSBS, 60 min., room temp.) or (PEPT1-GlySar, 200,000 cpm/well-200 µM unlabeled GlySar, in pH 6.0 buffer, 60 min., room temp.).

4. Wash cells 6-8× (over a total 10 min. period) with solutions from step 2.

5. Aspirate wash solution. Transfer solutions containing unlabeled test compounds to the pre-loaded cells using the Cybi-Well transfer apparatus (120 µL/well).

6. Measure $^3$H-labeled substrate efflux at room temperature. Remove 40 µL from each well using the Cybi-Well transfer apparatus (at 10 minutes and 15 minutes) for scintillation counting. Also measure radioactive substrates remaining in the cells. Normalize efflux to the total amount of uptake (CPM efflux+CPM remaining in cells) to control for well-to-well variability in cell number.

7. For both bile acid and peptide transporters, saturating concentrations of unlabeled transported substrates in the medium during the efflux assay stimulate release of 3H-labeled compounds by 2-3 fold. Non-transported antagonists do not stimulate efflux.

B. Results

Figure 26B:
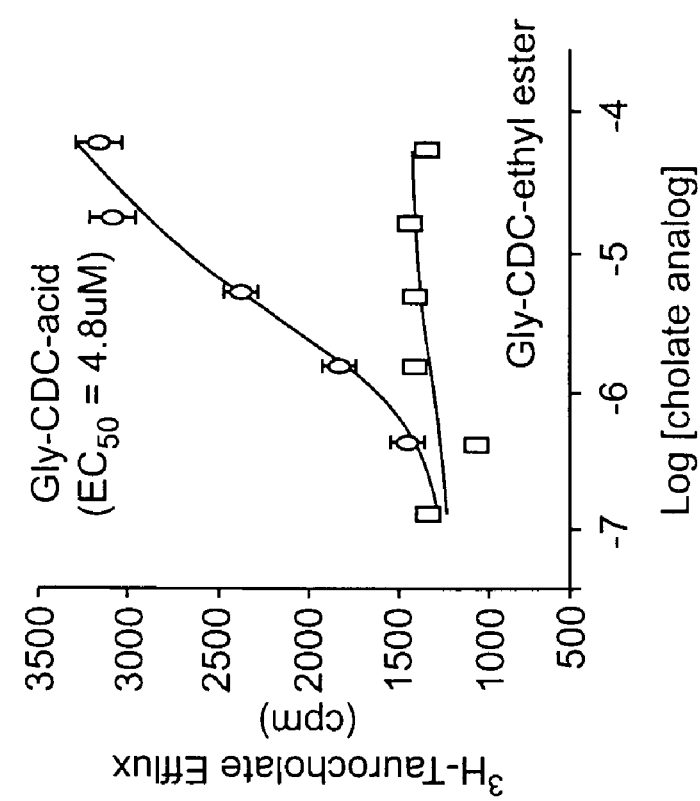
FIGS. 26A and 26B are charts showing the results of trans-stimulation assays.
Figure 26A:
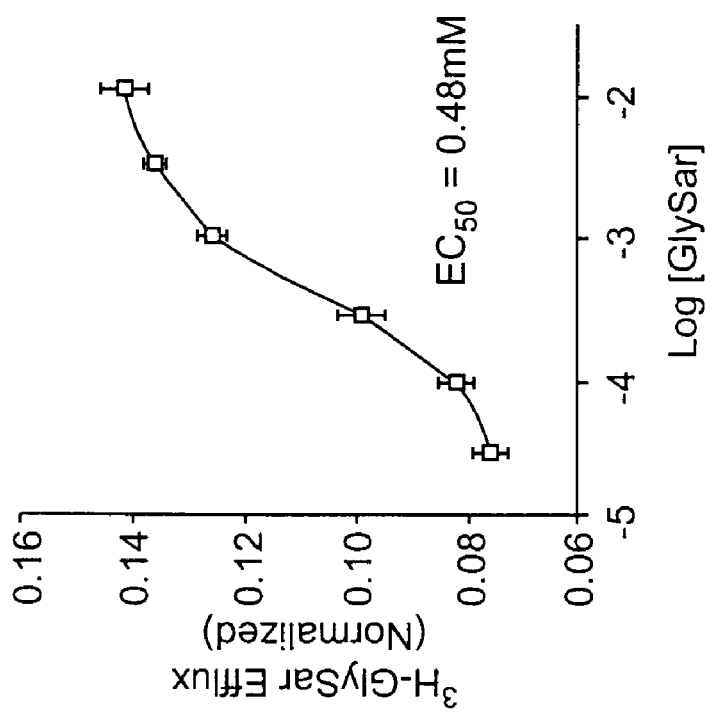

Results for trans-stimulation assays conducted with CHO cells expressing PEPT1 and contacted with tritiated Gly-Sar and unlabeled Gly-Sar are shown in FIG. 26A. The results shown in this figure show the efflux of tritiated Gly-Sar once the cells were contacted with various concentrations of untritiated Gly-Sar. Similar experimental results performed with CHO cells expressing LBAT and contacted with tritiated taurocholate and unlabeled cholate analogs (either Gly-CDC-acid or Gly-CDC-ethyl ester) are presented in FIG. 26B. In this experiment, the efflux of tritiated taurocholate is measured once the cells are contacted with untritiated taurocholate.

EXAMPLE 12

Assay of Uptake by Inhibition Assays

I. Protocol

An alternative to detecting internalization of signal generated from complexes that have been taken up into a cell to identify ligands for a transport protein is to determine whether a test complex inhibits internalization of a known substrate. A protocol by which such assays can be conducted is set forth in Example 2, sections III A and B.

Figure 27B:
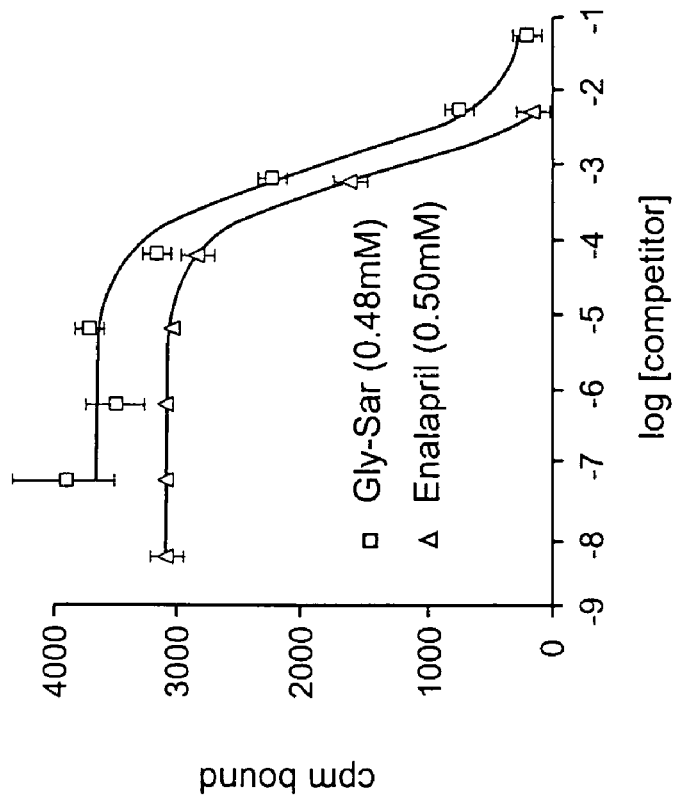
FIGS. 27A and 27B present results demonstrating the inhibitory effect of inhibitors on the activity of known substrates for two different transport proteins.
Figure 27A:
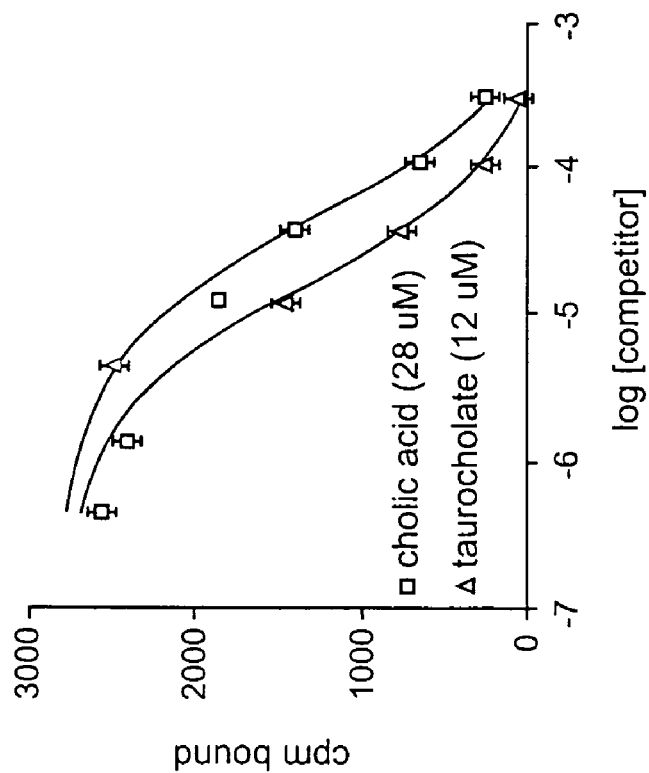

FIG. 27A shows results of inhibition assays for CHO cells expressing the IBAT transporter conducted in the presence of varying concentrations of the known substrates cholic acid or taurocholate in the presence of a fixed concentration of the tritiated substrate taurocholate. The amount of labeled taurocholate bound to the cells is determined by scintillation counting. FIG. 27B shows results for related inhibition studies. In this case, CHO cells expressing PEPT1 are contacted with either of the known substrates Gly-Sar or Enalapril with tritiated Gly-Sar as inhibitor.

EXAMPLE 13

Particle-Based Library Screening Method for Cells Expressing Receptor-Type Transport Proteins I. Screening a 400-Member Dipeptide Library on Fluorescent Nanoparticles A. Split-Pool Synthesis of Library Five mL of an aqueous suspension of 200 nm diameter red fluorescent amino-functionalized polystyrene nanoparticles (Molecular Probes) is centrifuged to pellet the particles, which are washed and resuspended in DMF (0.5 mL). To 1 mL of a DMF solution containing methoxy-PEG-propionic acid, MW 5000, (Shearwater Polymers) (0.1 mmol) and Boc-β-Ala (0.02 mmol) is added HATU (0.12 mmol) and DIEA (0.24 mmol). This mixture is immediately added to the nanoparticles and the suspension shaken for 4 h. After centrifugation, the supernatant is removed and the pellet washed with DMF (3×) and Et$_2$O. The nanoparticles are shaken with 2 mL of a 1:1 (v/v) mixture of TFA and MeCN for 1 h to remove the Boc protecting group from the PEGylated amino nanoparticles.

The particles are then divided into 20 equal aliquots and these are treated with solutions containing one of 20 different protected amino acids (0.5 mmol each) [i.e. Fmoc-Gly, Fmoc-Ala, Fmoc-Val, Fmoc-Leu, Fmoc-Ile, Fmoc-Met, Fmoc-Pro, Fmoc-Cys(Trt), Fmoc-Ser(O$^t$Bu), Fmoc-Thr (O$^t$Bu), Fmoc-Asn(Trt), Fmoc-Gln(Trt), Fmoc-Asp(O$^t$Bu), Fmoc-Glu(O$^t$Bu), Fmoc-Lys(Boc), Fmoc-Arg(Pmc), Fmoc-Phe, Fmoc-Tyr(O$^t$Bu), Fmoc-His(Trt), Fmoc-Trp(Boc)] together with HATU (0.5 mmol) and DIEA (1 mmol) for 4 h. The resins are washed with DMF, Et$_2$O, MeOH, and Et$_2$O again, pooled together and then dried in vacuo. The particles are shaken with 1 mL of a 20% (v/v) solution of piperidine in DMF for 20 min, pelleted by centrifugation and washed with DMF (3×). The particles are then redivided into 20 equal aliquots and these are treated with solutions containing one of 20 different protected D-amino acids (0.5 mmol each) [i.e., Fmoc-Gly, Fmoc-D-Ala, Fmoc-D-Val, Fmoc-D-Leu, Fmoc-D-Ile, Fmoc-D-Met, Fmoc-D-Pro, Fmoc-D-Cys(Trt), Fmoc-D-Ser(O$^t$Bu), Fmoc-D-Thr(O$^t$Bu), Fmoc-D-Asn(Trt), Fmoc-D-Gln(Trt), Fmoc-D-Asp(O$^t$Bu), Fmoc-D-Glu(O$^t$Bu), Fmoc-D-Lys(Boc), Fmoc-D-Arg(Pmc), Fmoc-D-Phe, Fmoc-D-Tyr(O$^t$Bu), Fmoc-D-His(Trt), Fmoc-D-Trp(Boc)] together with HATU (0.5 mmol) and DIEA (1 mmol) for 4 h. The resins are washed with DMF (3×). Each of the 20 pools is then treated with 1 mL of a 20% (v/v) solution of piperidine in DMF for 20 min, pelleted by centrifugation and washed with DMF, Et$_2$O, MeOH, and Et$_2$O again, and then dried in vacuo. Finally, the acid-labile side-chain protecting groups are removed by treatment of each pool with 1 mL of a 90:5:5 solution of TFA: H$_2$O: Et$_3$SiH. The dipeptide-functionalized nanoparticles are washed with MeCN, Et$_2$O, MeOH, and Et$_2$O again, and then dried in vacuo.

B. Screening for Cellular Uptake/Transcytosis of Surface-Decorated Fluorescent Nanoparticles Caco-2 cells are cultured onto 1.2 cm diameter Costar Transwell-Clear filters at a density of 5×10$^5$ cells/cm$^2$ for confocal fluorescence microscopy studies. For each pool of dipeptide-decorated nanoparticles prepared according to the procedure described in the immediately preceding section (i.e., section I.B of this example), ~10$^6$ particles in 1 mL Hanks Balanced Salt Solution (HBSS) are added to the apical side of the monolayer at either 4° C. or 37° C. on an orbital shaker for 2 h. The cells are then rigorously washed with HBSS (3×) to remove non-adherent particles. The filters are counter-stained with FITC-labeled dihexadecanoylglycerol-phosphoethanolamine to label the external cellular membranes, then the monolayers are washed and mounted apical-side to coverslip for confocal microscopy. Optical sections of the Caco cells indicated a monolayer depth of ~20 μm with fluorescent particles accumulating throughout the cytoplasm up to a depth corresponding to the basolateral membrane of the cells. Pools showing the greatest degree of nanoparticle uptake and/or basolateral trafficking are deconvoluted by synthesizing the corresponding 20 individual dipeptide-coated nanoparticle components, and retesting them in this assay.

EXAMPLE 14

Screening for Intestinal Absorption of Surface-Decorated Fluorescent Nanoparticles Nanoparticles (2 mg in 0.1 mL water) from each pool of the dipeptide library displayed on fluorescent nanoparticles described supra in Example 13 are administered to Wistar rats by oral gavage daily over 5 days. The rats are starved overnight before each dose, with food being resumed 1 h later. After the final dose the animals are fasted overnight but allowed water to clear the gut of any unabsorbed nanoparticles. 2 mL of blood is collected into heparin-coated vials from each rat by cardiac puncture. The samples are centrifuged to pellet the particles and counted to quantitate the fraction of administered dose appearing in the systemic circulation. Pools showing the greatest degree of nanoparticle absorption are deconvoluted by synthesizing the corresponding 20 individual dipeptide-coated nanoparticle components, and retesting them in this assay.

EXAMPLE 15

Intestinal Absorption of Fluorescent Zanamivir Bile Acid Propharmaceutical Agents in Rats I. Preparation of Library of Fluorescent Zanamivir Bile Acid Propharmaceutical agents of Type 1

Figure 28:
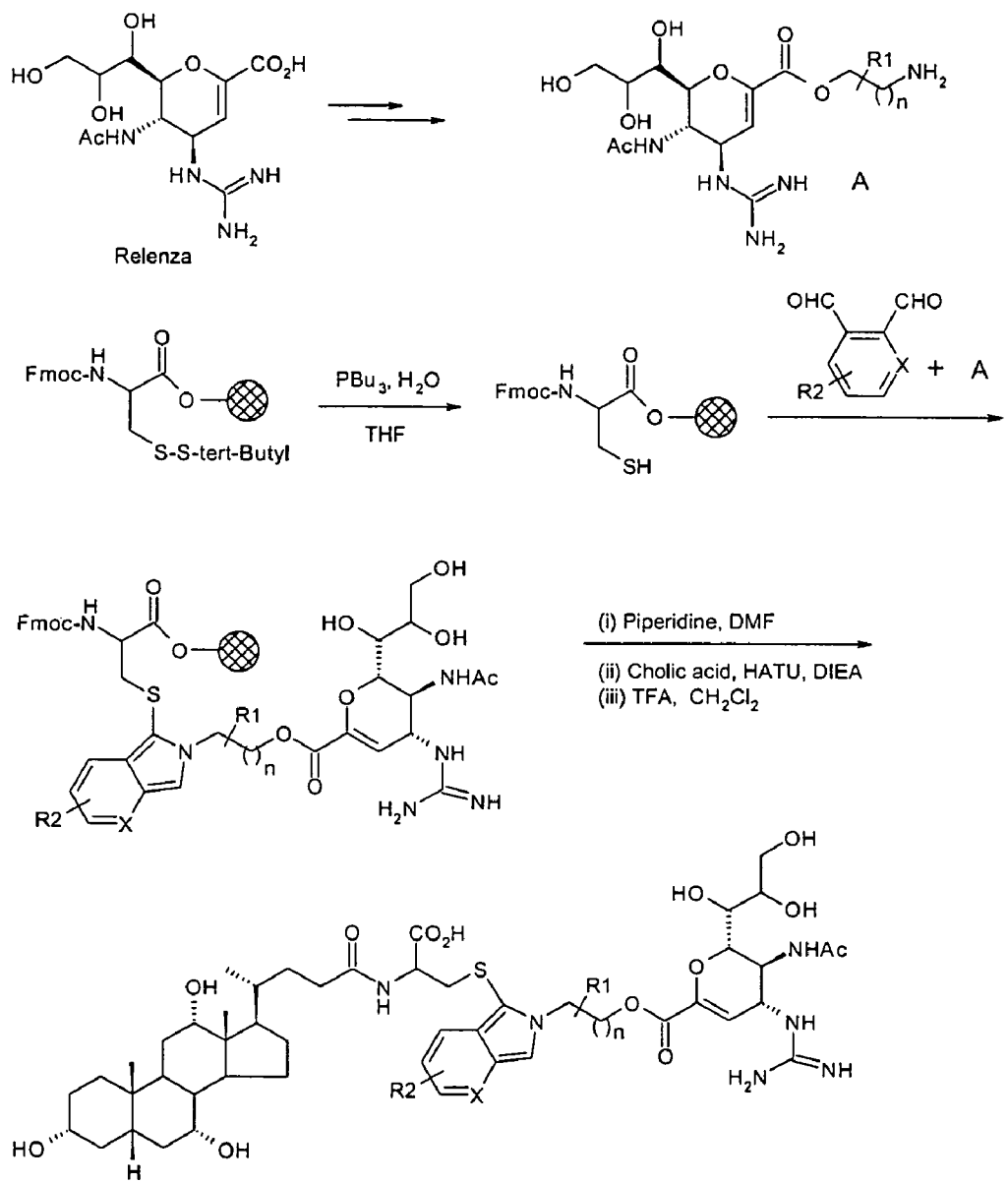
FIGS. 28-30 show the major steps in the synthesis of various libraries of fluorescent Zanamivir bile acid propharmaceutical agents. Compounds from such libraries can be used in studies of intestinal absorption (see Example 15).

Preparation of this library is summarized in FIG. 28. The influenza neuraminidase inhibitor Zanamivir is esterified at its carboxyl moiety with protected amino alcohols under standard conditions and elaborated to provide Zanamivir amino esters of general structure A. Wang resin loaded with a disulfide-protected form of cysteine is deprotected, and the resulting thiol resin reacted with various ortho-phthaldialdehydes in the presence of compounds A to give resin-bound fluorescent isoindole products. The Fmoc protecting group is removed with piperidine and cholic acid is coupled to the support under standard conditions. Cleavage from the resin with TFA in CH$_2$Cl$_2$ afforded a set of fluorescent bile acid propharmaceutical agents of the antiviral compound Zanamivir.

II. Preparation of Library of Fluorescent Zanamivir Bile Acid Propharmaceutical agents of Type 2

Figure 29:
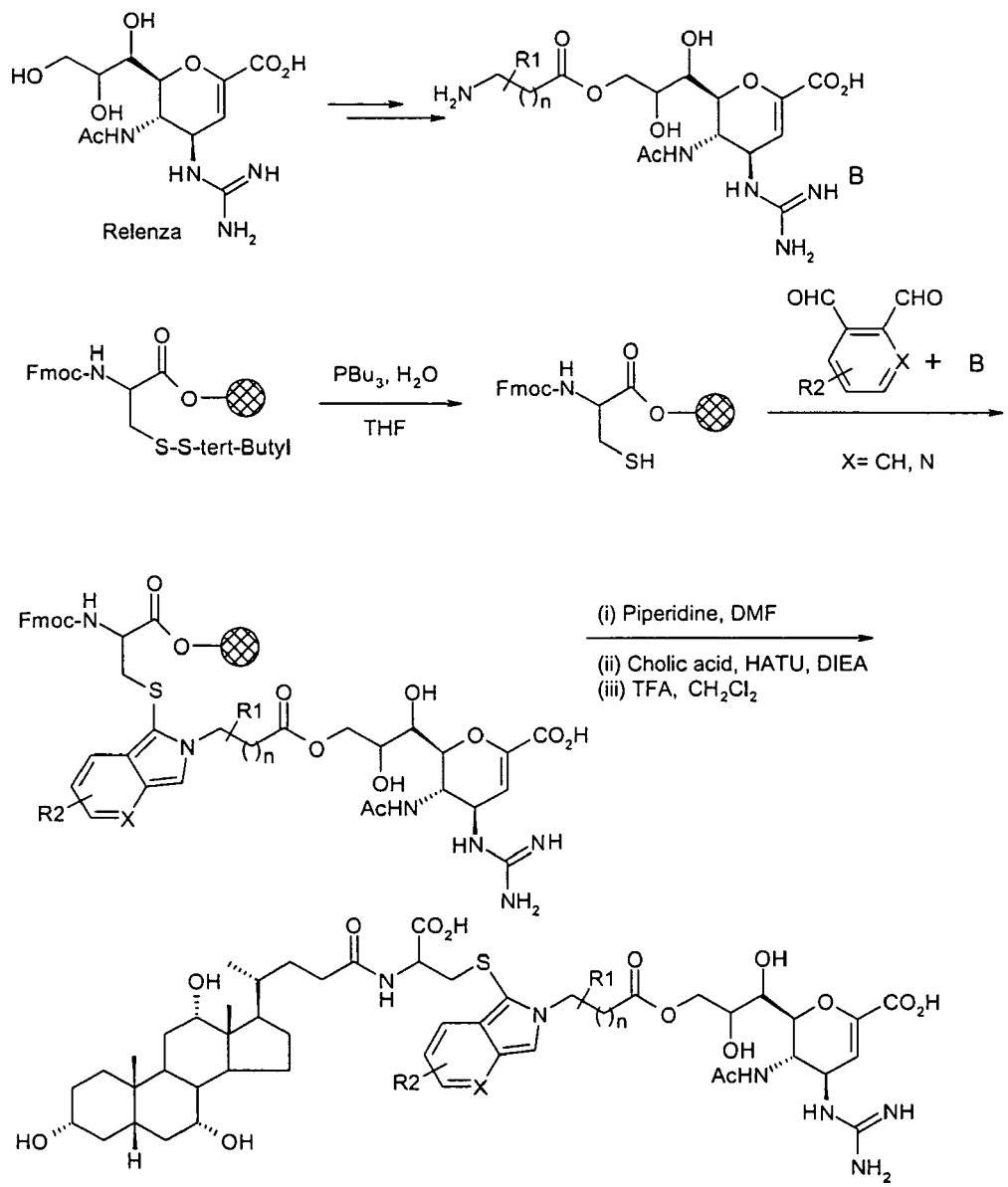

As shown in FIG. 29, the influenza neuraminidase inhibitor Zanamivir is esterified at its primary alcohol moiety with protected amino acids under standard conditions and elaborated to provide Zanamivir amino esters of general structure B. Wang resin loaded with a disulfide-protected form of cysteine is deprotected, and the resulting thiol resin reacted with various ortho-phthaldialdehydes in the presence of compounds B to give resin-bound fluorescent isoindole products. The Fmoc protecting group is removed with piperidine and cholic acid is coupled to the support under standard conditions. Cleavage from the resin with TFA in CH$_2$Cl$_2$ afforded a set of fluorescent bile acid propharmaceutical agents of the antiviral compound Zanamivir.

III. Preparation of Library of Fluorescent Zanamivir Bile Acid Propharmaceutical agents of Type 3

Figure 30:
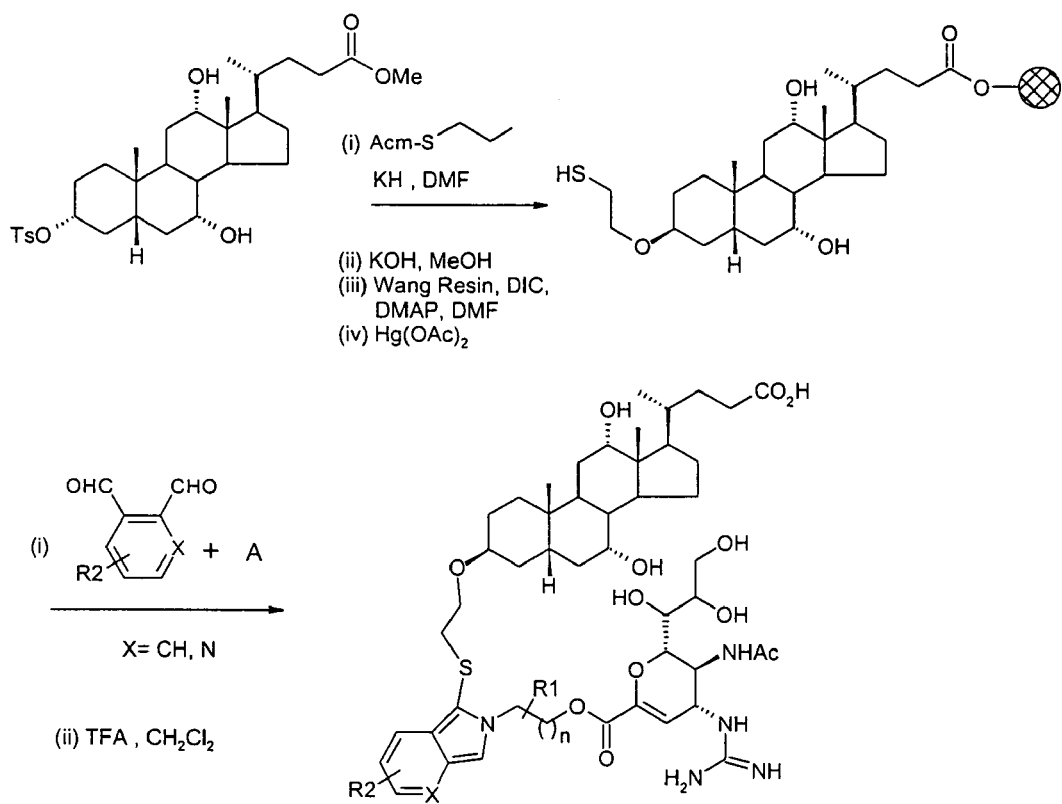

The 3-α-tosylate of methyl cholate, prepared according to literature methods, is treated with S-acetamidomethyl-protected 2-mercaptoethanol under basic conditions and elaborated to give a Wang resin-bound 3β-mercapto-cholate compound. The resulting thiol resin is reacted with various ortho-phthaldialdehydes in the presence of compounds A to yield fluorescent isoindole products. Cleavage from the resin with TFA in CH$_2$Cl$_2$ afforded a set of fluorescent bile acid propharmaceutical agents of the antiviral compound Zanamivir. The synthesis is summarized in FIG. 30.

IV. Detection of Intestinal Absorption

Male Wistar rats are anesthetized and an inlet cannula inserted into the intestinal lumen 8 cm proximal to the ileocecal valve. A second incision is made into the cecum for placement of the outlet cannula and the cannulae connected to a loop of silicone tubing via a peristaltic pump. The loop (total volume 2 mL) is filled with buffer (140 mM NaCl, 0.9 mM $CaCl_2$, 0.5 mM $MgCl_2$, 8 mM $Na_2HPO_4$, 2.7 mM KCl, 1.5 mM $KH_2PO_4$, pH 7.4) and the intestine flushed by flow at 0.25 mL/min. A test compound from one of the foregoing Zanamivir bile acid libraries is introduced into this buffer at 1 mM. The superior mesenteric vein is isolated and blood collected at various time points after perfusion of the test compound and analyzed for appearance of absorbed sample. The blood is centrifuged and the serum analyzed by TLC or HPLC with fluorescence detection for the appearance of both the starting fluorescent propharmaceutical agent as well as the fluorescent byproduct resulting from hydrolysis of the propharmaceutical agent ester.

EXAMPLE 16

Examples of In Vivo Screening for Nanoparticle Transport

A. Initial Screen

A library of tetra peptides is constructed from a building block set consisting of the 39 L- and D-forms of the 20 genetically-encoded amino acids. The library is built by split and pool synthesis on ~$10^{15}$ amino derivatized, 100 nm polystyrene nanoparticles according to the method of Example 13. This results in the production of ~$10^9$ equivalents of the >2 million member library. Following the final coupling step, the beads from all reaction vessels are pooled, washed, and resuspended in 5 mL of saline. The particles are derivatized with biotin, and exposed to a suspension of streptavidin coated, colloidal magnetic particles to attach several magnetic particles to each nanoparticle library support. 0.5 mL of the library suspension is then placed in the small intestine of each fasted rat. In some cases the particles are administered by oral gavage to the duodenal region of the small intestine and allowed to traverse the intestine at a normal rate.

Alternatively, the animals are anesthetized and the small intestine surgically exposed. Portions several cm long of the jejunal and ileal regions of the intestine are isolated by gentle ligature, and 0.5 mL of library suspension injected into the lumen of the isolated loop. In some experiments, blood is taken from the mesenteric vein at periods of 0.5 to 24 h following the administration of the particles. For continuous collection of absorbed particles, a shunt is installed in the mesenteric vein. Blood from the vein is diverted through the shunt to a "particle capture filter" and returned immediately to the vein. The particle capture filter contains a bed of Teflon-coated ferrous fibers with an effective mesh size of greater than 20 μm. The filter is constructed so as to provide minor impedance to the passage of blood cells. During nanoparticle collection, high field permanent magnets (Dynal, Inc) are placed in proximity to the filter housing, temporarily inducing high local magnetic fields in the ferrous fiber bed. This "magnetic filter" permits the efficient recovery of the magnetic nanoparticles from the flowing blood. Periodically, to recover the captured particles, the filter is removed from the shunt circuit and washed with saline to remove residual blood, the external magnetic field is released, and the filter flushed and back-flushed with saline to elute to particles. Recovered beads are washed and concentrated in preparation for analysis. The compounds are cleaved from the beads and analyzed by LC-MS as described in Example 11.

B. Optional Re-Screening

In some experiments, the beads recovered from the screening process described above are re-screened by loading as above into the intestine of a second animal. By beginning with a sufficient number of library equivalents, this process of re-selection can be repeated several times.

C. Whole Body Scintography

As a preliminary assessment of the activity of a particular library or sub-library pool of compounds, whole body scintography is employed. A library constructed as described in Examples 13 and part A of this example is prepared. In a final step, the beads are labeled with $^{99}$Tc. $10^9$ to $10^{12}$ particles (depending on specific activity) of the bead library are administered to fasted rats by any of the methods described in part A of this example. The animals are immobilized and periodically imaged by multiple view gamma cameras to monitor the emigration of nanoparticles to the blood. In some cases, to obtain increased sensitivity and resolution, a solution of non-absorbed radioquencher is added to the intestinal lumen, reducing the background contributed by the bulk of the beads remaining in the intestinal lumen. Decreasing the background produced by the non-mobile beads, allows a more sensitive detection and quantitation of the beads that have moved from the lumen and into the circulation, and it allows a more precise determination of the localization of the absorbed particles. With the appropriately-labeled beads, a variety of 3D imaging technologies can be used in this way: NMR, PET, CAT, thermal imaging, IR fluorescence.

EXAMPLE 17

Assays Utilizing Membrane Vesicles

I. General

Plasma membrane vesicles can be used to study the transport characteristics of solute transporters. Vesicles are prepared from cells that express the transporter of interest and exposed to a substrate labeled in such a way as to be conveniently detected within the vesicles. One useful application of vesicle-based assay of transporters is their use in the study of efflux transporters, such as those members of the ATP-binding cassette (ABC) family. In order to study transport mediated by these unidirectional transporter in intact cells, the cells are first be loaded with the compound under study, and the efflux of the compound from the cells is followed. Membrane vesicles can be prepared so that a significant proportion of the vesicles are "inside out," that is the efflux transporters are oriented so that they pump substrates into the interior of the vesicles. The free external compound is then removed, by centrifugation of the vesicles for example, and the compound that has entered the vesicles is determined.

II. Membrane Vesicles Prepared from CHO Cells Expressing spgp (Sister of P-Glyco-Protein) Used in Assay of Taurocholate Uptake.

Sister of P-glycoprotein is the major canalicular bile acid transporter in the mammalian liver, and is also called the "Bile Salt Export Pump" (BSEP).

A. Preparation of Vesicles

The rat BSEP is transfected into CHO cells and expressed at a high level in the plasma membrane. Cells are scrapped from the culture plates and centrifuged at 1400×g, the pellet recovered and homogenized with a Teflon/glass homogenizer in 50 mM mannitol, 2 mM EGTA, 50 mM tris pH 7.0, 1 μg leupeptin/antipain, and 0.5 mM phenylmethylsulfonyl fluoride. Undisrupted cells, nuclear debris, and mitochondria are pelleted by centrifuging at 500×g for 10 min. The supernatant is centrifuged at 100,000×g for 1 h. The resulting pellet is resuspended in bile acid uptake buffer consisting of 50 mM sucrose, 100 mM KNO3, 12.5 mM Mg(NO3)$_2$, and 10 mM HEPES/TRIS pH 7.4. The vesicles can be stored in liquid nitrogen prior to use in assays.

B. Assays for ATP-Dependent Compound Uptake

To an appropriate aliquot of the vesicle preparation is added 2 µM of the fluorescent reporter-tagged test compound and 5 mM ATP. Assay is incubated at RT for 20 min. At the end of the incubation period, reaction is stopped by placing the incubations on ice. The incubation medium is filtered through glass fiber filters and washed to remove the unincorporated test compound, and the fluorescence of the filters is measured to determine uptake of the test compound.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes to the same extent as if each individual publication, patent or patent application were specifically and individually indicated to be so incorporated by reference.

What is claimed is:

1. A method of screening for a carrier-mediated transport protein and/or a substrate thereto, comprising:
    (a) providing a library comprising different complexes, each complex comprising a compound and a separate reporter, the compound varying between different complexes;
    (b) providing one or more cells, each cell expressing a carrier-mediated transport protein;
    (c) contacting the one or more cells with a plurality of complexes from the library simultaneously; and
    (d) selectively detecting a signal from a reporter internalized within one or more of the cells as compared to signal from reporter outside the cell to indicate that a complex whose reporter generated the signal comprises a compound that is a substrate for a carrier-mediated transport protein;
    provided that if the reporter comprises a fluorophore, the complex comprises a compound, a fluorophore and a quencher, and the fluorophore is linked to the quencher by a linker susceptible to cleavage within the cell, whereby the quencher quenches fluorescence from the fluorophore outside the cell and is cleaved from the fluorophore within the cell after the complex is internalized within the cell, whereby the reporter preferentially generates the signal once internalized within the cell.

2. The method of claim 1, wherein the reporter comprises a fluorophore and a quencher moiety, and if a compound complexed with the reporter is a substrate for the carrier-mediated transport protein, the complex is transported by the carrier-mediated transport protein into a cell expressing the carrier-mediated transport protein, whereby the quencher moiety becomes separated from the fluorophore such that a fluorescent signal is emitted by the fluorophore within the cell, and the detection step comprises detecting the fluorescent signal.

3. The method of claim 1, wherein the reporter comprises a substrate for an enzyme, and if a compound complexed with the reporter is a substrate for the carrier-mediated transport protein, the complex is transported by the carrier-mediated transport protein into a cell expressing the carrier-mediated transport protein and the enzyme, whereby the enzyme metabolizes the substrate to form a detectable product, and the detecting step comprises detecting the detectable product.

4. A method of screening for a carrier-mediated transport protein and/or a ligand thereto, comprising:
    (a) providing a library comprising different complexes, each complex comprising a compound and a separate reporter, the compound varying between different complexes;
    (b) providing one or more cells, each cell expressing a carrier-mediated transport protein, and located in a single reaction vessel;
    (c) contacting the one or more cells with a plurality of complexes from the library simultaneously, the compound and reporter varying between different complexes and different reporters disposed to generate different signals, whereby at least one complex is bound to or internalized within the one or more cells; and
    (d) detecting the signal from the reporter of the at least one complex, the signal providing an indication of the identity of the compound borne by the at least one complex.

5. A method of screening for a carrier-mediated transport protein and/or a substrate thereto, comprising:
    (a) providing one or more cells, each cell expressing a carrier-mediated transport protein;
    (b) contacting the one or more cells with one or more complexes, each complex comprising a compound and a reporter;
    (c) detecting a signal from a reporter internalized within the one or more cells to identify at least one complex that is internalized within the one or more cells, the compound of the internalized complex being a substrate potentially disposed to transport a pharmaceutical agent into a cell via the activity of a carrier-mediated transport protein;
    (d) preparing a modified complex, the modified complex comprising the compound identified in step (c) and a pharmaceutical agent;
    (e) repeating steps (a) and (b) with the modified complex; and
    (f) determining whether the modified complex is internalized within one of the one or more cells by detecting the modified complex within the one or more cells, such detection providing an indication that the compound of the modified complex can serve as a substrate for transporting a pharmaceutical agent into cells expressing carrier-mediated transport proteins.

6. A method of screening for a carrier-mediated transport protein and/or a substrate thereto, comprising:
    (a) providing one or more cells, each cell expressing a carrier-mediated transport protein;
    (b) contacting the one or more cells with one or more complexes, each complex comprising a compound and a reporter; and
    (c) selectively detecting a signal from a reporter internalized within one or more of the cells as compared to signal from reporter outside the cell to indicate that a complex whose reporter generated the signal comprises a compound that is a substrate for a carrier-mediated transport protein;
    wherein the contacting step results in at least one complex being internalized in a cell, the reporter is a fluorophore that fluoresces upon binding to a nucleic acid within the cell, which fluorescence is detected in the detecting step.

7. A method of screening for a carrier-mediated transport protein and/or a substrate thereto, comprising:
    (a) providing one or more cells, each cell expressing a carrier-mediated transport protein;

(b) contacting the one or more cells with one or more complexes, each complex comprising a compound and a reporter; and (c) selectively detecting a signal from a reporter internalized within one or more of the cells as compared to signal from reporter outside the cell to indicate that a complex whose reporter generated the signal comprises a compound that is a substrate for a carrier-mediated transport protein;

wherein the contacting step results in at least one complex being internalized in a cell, the reporter promotes aggregation of subunits of a multimeric enzyme expressed within the cell, and the enzyme catalyzes production of a product that generates a detectable signal, and detecting comprises detecting the detectable signal.

8. A method of screening for a carrier-mediated transport protein and/or a substrate thereto, comprising:

(a) providing one or more cells, each cell expressing a carrier-mediated transport protein;

(b) contacting the one or more cells with one or more complexes, each complex comprising a compound and a reporter; and (c) selectively detecting a signal from a reporter internalized within one or more of the cells as compared to signal from reporter outside the cell to indicate that a complex whose reporter generated the signal comprises a compound that is a substrate for a carrier-mediated transport protein;

wherein the contacting step results in at least one complex being internalized in a cell, the reporter promotes transcription of a promoter within a cell resulting in expression of an enzyme that catalyzes production of a product that generates a detectable signal, and detecting comprises detecting the detectable signal.

* * * * *